United States Patent
Margulies et al.

(10) Patent No.: US 10,557,852 B2
(45) Date of Patent: Feb. 11, 2020

(54) FLUORESCENT MOLECULAR SENSOR FOR TARGETING CHANGES IN PROTEIN SURFACES, AND METHODS OF USE THEREOF

(71) Applicant: YEDA RESEARCH AND DEVELOPMENT CO. LTD., Rehovot (IL)

(72) Inventors: David Margulies, Rehovot (IL); Leila Motiei, Rehovot (IL); Naama Mankovski, Rehovot (IL); Yael Nissinkorn, Rehovot (IL)

(73) Assignee: YEDA RESEARCH AND DEVELOPMENT CO. LTD., Rehovot (IL)

( * ) Notice: Subject to any disclaimer, the term of this patent is extended or adjusted under 35 U.S.C. 154(b) by 125 days.

(21) Appl. No.: 15/307,011

(22) PCT Filed: Apr. 28, 2015

(86) PCT No.: PCT/IL2015/050441
§ 371 (c)(1),
(2) Date: Oct. 27, 2016

(87) PCT Pub. No.: WO2015/166491
PCT Pub. Date: Nov. 5, 2015

(65) Prior Publication Data
US 2017/0045522 A1    Feb. 16, 2017

Related U.S. Application Data

(60) Provisional application No. 61/985,555, filed on Apr. 29, 2014.

(51) Int. Cl.
*G01N 33/58* (2006.01)
*G01N 33/68* (2006.01)

(52) U.S. Cl.
CPC ....... *G01N 33/582* (2013.01); *G01N 33/6803* (2013.01); *G01N 2570/00* (2013.01)

(58) Field of Classification Search
CPC .... C07D 249/04; C07K 1/13; G01N 33/5005; G01N 33/5008; G01N 33/533; G01N 33/582; G01N 33/6803; G01N 2570/00
See application file for complete search history.

(56) References Cited

U.S. PATENT DOCUMENTS

| 2008/0038750 | A1 | 2/2008 | Piehler et al. |
| 2014/0038856 | A1 | 2/2014 | Gee et al. |
| 2015/0112047 | A1* | 4/2015 | Schmidt ................ G01N 33/58 530/395 |

FOREIGN PATENT DOCUMENTS

| WO | WO-0047548 A1 * | 8/2000 | ........... C07C 217/28 |
| WO | WO 2012/159051 A2 | 11/2012 | |

OTHER PUBLICATIONS

You et al. Multivalent chelators for spatially and temporally controlled protein functionalization. Anal Bioanal Chem 2014, vol. 406, pp. 3345-3357. (Year: 2014).*

(Continued)

*Primary Examiner* — Shafiqul Haq
(74) *Attorney, Agent, or Firm* — Mark S. Cohen; Pearl Cohen Zedek Latzer Baratz LLP

(57) ABSTRACT

This invention is directed to monomolecular sensors, comprising a selective binder, a non-selective binder and a fluorophore, which can track changes that occur on the surface of labeled proteins. This invention is further directed to the use of such sensors for identifying binding partners of specific proteins. This invention is further directed to His-tag binding compounds and uses thereof in the preparation of genetically targeted detectable molecules and sensors which can specifically bind tag-labeled proteins.

12 Claims, 35 Drawing Sheets
Specification includes a Sequence Listing.

(1a)    (1b)    (1c)

(56) References Cited

OTHER PUBLICATIONS

Cardona et al. "An improved synthesis of a trifurcated newkome-type monomer and orthogonally protected two-generation dendrons" The Journal of organic chemistry. Feb. 22, 2002;67(4):1411.

Chen et al. "Synthesis of the Rheb and K-Ras48 GTPases" Angewandte Chemie (International ed. in English). Aug. 16, 2010;49(35):6090.

Cohen et al. "Probing protein electrostatics with a synthetic fluorescent amino acid" Science (New York, NY). May 31, 2002;296(5573):1700.

Crivici et el. "Molecular and structural basis of target recognition by calmodulin" Annual review of biophysics and biomolecular structure, 1995;24:85.

"Fluorophores.org—Database of Fluorecent Dyes, Properties and Applications" download Jul. 9, 2018 from: http://www.fluorophores.org.

Fujishima et al. "Design of a multinuclear Zn (II) complex as a new molecular probe for fluorescence imaging of His-tag fused proteins" Chemical communications (Cambridge, England). Jan. 14, 2012;48(4):594.

Fukuda et al. "Aggregation of Alzheimer amyloid beta peptide (1-42) on the multivalent sulfonated sugar interface" Bioconjugate chemistry. Jun. 16, 2010;21(6):1079.

Grabchev et al. "A copolymer of 4-N, N-dimethylaminoethylene-N-allyl-1, 8-naphthalimide with methylmethacrylate as a selective fluorescent chemosensor in homogeneous systems for metal cations" Journal of Photochemistry and Photobiology A: chemistry, May 30, 2003;158(1):37-43.

Griffin et al. "Specific covalent labeling of recombinant protein molecules inside live cells" Science (New York, NY). Jul. 10, 1998;281(5374):269.

Guignet et al. "Reversible site-selective labeling of membrane proteins in live cells" Nature biotechnology. Apr. 2004;22(4):440.

Halo et al. "Selective recognition of protein tetraserine motifs with a cell-permeable, pro-fluorescent bis-boronic acid" Journal of the American Chemical Society. Jan. 21, 2000;131(2):438.

Hauser et al. "A hexahistidine-Zn2+-dye label reveals STIM1 surface exposure" Proceedings of the National Academy of Sciences. Mar. 6, 2007;104(10):3693-7.

Honda et al. "Pyrene excimer-based dual-emission detection of a oligoaspartate tag-fused protein by using a Zn (II)-DpaTyr probe" Chembiochem: a European journal of chemical biology. Aug. 13, 2007;8(12):1370.

Huang et al. "Facile synthesis of multivalent nitrilotriacetic acid (NTA) and NTA conjugates for analytical and drug delivery applications" Bioconjugate chemistry. 2006;17(6):1592.

Kamoto et al. "Novel probes showing specific fluorescence enhancement on binding to a hexahistidine tag" Chemistry (Weinheim an der Bergstrasse, Germany). 2008;14(26):8004.

Lata et al. "Specific and stable fluorescence labeling of histidine-tagged proteins for dissecting multi-protein complex formation" Journal of the American Chemical Society. Feb. 22, 2006;128(7):2385-72.

Lata et al. "High-affinity adaptors for switchable recognition of histidine-tagged proteins" Journal of the American Chemical Society. Jul. 27, 2005;127(29):10205.

Lee et al. "Bodipy-diacrylate imaging probes for targeted proteins inside live cells" Chemical communications (Cambridge, England). Apr. 21, 2011;47(15):4508.

Martin et al. "Solvent dependence of the inhibition of intramolecular charge-transfer in N-substituted 1, 8-naphthalimide derivatives as dye lasers" Journal of luminescence. May 1, 1996;68(2-4):157-64.

Murata et al. "Construction of a'turn-on'fluorescent probe system for His-tagged proteins" Bioorganic & medicinal chemistry letters. Dec. 1, 2010;20(23):6905.

Nonaka et al. "Selective covalent labeling of tag-fused GPCR proteins on live cell surface with a synthetic probe for their functional analysis" Journal of the American Chemical Society. Jul. 14, 2010;132(27):9301.

Ojida et al. "Oligo-Asp tag/Zn (II) complex probe as a new pair for labeling and fluorescence imaging of proteins" Journal of the American Chemical Society. Aug. 16, 2006;128(32):10452.

Saroja et al. "4-Aminophthalimide derivatives as environment-sensitive probes" Journal of Fluorescence. Dec. 1, 1998;8(4):405-10.

Soh et al. "Methodology of reversible protein labeling for ratiometric fluorescent measurement" Molecular bioSystems. Feb. 2006;2(2):128.

Soh N. "Selective Chemical Labeling of Proteins with Small Fluorescent Molecules Based on Metal-Chelation Methodology" Sensors (Basel, Switzerland). Feb. 2008;8(2):1004.

Szent-Gyorgyi et al. "Fluorogen-activating single-chain antibodies for imaging cell surface proteins" Nature biotechnology. Feb. 2008;26(2):235.

Vassiliou et al. "Detection of low-affinity adhesion ligands by linking recombinant cell adhesion molecules in uniform orientation to a fluorescently labelled dextran molecule by means of hexahistidine tagging: the case of milltimeric CD40" Journal of immunological methods. Jun. 1, 1998;215(1-2):9.

Weber et al. "Synthesis and spectral properties of a hydrophobic fluorescent probe: 6-propionyl-2-(dimethylamino) naphthalene." Biochemistry. Jul. 10, 1979;18(14):3075.

Huang et al. "Tris-nitrilotriacetic acids of subnanomolar affinity toward hexahistidine tagged molecules" Bioconjugate chemistry. Aug. 3, 2009;20(8):1667-72.

\* cited by examiner

| Compound | Peptide Sequence | Receptor Type |
| --- | --- | --- |
| 1 | $N_3$-$(CH_2)_3$-G-S-L-I-$CONH_2$ | hydrophobic |
| 2 | $N_3$-$(CH_2)_3$-G-E-S-E-COOH | negatively-charged |
| 3 | $N_3$-$(CH_2)_3$-S-G-S-S-COOH | polar |
| 4 | $N_3$-$(CH_2)_3$-S-K-S-K-$CONH_2$ | positively-charged |
| 5 | $N_3$-$(CH_2)_3$-I-L-K-S-I-K-$CONH_2$ | positively-charged and hydrophobic |

SEQUENCE LISTING

<160> NUMBER OF SEQ ID NOS: 5

<210> SEQ ID NO 1
<211> LENGTH: 4
<212> TYPE: PRT
<213> ORGANISM: Artificial Sequence
<220> FEATURE:
<223> OTHER INFORMATION: Artificial Peptide Sequence

```
<400> SEQUENCE: 1

Ile Leu Ser Gly
1

<210> SEQ ID NO 2
<211> LENGTH: 4
<212> TYPE: PRT
<213> ORGANISM: Artificial Sequence
<220> FEATURE:
<223> OTHER INFORMATION: Artificial Peptide Sequence

<400> SEQUENCE: 2

Gly Glu Ser Glu
1

<210> SEQ ID NO 3
<211> LENGTH: 4
<212> TYPE: PRT
<213> ORGANISM: Artificial Sequence
<220> FEATURE:
<223> OTHER INFORMATION: Artificial Peptide Sequence

<400> SEQUENCE: 3

Ser Gly Ser Ser
1

<210> SEQ ID NO 4
<211> LENGTH: 4
<212> TYPE: PRT
<213> ORGANISM: Artificial Sequence
<220> FEATURE:
<223> OTHER INFORMATION: Artificial Peptide Sequence

<400> SEQUENCE: 4

Ser Lys Ser Lys
1

<210> SEQ ID NO 5
<211> LENGTH: 6
<212> TYPE: PRT
<213> ORGANISM: Artificial Sequence
<220> FEATURE:
<223> OTHER INFORMATION: Artificial Peptide Sequence

<400> SEQUENCE: 5

Ile Leu Lys Ser Ile Lys
1               5
```

FLUORESCENT MOLECULAR SENSOR FOR TARGETING CHANGES IN PROTEIN SURFACES, AND METHODS OF USE THEREOF

CROSS-REFERENCE TO RELATED APPLICATIONS

This application is a National Phase Application of PCT International Application No. PCT/IL2015/050441, International Filing Date Apr. 28, 2015, claiming priority of U.S. Provisional Patent Application No. 61/985,555, filed Apr. 29, 2014, which are incorporated in their entirety herein by reference.

FIELD OF THE INVENTION

This invention is directed to monomolecular sensors, comprising a selective binder, a non-selective binder and a fluorophore, which can track changes that occur on the surface of labeled proteins. This invention is further directed to the use of such sensors for identifying binding partners of specific proteins. This invention is further directed to His-tag binding compounds and uses thereof in the preparation of genetically targeted detectable molecules and sensors which can specifically bind tag-labeled proteins.

BACKGROUND OF THE INVENTION

Fluorescent molecular probes that can label, detect, or image specific proteins serve as a powerful tool for developing in-vitro proteomic assays, for identifying disease biomarkers, as well as for tracking proteins in complex environments.

Fluorescent molecular sensors have become valuable tools in the analytical biosciences owing to their sensitive detection mode, down to the level of a single molecule, the feasibility of naked eye visualization, their versatility, and their small size, which enable them to penetrate the cell membrane and track the rise and fall of various bio-analytes within living cells. Although fluorescent sensors that utilize photo-induced electron transfer (PET), electronic energy transfer (EET) (or fluorescence resonance energy transfer (FRET), and internal charge transfer (ICT) processes have been developed and used to detect various proteins, most of them suffer from a high background signal that complicates their use in complex biochemical mixtures and within cells.

There is a growing interest in developing "genetically targeted fluorescent molecules", namely, small molecule-based fluorescent probes that can bind to short, peptide motifs on the protein of interest and, in doing so, enable the protein's labeling or detection in complex biological environments such as within live cells. Such sensors provide an alternative to using recombinant technology to create a fusion protein comprising the protein of interest with fluorescent proteins (FPs) (e.g., green fluorescent proteins or GFPs) whose large size can interrupt the normal function of many proteins. These genetically targeted probes have already become commercial, for example, the FlAsH-and-ReAsH probes for the selective labeling of tetra-cysteine motifs that are now sold online by Life Technologies.

Genetically encoded fluorescent proteins (FPs) have revolutionized the study of biology by allowing one to track protein expression and localization in living cells at spatial and temporal resolution. This method, however, involves the use of very large protein that can interfere with the normal function of the labeled protein. Over the last few years, it has been demonstrated that this problem can be circumvented by expressing the proteins with a very short peptide sequence to which a small fluorescent molecular sensor, termed "genetically-targeted sensors" can attach. Sensors that can bind to an oligohistidine sequence (i.e. His-tag) with high affinity and can be applied for labeling and detecting a wide range of His-tagged proteins in living cells.

The histidine tag is currently the most widely used tag in protein purification. It is typically composed of six or ten histidine residues fused at the amino or carboxyl terminus of a protein. Recombinant proteins containing a histidine tag are commonly purified on a matrix with nickel(II)-nitrilotriacetate (Ni-NTA) complexes that are prepared from nickel (II)-activation of nitrilotriacetic acid (NTA). In addition to protein purification, this technology has been used in label-free surface plasmon resonance (SPR) biosensors for biomolecular interaction analysis that involves histidine-tagged proteins.

Protein surface recognition by synthetic receptors is an important research direction in the areas of bioorganic and medicinal chemistry, particularly due to the ability of such receptors to disrupt the interactions between two proteins. Such systems can be obtained, for example, by mimicking essential interacting motifs (e.g., $\alpha$-helices) of one of the protein partners. Alternatively, they may be inspired by the structure of antibodies and consist of larger receptors that complement hydrogen-bonding, hydrophobic, and charged groups on the surface of the target proteins. Despite these significant advances, protein surface recognition by synthetic agents remains challenging owing to the immense complexity of the biological targets. Specifically, protein surfaces are generally large and flat, and lack well-defined grooves and pockets that can serve as templates for designing synthetic binding partners.

Similar challenges hamper the development of fluorescent molecular sensors that can track changes that occur on the surfaces of specific proteins. If available, such systems would facilitate detecting protein modifications and binding interactions, which are difficult to sense with the current luminescent probes. Chromophoric protein surface receptors, for example, which have been used to discriminate among protein surfaces, can generally do so in the form of cross-reactive sensor arrays that are inherently not specific. Fluorescent molecular sensors and probes, on the other hand, which can efficiently detect, label, and image specific proteins, are normally designed to target only small and well-defined recognition domains. Tracking protein surface modifications by such sensors is therefore indirect, namely, the modifications must induce a significant change at the probe's binding site.

Herein, a step toward circumventing the challenges associated with sensing surfaces of specific proteins with synthetic receptors is demonstrated. In particular, it is demonstrated how the attachment of protein surface receptors to genetically targeted small molecules can afford fluorescent sensors that respond to changes in the surfaces of affinity-labelled proteins, upon binding to metal ions, small molecules, and protein partners. It is herein demonstrated how combination of flexible linker with a modifiable synthetic receptor enables the design of various sensors that match different regions on the surface of various proteins. The way this method could be used to sense surface modifications of unlabeled proteins is also presented.

SUMMARY OF THE INVENTION

In one embodiment, this invention is directed to a monomolecular compound, that can track changes that occur on the surface of tag-labeled proteins, said compound comprises:

a. A Tag binding region;
b. A non-selective binder; and
c. A fluorophore.

In another embodiment, the monomolecular compound is a sensor for detecting 3D changes on a protein surface. In another embodiment, the Tag-binding region comprises a His-tag binder.

In another embodiment, the non-selective binder is represented by the structure of formula (A):

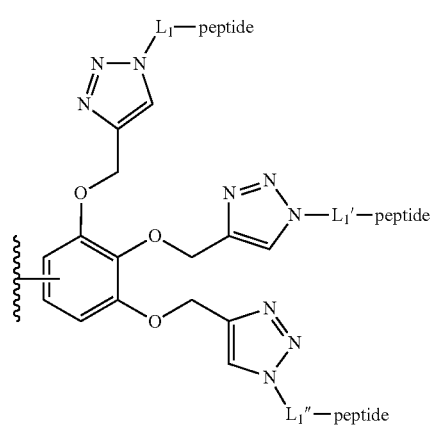

(A)

wherein
wherein each of $L_1$, $L_1'$ and $L_1''$ is independently substituted or unsubstituted linear or branched alkyl chain of 1-50 carbon atoms, substituted or unsubstituted linear or branched alkyl ether chain of 1-50 carbon atoms, substituted or unsubstituted linear or branched alkyl phosphate chain of 1-50 carbon atoms, substituted or unsubstituted linear or branched alkyl amide chain of 1-50 carbon atoms, substituted or unsubstituted linear or branched alkyl diamide chain of 1-50 carbon atoms, substituted or unsubstituted linear or branched alkyl amine chain of 1-50 carbon atoms or any combination thereof; and
wherein a peptide comprises a 2-20 amino acid peptide.

In another embodiment, the His-tag binder is represented by the structure of formula D:

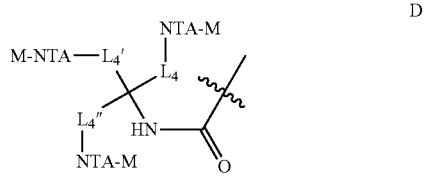

D wherein each of $L_4$, $L_4'$, and $L_4''$ is independently a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof; and M-NTA is a metal complex of nitrilotriacetic acid.

In another embodiment, the monomolecular compound (sensor for detecting 3D changes on a protein surface) further comprises a linker, which covalently links between the Tag-binding region and the non-selective binder. In another embodiment, the linker is further covalently attached to said fluorophore in the vicinity of said non-selective binder.

In another embodiment, the monomolecular compound is represented by the structure of formula IV:

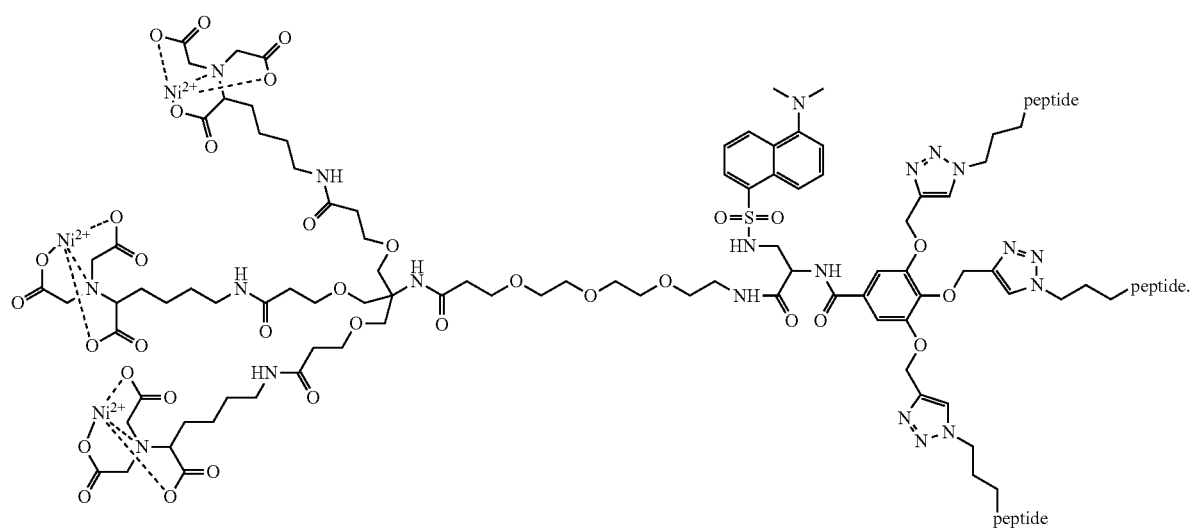

IV

In one embodiment, this invention is directed to a method of identifying a binding partner of protein of interest (POI), said method comprises:
a. incubating a monomolecular compound of this invention, with a tagged-POI in solution;
b. measuring the fluorescence intensity of said solution;

c. adding a test compound to said solution;
d. remeasuring the fluorescence intensity of said solution; and
e. determining binding of said test compound to said tagged-POI based on a change in fluorescence intensity, wherein decreased fluorescent intensity indicates binding of said test compound;
thereby identifying said binding partner for said POI.

In another embodiment, the tagged-POI comprises a His-tag. In another embodiment, the binding partner is a protein, a peptide, a synthetic molecule, a small molecule, a drug or any combination thereof.

In one embodiment, this invention is directed to a His-tag binding compound, represented by the structure of formula X:

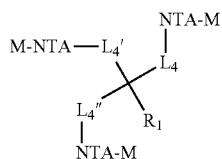

wherein
R$_1$ is azide, amine, C$_2$-C$_6$ alkynyl, thioester, disulfide, maleimide, biotin, carboxyl, thiol, triazole, alkylamide, carbamate, or R$_1$ is selected from:

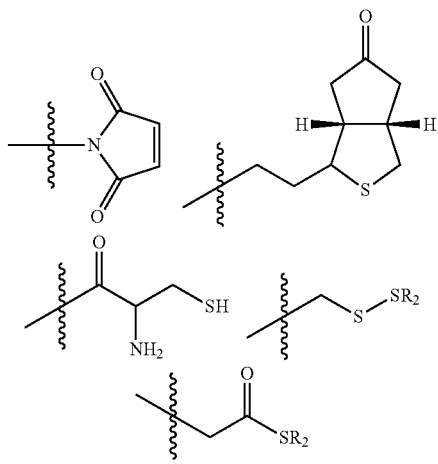

wherein
R$_2$ is hydrogen, substituted or unsubstituted linear or branched C$_1$-C$_{12}$ alkyl, substituted or unsubstituted linear or branched C$_1$-C$_{12}$ arylalkyl or benzyl;
each of L$_4$, L$_4$', and L$_4$" is independently a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof;
M is a metal ion; and
NTA is nitrilotriacetic acid.

In another embodiment, the His-tag binding compound is represented by the structure of formula XX(a):

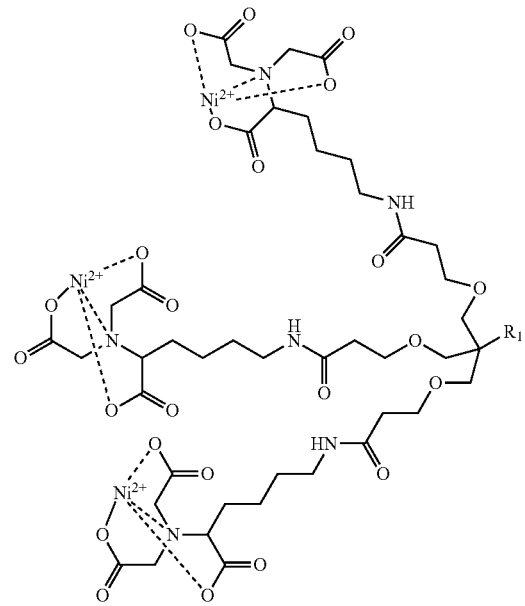

wherein
R$_1$ is azide, amine, C$_2$-C$_6$ alkynyl, thioester, disulfide, maleimide, biotin, carboxyl, thiol, triazole, alkylamide, carbamate, or R$_1$ is selected from:

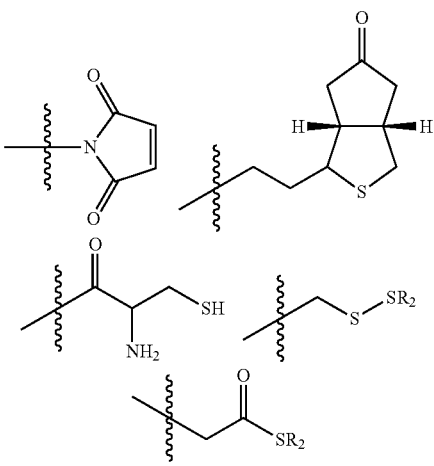

wherein
R$_2$ is hydrogen, substituted or unsubstituted linear or branched C$_1$-C$_{12}$ alkyl, substituted or unsubstituted linear or branched C$_1$-C$_{12}$ arylalkyl or benzyl.

In another embodiment, the His-tag binding compound is coupled through the R$_1$ moiety to an oligonucleotide, a peptide, a protein, a small molecule, or any combination thereof. In another embodiment, the His-tag binding compound is substituted at the R$_1$ position with a detectable group. In another embodiment, the detectable group comprises a fluorescent group. In another embodiment, the compound specifically reacts with a His-tag sequence to generate a fluorescent signal. In another embodiment, the compound is capable of traversing a biological membrane. In another embodiment, the compound is coupled to a solid phase.

In one embodiment, this invention is directed to a fluorescently tagged His-tag binding compound, comprising the His-tag binding compound according to this invention, wherein said His-tag binding compound is covalently linked to a fluorophore through the $R_1$ moiety.

In one embodiment, this invention is directed to a fluorescently tagged His-tag binding compound, comprising the His-tag binding compound according to this invention, wherein said compound is covalently linked to a fluorophore through a linker, which links between the $R_1$ moiety of said compound and said fluorophore.

In one embodiment, this invention is directed to a method of localizing a His-tagged polypeptide of interest within a cell, said method comprises:
   a. expressing said His-tagged polypeptide in a recombinant cell;
   b. incubating said recombinant cell with a fluorescently-tagged His-tag binding compound according to this invention; and
   c. visualizing the fluorescence emission of said fluorescently tagged His-tag binding compound.

In one embodiment, this invention is directed to a method of localizing a His-tagged polypeptide of interest, said method comprises:
   a. expressing said His-tagged polypeptide in a recombinant cell;
   b. incubating said recombinant cell with a monomolecular compound according to this invention (sensor); and
   c. visualizing the fluorescence emission of said monomolecular compound (sensor).

In one embodiment, this invention is directed to a method of measuring gene expression of a His-tagged polypeptide in a cell, said method comprises the steps of:
   a. expressing a His-tagged polypeptide in a cell;
   b. incubating said cell with a fluorescently-tagged His-tag binding compound according to this invention; and
   c. measuring the fluorescence of said cell;
wherein detection of a fluorescent signal is dependent on the formation of a His-tagged polypeptide:fluorescently tagged His-tag binding compound complex.

In one embodiment, this invention is directed to a method of measuring gene expression of a His-tagged polypeptide of interest in a cell, said method comprises:
   a. expressing a His-tagged polypeptide in a cell;
   b. incubating said cell with a monomolecular compound (sensor) according to this invention; and
   c. measuring the fluorescence emission of said cell;
wherein detection of a fluorescent signal is dependent on the formation of a His-tagged polypeptide:monomolecular compound complex.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
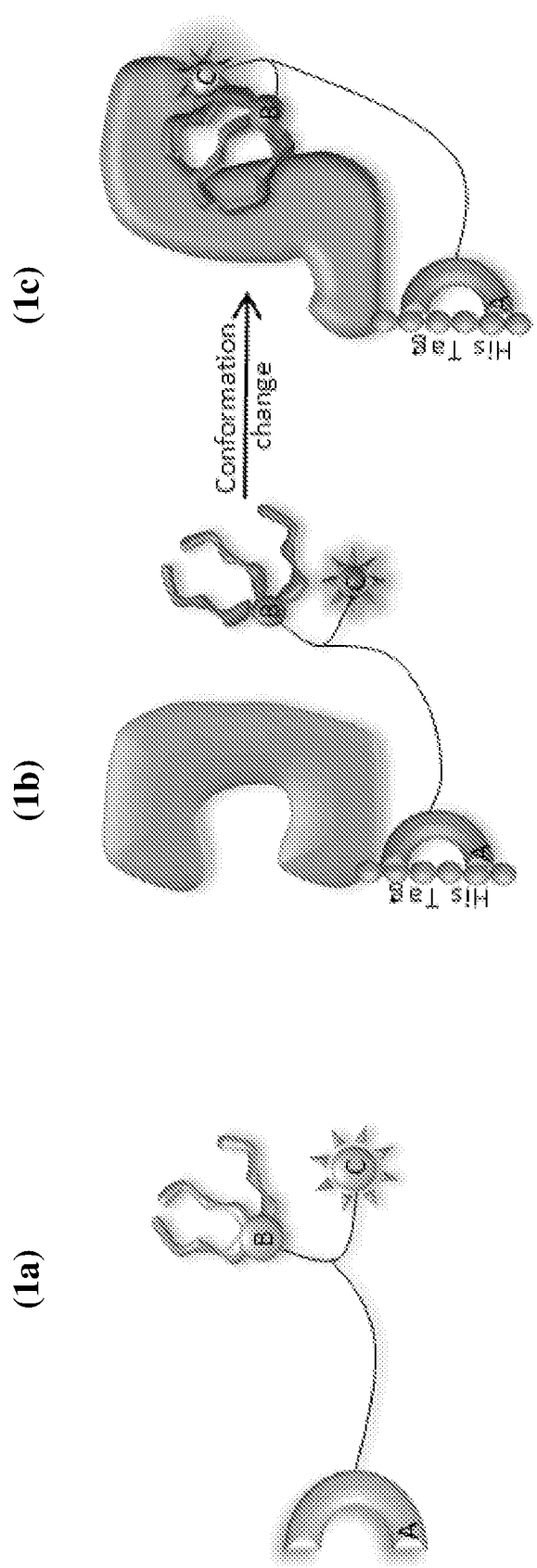
FIG. 1 depicts the design principles of sensors for detecting 3D changes on a protein surface according to this invention. (a): The sensor contains three components: A: A genetically targeted molecule. B: A non-selective protein surface binder. C: A solvatochromic fluorophore. (b) and (c): Preferential binding of the surface receptor (B) to the protein in one of its conformational states (c) induces a change in the fluorescence signal.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The design of targeted protein surface sensors is based on an approach for enhancing the potency of synthetic protein surface receptors. Specifically, it has been previously shown that when attached to selective protein binders, these receptors exhibit much higher affinity and selectivity toward the surfaces of their protein targets. In this study, this approach is taken a step further and it is demonstrated how it can be used to create compounds, which are fluorescent molecular sensors that respond to dynamic changes that occur on the surfaces of His-tag-labeled proteins. It is further described how combination of flexible linker with a modifiable synthetic receptor enables the design of various compounds that target different regions on the surface of various proteins, and can be used as sensors for tracking protein surface changes.

In one embodiment, this invention is directed to a compound that responds to changes that occur on the surface of a specific protein. In another embodiment, the compound is monomolecular. In another embodiment, the monomolecular compound is a sensor. In another embodiment, the sensor is appended with distinct protein recognition motifs: selective and non-selective. In another embodiment, the compound does not comprise oligonucleotides. In another embodiment, the sensor is a fluorescent sensor that can track changes that occur on the surfaces of a specific protein. In another embodiment the protein is not a homodimer. In another embodiment the protein is labeled with a polypeptide tag. In another embodiment the protein is labeled with a polyhistidine tag (His-tag).

In one embodiment, a "polyhistidine tag" (His-tag) according to this invention comprises at least 2, at least 3, at least 4, at least 5, at least 6, at least 7, at least 8, at least 9, at least 10 histidine residues. In one embodiment, a protein of interest (POI) comprises a polyhistidine tag of this invention, at its N-terminus. In another embodiment, a protein of interest (POI) comprises a polyhistidine tag of this invention, at its C-terminus. In another embodiment, a protein of interest (POI) comprises a polyhistidine tag of this invention, at an internal location of the contiguous amino acid sequence. In another embodiment, the His-tag comprises hexa-histidine peptide (6×His-tag). In another embodiment, the His-tag comprises deca-histidine peptide (10×His-tag).

In another embodiment, this invention is directed to a compound that responds to dynamic changes that occur on the surface of His-tag-labeled proteins. In another embodiment, the protein is any protein known in the art that may be tagged. In another embodiment the protein is calmodulin (CaM), (CaM($Ca^{2+}$)), G protein, or B-cell lymphoma 2 protein (Bcl-2).

The structure of these sensors, which were designed to detect modifications in the surface of proteins, consists of three main components: a genetically targeted section, (a selective binder; e.g., a Tag-binding region) (I), a protein surface receptor (non-selective binder) (II), and a solvatochromic dye (fluorophore) (III). The operating principles of the sensors according to this invention are schematically illustrated in FIG. 1. The genetically targeted section (A) ensures that the sensor will selectively bind a specifically labeled protein (e.g., His-tag labeled protein), regardless of its conformational state. A change in the protein's conformation alters its surface configuration and induces the binding of the protein surface receptor (B). Changes in local environment of the solvatochromic fluorophore (C) lead to the generation of a distinct emission signal. Importantly, through an appropriate choice of protein surface receptors, this approach can be used to track various changes on the surfaces of proteins including a wide range of post-translational modifications (PTMs).

In one embodiment, this invention is directed to a compound that can track changes that occur on the surfaces of a specific protein, said compound comprises:
 a. a selective binder;
 b. a non-selective binder; and
 c. a fluorophore.

In another embodiment, the compound is a monomolecular compound. In another embodiment, the monomolecular compound is a sensor for detecting 3D changes on a protein surface. In another embodiment, the selective binder is a Tag-binding region.

A "Tag binding region" refers to any compound, molecular group, or molecular moiety that can specifically bind with high affinity to a specified peptide motif (i.e., a specific peptide sequence genetically grafted onto a recombinant protein). Non limiting examples for tag binding regions are: FlAsH (for TC tag), ReAsH (for TC tag), Ni-nitrilotriacetic acid (Ni-NTA), bis Ni-NTA, tris-Ni NTA (for His-tag), etc.

It was decided to first target the most common affinity tag (His-tag) in order to demonstrate the generality of the approach. However, other molecules of this class that can target different types of fusion peptides could also be used as selective binders.

This approach thus circumvents the challenge of selectively recognizing protein surfaces with synthetic agents by bringing a relatively weak and non-selective protein surface receptor (non-selective binder) in the vicinity of the protein of interest (POI). In this way, an intermolecular synthetic receptor-protein interaction becomes intramolecular, which increases the effective molarity of the system and therefore, the receptor's affinity and specificity. This key principle distinguishes such sensors from other probes that can track protein (e.g. CaM) conformational changes or binding interactions, by labeling the protein (e.g. CaM) at specific positions that are sensitive to altered distances between its termini, or by labeling its binding partners, respectively. Here, the combination of a flexible linker with a modifiable synthetic receptor should enable one to design sensor compounds that match different regions on the surfaces of various proteins.

A unique property of the sensors of this invention is that they bind their targets using a dual interaction mode: selective and non-selective. This combination circumvents the need to design a highly specific receptor for the protein's surface or to use natural binding partners (e.g., antibodies, proteins, and peptides) that selectively bind the desired modification. In addition, using this approach the protein does not have to be fluorescently labeled at particular positions, or undergo a significant conformational change.

In one embodiment, this invention is directed to a sensor that can track changes that occur on the surfaces of a specific protein, said sensor comprises:
 a. a selective binder;
 b. a non-selective binder; and
 c. a fluorophore.

The "selective binder" is any compound or derivative that can binds particular protein or protein groups with high affinity and selectivity. In another embodiment, the selective binder is a synthetic inhibitor, a natural ligand or an aptamer that is selective toward a specific protein group, but also broad spectrum which binds particular protein groups with high affinity and selectivity. In another embodiment, the selective protein binder of this invention is any selective protein binder known in the art. In another embodiment, a selective binder is any molecule that can target different type of fusion proteins that contain certain protein tags such as: a polyhistidine tag, (e.g., 6×His-tag, 10×His-tag), tetra cysteine peptide (CCPGCC, TC tag), etc. A "protein tag" refers herein to a peptide sequence genetically grafted onto a recombinant protein. Protein tags include but not limited to: a His-tag, FLAG tag, HA tag, C-myc tag, AviTag, Calmodulin-tag, polyglutamate tag, E-tag, Myc-tag, S-tag, SBP-tag, Softag, Strep-tag, TC tag, V5 tag, VSV-tag, Xpress tag, etc. In one embodiment, the selective binder comprises a "Tag-binding region". In another embodiment, the selective binder is a targeted protein receptor comprising a protein tag binder. In one embodiment, the selective binder comprises a His-tag binder. In another embodiment, the selective binder of this invention comprises Ni-nitrilotriacetic acid (Ni-NTA), bis-Ni-NTA, or Iris-Ni-NTA. In another embodiment, the selective binder of this invention comprises a derivative of Ni-nitrilotriacetic acid (Ni-NTA), bis-Ni-NTA, or tris-Ni-NTA, wherein the term "derivative" includes but not limited to alkyl derivatives, amide derivatives, carboxy derivatives, and the like.

A "non-selective binder" which can also be referred to herein as a "protein surface receptor", is a functionalized amino acid sequence or peptide groups that react non-selectively, with complementary protein surfaces based on their size, topology and electrostatic potential. By systematically modifying the non-selective binder's sequence and length one can obtain a library of protein surface binders with distinct physicochemical properties. In one embodiment, the non-selective protein surface binder is a relatively weak binder that varies among the different receptors. In another embodiment, the non-selective binder contains a tripodal peptide group with a large surface area of 750-1500 $A^{o2}$, typical for synthetic protein surface receptors and protein-protein interaction. Each non-selective binder (e.g. tripodal peptide) is expected to interact differently with the surfaces of distinct proteins of interest (POI). In another embodiment, the non-selective protein surface binder is a peptide. In another embodiment, the non-selective protein surface binder comprises at least one peptide. In another embodiment, the non-selective protein surface binder comprises three peptides. In another embodiment, the non-selective protein surface binder is a tripodal peptides having a surface of 750-1500 Å$^2$. In one embodiment, the non-selective binder comprises at least one hydrophobic peptide (e.g. SEQ ID No. 1). In another embodiment, the non-selective binder comprises at least one negatively charged peptide (e.g., SEQ ID No. 2). In another embodiment, the non-selective binder comprises at least one polar peptide (e.g., SEQ ID No. 3). In another embodiment, the non-selective binder comprises at least one positively charged peptide (e.g., SEQ ID No. 4). In another embodiment, the non-selective binder comprises at least one peptide consisting of positively charged and hydrophobic amino acids (e.g., SEQ ID No. 5). In another embodiment, the non-selective binder comprises at least one peptide consisting of negatively charged and hydrophobic amino acids. In another embodiment, the non-selective binder comprises at least one peptide consisting of polar and hydrophobic amino acids. In another embodiment, the non-selective binder comprises at least one peptide consisting of negatively charged and polar amino acids. In another embodiment, the non-selective binder comprises at least one peptide consisting of positively charged and polar amino acids. In another embodiment, the non-selective binder comprises at least one peptide as listed in FIG. 14 and Table 1.

In some embodiments, the "fluorophore" of this invention comprises a solvatochromic dye. In one embodiment, the solvatochromic dye comprises dansyl, fluorescein (6-FAM), FAM, cyanine dyes (e.g. Cy3, Cy5), sulfoindocyanine, nile red, rhodamine, perylene, fluorenyl, coumarin, 7-methoxycoumarin (Mca), dabcyl, NBD, Nile blue, Tamra, BODIPY or derivative thereof. In some embodiments, the solvatochromic dye of this invention is dansyl.

In another embodiment, the sensor further comprises a linker which covalently links between the selective binder and the non-selective binder. In another embodiment, the linker is further covalently attached to the fluorophore. In another embodiment, the fluorophore is attached to the linker in the vicinity of the non-selective binder.

In another embodiment, the linker is hydrophilic linker. In another embodiment, the linker is flexible linker. In another embodiment, the linker is flexible hydrophilic linker. In another embodiment, the linker is a polyethylene glycol (PEG) derivative. In another embodiment, the linker comprises a polyethylene glycol (PEG) moiety. In another embodiment, the linker is a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof.

In one embodiment, this invention is directed to a compound that can track changes that occur on the surfaces of a specific protein, said compound comprises:
  a. a selective binder;
  b. a non-selective binder;
  c. a fluorophore; and
  d. a linker which covalently links between the selective binder and the non-selective binder.

In another embodiment, the compound is a monomolecular compound. In another embodiment, the monomolecular compound is a sensor for detecting 3D changes on a protein surface. In another embodiment, the selective binder is a Tag-binding region.

In one embodiment, this invention is directed to a compound for tracking changes that occur on the surface of a tagged proteins. In another embodiment, the compound comprises a Tag-binding region.

A "tagged-protein" refers to a recombinant protein onto which the specified peptide motif is grafted. Non limiting examples for protein Tags are: His-tag, FLAG tag, HA tag, C-myc tag, AviTag, Calmodulin-tag, polyglutamate tag, E-tag, Myc-tag, S-tag, SBP-tag, Softag, Strep-tag, TC tag, V5 tag, VSV-tag, Xpress tag, etc.

In another embodiment, this invention is directed to a compound that can track changes that occur on the surface of a tagged-protein, said compound comprises:
  a. a selective Tag-binding region;
  b. a non-selective binder; and
  c. a fluorophore.

In another embodiment, the compound is a monomolecular compound. In another embodiment, the monomolecular compound is a sensor for detecting 3D changes on a tagged-protein surface. In another embodiment, the tagged-protein is a His-tagged protein. In another embodiment, the Tag-binding region comprises Ni-nitrilotriacetic acid (Ni-NTA) groups (i.e., mono-Ni-NTA, bis-Ni-NTA, or tris-NiNTA). In another embodiment, the Tag-binding region comprises three NiNTA groups (tris-Ni-NTA).

Figure 2:
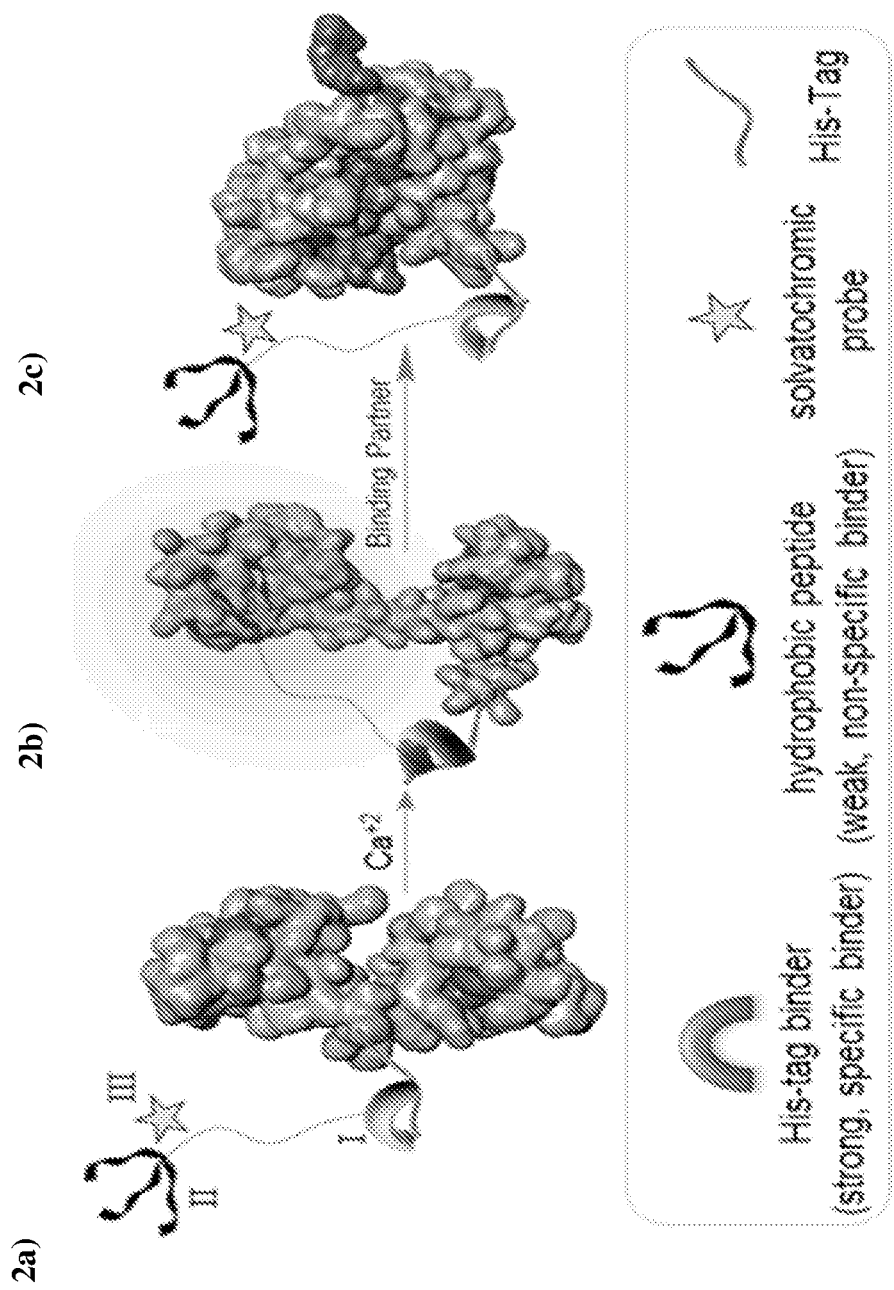
FIG. 2 depicts the operating principles of a targeted protein surface sensor consisting of a His-tag binder (I), a protein surface receptor (II), and a solvatochromic probe (III). The binding of calcium ions to His-CaM (a) promotes the exposure of a hydrophobic cleft on the surface of His-CaM($Ca^{+2}$) and a consequent interaction with the sensor's hydrophobic receptor (b). Changes in the molecular environment of the solvatochromic probe result in enhanced emission. A binding partner, such as the M13 peptide, can also be sensed by the system owing to the formation of a His-CaM($Ca^{+2}$)-M13 complex (c), which triggers the release of the protein-bound receptor.

There are two main limitations of existing genetically targeted molecules and sensors. The first limitation is the lack of a simple and easily applicable method for targeting His-tags, which are most prevalent genetically fused peptide motifs. The second limitation is the inability of such sensors to track changes that occur on the surfaces of proteins. These limitations are circumvented by the development of (1) a universal building block for preparing various His-tag-binders and sensors as described herein below. In the following step (2) the His-tag binder is attached to a protein surface receptor, and the resulting sensor (FIG. 1) can track changes that occur on the surfaces of proteins, e.g. the exposure of a hydrophobic cleft resulting from the binding of calmodulin (CaM) to calcium ions (FIG. 2). This is the first method that enables tracking changes on the surfaces of specific proteins using fluorescent molecular sensors and hence, this invention could lead to the realization of various other sensors that can track important post-translational modifications.

In one embodiment, this invention is directed to a compound for tracking changes that occur on the surface of a His-tag labeled protein.

In another embodiment, this invention is directed to a compound that can track changes that occur on the surfaces of a His-tagged protein, said compound comprises:
  a. a His-tag binder;
  b. a non-selective binder; and
  c. a fluorophore.

In another embodiment, the compound is a monomolecular compound. In another embodiment, the monomolecular compound is a sensor for detecting 3D changes on a His-tag labeled protein surface.

The first component of the sensor (I), is a His-tag binder. The His-tag binder is a synthetic agent that can selectively bind to a polyhistidine tag fused to the POI (e.g., 6×His-tag, 10×His-tag). The role of this binder is to ensure that the sensor will bind to the His-tagged POI with high affinity and selectivity (FIG. 2, state a). The second component of the sensor (II) is a branched peptide receptor, whose sequence and length can be adjusted to obtain preferential affinity toward a specific domain on the protein's surface. In the exemplary case of His-tagged Calmodulin (His-CaM), this receptor should consist of a hydrophobic peptide that matches the exposed hydrophobic region on His-CaM ($Ca^{+2}$).

The third part of the sensor (III) is an environmentally sensitive fluorophore introduced in the vicinity of the receptor, which should enable the system to fluoresce when the receptor binds the solvent-exposed hydrophobic patch (FIG. 2, State b). This fluorescence should be eliminated in the presence of a binding partner, which interacts with this region and displaces the protein-surface receptor (FIG. 2, state c).

Considering that a polyhistidine peptide (His-tag) is the most common affinity tag and that high-throughput methodologies for sensing protein modifications and binding interactions are needed, it is believed that by choosing appropriate recognition elements and by systematically modifying the receptors' structures, various protein surfaces could be detected by using the technology of this invention. Accordingly, the approach presented here is general, and by systematically screening various peptide sequences, one can, in principle, identify a wide range of protein surface binders and use them to track diverse protein structural modifications such as post-translational modifications (PTMs).

By selecting, in one embodiment, His-tagged CaM as a protein target, it is herein demonstrated how this approach could be used to track protein surface modifications that result from structural changes or binding interactions. In addition, it is shown in another embodiment, how such sensors could be further applied to detect dephosphorylating of an unlabeled calmodulin-dependent protein kinase II (CaMKII), as well as, in another embodiment, sense the interaction between the His-tagged B cell 2 lymphoma protein and its natural binder Bax (His-Bcl-2-Bax).

Non-Selective Protein Surface Binder ("Non-Selective Binder") of Sensors of the Invention.

In one embodiment, this invention is directed to a sensor that can track changes that occur on the surface of a protein, said sensor comprises a selective binder, a non-selective binder and a fluorophore.

In one embodiment, the non-selective binder is a relatively weak binder that varies among the different receptors. In one embodiment, the non-selective protein surface binder is a branched peptide receptor, whose sequence and length can be adjusted to obtain preferential affinity towards a specific domain on the protein of interest (POI)'s surface. In another embodiment, the non-selective binder contains a tripodal peptide group with a large surface area of 750-1500 $Å^{o2}$, typical for synthetic protein surface receptors and protein-protein interaction. Each non-selective binder (e.g. tripodal peptide) is expected to interact differently with the surfaces of distinct proteins of interest (POI).

In one embodiment, the non-selective binder, of the sensor according to this invention, comprises a peptide tripod, represented by the structure of formula A:

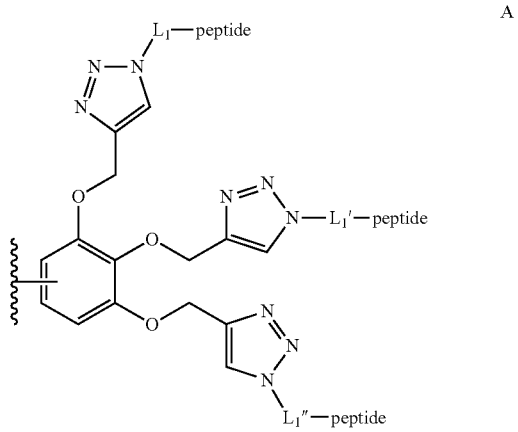

wherein each of $L_1$, $L_1'$ and $L_1''$ is independently a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof; and wherein the peptide comprises any 2-20 amino acid peptide (hydrophobic, polar, charged or combination thereof).

In one embodiment, the non-selective protein surface binder of the sensor according to this invention comprises a peptide tripod, represented by the structure of formula B:

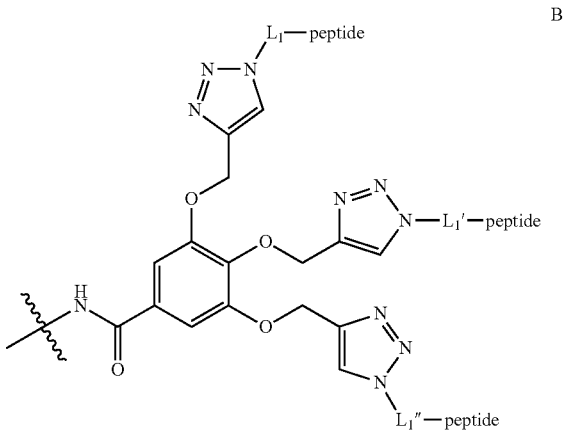

wherein $L_1$, $L_1'$ and $L_1''$ and "peptide" are as defined above.

In some embodiments the non-selective protein surface binder of the sensor according to this invention comprises a tripod molecule represented the structure of formula C:

C

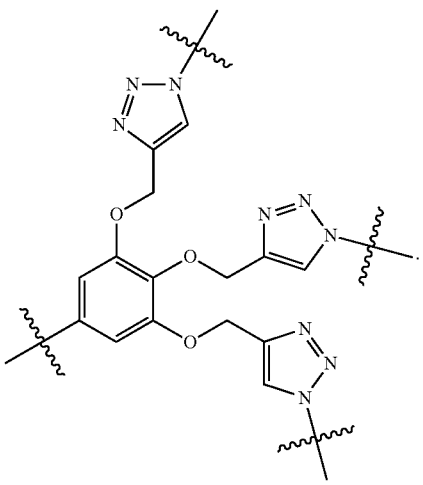

In another embodiment, each of $L_1$, $L_1'$ and $L_1''$ of formula (A) and/or (B) is independently a linear alkyl chain of 2-10 carbon atoms. In another embodiment, each of $L_1$, $L_1'$ and $L_1''$ is n-propyl.

In another embodiment, the peptides comprised in the non-selective binder and in formula (A) and/or (B) possess between 2 to 30 amino acid sequences. In another embodiment, the peptides possess between 4 to 15 amino acid sequences. In another embodiment, the peptides possess between 2 to 20 amino acid sequences. In another embodiment, the peptides possess between 3 to 10 amino acid sequences. In another embodiment, the peptide comprises between 3 to 8 amino acids. In another embodiment, the peptides are the same. In another embodiment, the peptides are different. In another embodiment, the peptides comprise hydrophobic amino acids. In another embodiment, the peptide is SEQ ID No. 1. In another embodiment, the peptides comprise polar amino acids. In another embodiment, the peptide is SEQ ID No. 3. In another embodiment, the peptides comprise negatively charged amino acids. In another embodiment, the peptide is SEQ ID No. 2. In another embodiment, the peptides comprise positively charged amino acids. In another embodiment, the peptide is SEQ ID No. 4. In another embodiment, the peptides comprise combination of hydrophobic and negatively charged amino acids. In another embodiment, the peptides comprise combination of hydrophobic and positively charged amino acids. In another embodiment, the peptide is SEQ ID No. 5. In another embodiment, the peptides comprise combination of hydrophobic and polar amino acids. In another embodiment, the peptides comprise combination of polar and negatively charged amino acids. In another embodiment, the peptides comprise combination of polar and positively charged amino acids. In another embodiment the peptides are as described in Table 1, 1A and FIG. 14.

In another embodiment the peptide includes amino acid sequence interrupted by a solvatochromic dye. In another embodiment the peptide includes amino acid sequence, wherein one of the amino acids is substituted with a solvatochromic dye. In another embodiment, the solvatochromic dye is covalently bonded to a lysine residue (K). In another embodiment, the solvatochromic dye is covalently bonded to the backbone of the peptide tripod of formula (A) and/or (B). In another embodiment, the solvatochromic dye is covalently bonded to the linker, which covalently links between the selective, and the non-selective binders. In another embodiment, the solvatochromic dye is covalently bonded to the linker, in the vicinity of the non-selective binder.

According to this invention, the phrase "in the vicinity of the non-selective binder" refers to a distance between the dye and the non-selective binder that is shorter than the distance between the dye and the selective binder. In one embodiment, the distance between the dye and the non-selective binder is less than 15 Å; or in another embodiment, less than 10 Å; or in another embodiment, less than 5 Å; wherein the distance is calculated between the dye atom that is attached to the linker and the non-selective binder aryl ring.

Selective Protein Binder of Sensors of the Invention.

In one embodiment, this invention is directed to a sensor that can track changes that occur on the surface of proteins, said sensor comprises a selective binder, a non-selective binder and a fluorophore.

A selective protein binder is referred in this invention to an aptamer, a natural ligand, a synthetic group, or a peptide which binds a specific protein with high affinity and selectivity.

In some embodiments the sensor of this invention comprises at least one selective protein binder. In another embodiment, the selective protein binder of this invention is any selective protein binder known in the art.

In another embodiment, the selective protein binder is marimastat, ethacrynic acid, bisethacrynic acid, complexed nitrilotriacetic acid (NTA), complexed bis NTA, complexed tris-NTA, Ni-nitrilotriacetic acid (Ni-NTA), bis Ni-NTA, tris-Ni NTA, PDGF-BB, heparin, FGF aptamer, estrogen, DNA aptamer, RNA aptamer, peptide aldehyde, estrogen, suberoylanilidehydroxamic acid (SAHA), or a peptide binder. In another embodiment, the complexed NTA, complexed bis-NTA, complexed tris NTA is a nickel or cobalt complex.

In another embodiment, a selective binder comprises a Tag-binding region.

In another embodiment, a selective binder is any molecule that can target different type of affinity tags, such as polyhistidine peptide (HHHHHH, His-tag), or tetra cysteine peptide (CCPGCC, TC tag). In another embodiment, the selective binder is FlAsH probe. In another embodiment, the selective binder is ReAsH probe.

In one embodiment, the selective binder is a His-tag binder. In another embodiment, the selective protein binder of this invention comprises Ni-nitrilotriacetic acid (Ni-NTA), bis-Ni-NTA, or tris-Ni-NTA. In another embodiment, the selective protein binder of this invention comprises a derivative of Ni-nitrilotriacetic acid (Ni-NTA), bis-Ni-NTA, or tris-Ni-NTA, wherein the term "derivative" includes but not limited to alkyl derivatives, amide derivatives, amine derivatives, carboxy derivatives, and the like. In another embodiment, the His-Tag binder comprises a derivative of tris-Ni-nitrilotriacetic acid (tris-Ni-NTA). In another embodiment, a derivative of bis-Ni-nitrilotriacetic acid (bis-Ni-NTA). In another embodiment, a derivative of mono-Ni-nitrilotriacetic acid (Ni-NTA). In another embodiment, the His-tag binder is any monomolecular compound which comprises three Ni-NTA moieties (i.e., tris-Ni-NTA).

In one embodiment, the His-tag binder comprised in the sensor of the invention is represented by the structure of formula D:

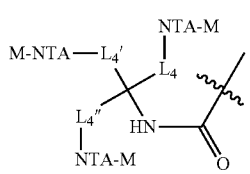

wherein each of $L_4$, $L_4'$, and $L_4''$ is independently a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof; and M is a metal ion.

In one embodiment, M is cobalt (Co). In another embodiment, M is nickel (Ni). In another embodiment, M is Ni(II). In another embodiment, M is Co(II). In another embodiment, M is Co(III). In another embodiment, each of $L_4$, $L_4'$, and $L_4''$ is independently a combination of alkyl ether and alkyl amide (i.e., alkylether-alkylamide). In another embodiment, each of $L_4$, $L_4'$, and $L_4''$ is independently $-(CH_2)_n-NHCO-(CH_2)_m-O-(CH_2)_l-$, wherein n, m and l are each independently an integer between 1 and 6. In another embodiment, n is 4, m is 2 and l is 1. In another embodiment, each of $L_4$, $L_4'$, and $L_4''$ is $-(CH_2)_4-NHCO-(CH_2)_2-O-CH_2-$. In another embodiment, each of $L_4$, $L_4'$, and $L_4''$ is represented by the following structure:

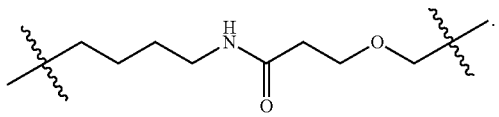 [SMILES: *CCCCNC(=O)CCOC*]

In another embodiment, the His-tag binder comprised in the sensor of the invention is represented by the structure of formula D(a):

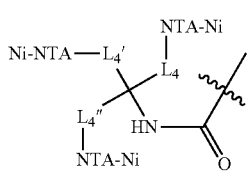

wherein each of $L_4$, $L_4'$, and $L_4''$ is independently a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof.

In another embodiment, each of $L_4$, $L_4'$, and $L_4''$ is independently is a combination of alkyl ether and alkyl amide (i.e., alkylether-alkylamide). In another embodiment, each of $L_4$, $L_4'$, and $L_4''$ is independently $-(CH_2)_n-NHCO-(CH_2)_m-O-(CH_2)_l-$, wherein n, m and l are each independently an integer between 1 and 6. In another embodiment, n is 4, m is 2 and l is 1. In another embodiment, each of $L_4$, $L_4'$, and $L_4''$ is $-(CH_2)_4-NHCO-(CH_2)_2-O-CH_2-$. In another embodiment, each of $L_4$, $L_4'$, and $L_4''$ is represented by the following structure:

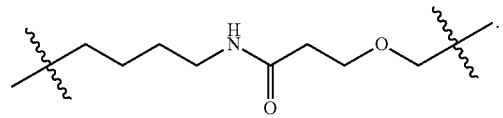 [SMILES: *CCCCNC(=O)CCOC*]

In another embodiment, the His-tag binder comprised in the sensor of the invention is represented by the structure of formula E:

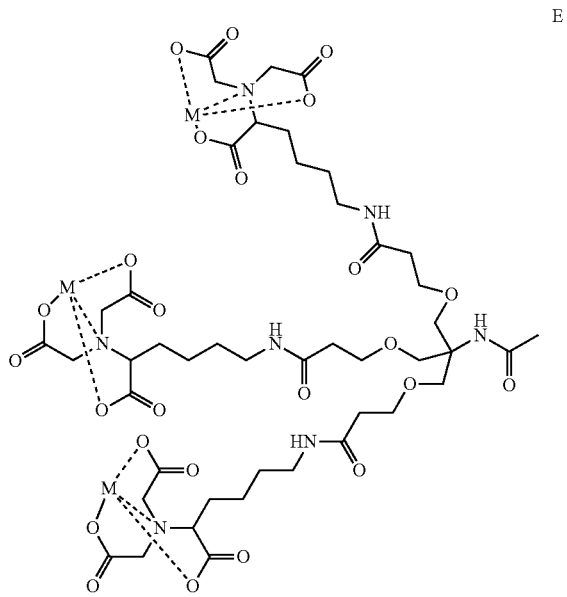

wherein M is a metal ion.

In one embodiment, M is cobalt (Co). In another embodiment, M is nickel (Ni). In another embodiment, M is Ni(II). In another embodiment, M is Co(II). In another embodiment, M is Co(III).

In another embodiment, the His-tag binder comprised in the sensor of the invention is represented by the structure of formula F:

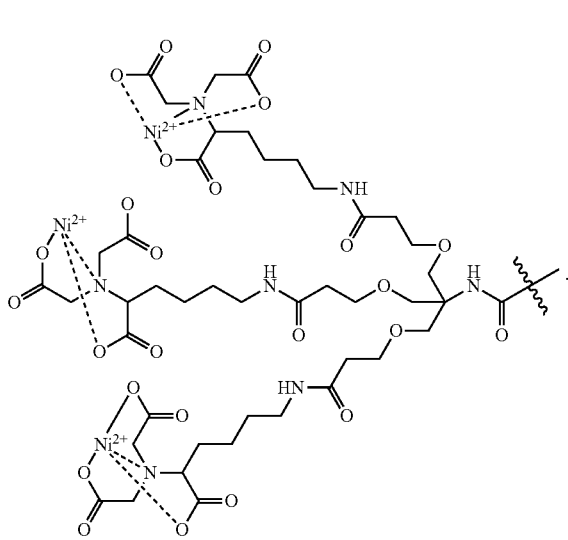

Fluorophore of Sensors of the Invention.

In one embodiment, this invention is directed to a sensor that can track changes that occur on the surface of proteins, said sensor comprises a selective binder, a non-selective binder and a fluorophore.

The fluorophore is an environmentally sensitive probe, introduced in the vicinity of the protein surface receptor, which should enable the system to fluoresce when the protein surface receptor (non-selective binder) binds the POI. This fluorescence should be eliminated in the presence of a binding partner, which either interacts with this region and displaces the protein-bound surface receptor, or induces a conformational change in the protein, which results in the dissociation of the protein surface receptor.

Accordingly, and in one embodiment, the sensor is labeled with a fluorophore, which may be attached directly to the non-selective binder or in the vicinity of it. In one embodiment, the fluorophore is covalently attached directly to the non-selective binder. In another embodiment, the fluorophore is covalently attached to the linker, which covalently links the selective binder with the non-selective binder. In another embodiment, the fluorophore is covalently attached to the linker, in the vicinity of the non-selective binder. In another embodiment, the fluorophore is covalently attached to the linker, in a position that is closer to the non-selective binder than to the selective binder.

In some embodiments, the fluorophore of this invention is a solvatochromic dye. Solvatochromic fluorophores display sensitivity to the polarity of the local environment. These molecules exhibit a low quantum yield in aqueous solution, but become highly fluorescent in nonpolar solvents or when bound to hydrophobic sites in proteins or membranes. In certain embodiments, solvatochromic fluorophores include 2-propionyl-6-dimethylaminonaphthalene (PRODAN) (Weber et al. *Biochemistry* 1979, 18, 3075-3078; Cohen et al. *Science* 2002, 296, 1700-1703), 4-dimethylamino phthalimide (4-DMAP) (Saroja et al. *J. Fluoresc.* 1998, 8, 405-410), and 4-amino-1,8-naphthalimide derivatives (Grabchev et al. *J. Photochem. Photobiol., A* 2003, 158, 37-43; Martin et al. *J. Lumin.* 1996, 68, 157-146). In another embodiment, the solvatochromic dye is dansyl, fluorescein (6-FAM), FAM, cyanine dyes (e.g. Cy3, Cy5), sulfoindocyanine, nile red, rhodamine, perylene, fluorenyl, coumarin, 7-methoxycoumarin (Mca), dabcyl, NBD, Nile blue, Tamra, BODIPY or derivative thereof. In some embodiments, the solvatochromic dye of this invention is dansyl. In another embodiment, the fluorophore is dansyl.

In some embodiments, the fluorophore of this invention is a fluorescent dye. In another embodiment, the fluorescent dye is substituted or unsubstituted anthracene; substituted or unsubstituted nile red; substituted or unsubstituted dansyl; substituted or unsubstituted fluorenyl; substituted or unsubstituted naphthalene; substituted or unsubstituted tetracene; substituted or unsubstituted perylene; substituted or unsubstituted pyrene substituted or unsubstituted fluorescein; substituted or unsubstituted rhodamine; substituted or unsubstituted cyanine, substituted or unsubstituted coumarin; substituted or unsubstituted NBD; substituted or unsubstituted Nile blue; substituted or unsubstituted Tamra; substituted or unsubstituted BODIPY; or any other fluorescent dye known in the art and/or disclosed in http://www.fluorophores.org which is incorporated herein by reference. In another embodiment, the fluorescent dye of this invention is anthracene, naphthalene, fluorenyl, dansyl, nile red, fluorescein, rhodamine, perylene, cyanine, Cy3, Cy5, coumarin, NBD, Nile blue, Tamra, BODIPY, derivative thereof, or combination thereof. In another embodiment, the fluorescent dye of this invention is substituted by one to three substituents. In another embodiment the fluorescent dye is substituted by alkyl, alkenyl, haloalkyl, aryl, O-aryl, —($CH_2$)n-aryl, cycloalkyl, O-cycloalkyl, $CF_3$, F, I, Br, Cl, $NO_2$, CN, $N(Z)_2$, COOH, CO—Z, NHCOZ, CONHZ, ($CH_2$)$NH_2$, ($CH_2$)NH—Z, S—Z, SH, O—Z, ($CH_2$)OH, ($CH_2$)COOH, or OH; wherein Z is H, alkyl, haloalkyl, dihaloalkyl, trihaloalkyl, aryl, phenyl or halogen and n is between 0 and 8. In another embodiment n is between 1 and 6.

In another embodiment, the fluorophore is attached to the non-selective binder of said sensor. In another embodiment, the fluorophore is in the vicinity of the non-selective binder of said sensor. In another embodiment, the fluorophore is attached to the linker of said sensor.

Linker of Sensors of the Invention.

In one embodiment, this invention is directed to a sensor that can track changes that occur on the surface of proteins, said sensor comprises a selective binder, a non-selective binder and a fluorophore. In another embodiment, the sensor further comprises a linker that covalently links the selective binder and the non-selective binder. In another embodiment, the fluorophore is attached to the linker.

In another embodiment, the linker is hydrophilic linker. In another embodiment, the linker is flexible linker. In another embodiment, the linker is flexible hydrophilic linker. In another embodiment, the linker is a polyethylene glycol (PEG) derivative, wherein the term "derivative" includes but not limited to alkyl derivatives, amine derivatives, amide derivatives, carboxy derivatives, and the like. In another embodiment, the linker comprises polyethylene glycol (PEG) moiety. In another embodiment, the linker is a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof. In another embodiment, the linker is a combination of linear or branched alkyl ether chain of 2-50 carbon atoms and substituted linear or branched alkyl diamide chain of 2-50 carbon atoms.

In another embodiment, the linker is represented by the following structure:

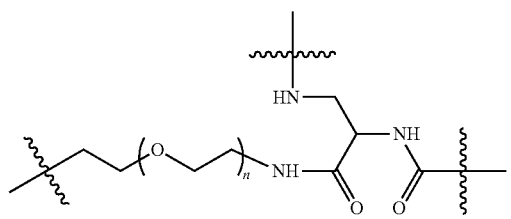

wherein n is an integer number between 1 and 10.
In another embodiment, n is 3.

In another embodiment, the linker is represented by the following structure:

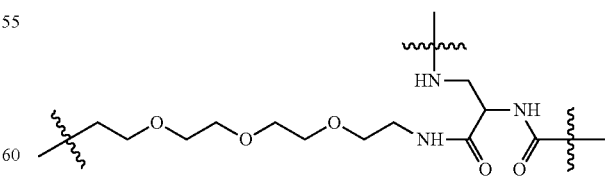

Molecular Structure of Sensors of the Invention.

In one embodiment, this invention is directed to a compound that can track changes that occur on the surface of proteins, said compound comprises a selective binder, a non-selective binder and a fluorophore. In another embodiment, the compound is monomolecular compound. In another embodiment, the monomolecular compound is a sensor for tracking changes that occur on the surface of proteins.

In another embodiment, the sensor is represented by the structure of formula I:

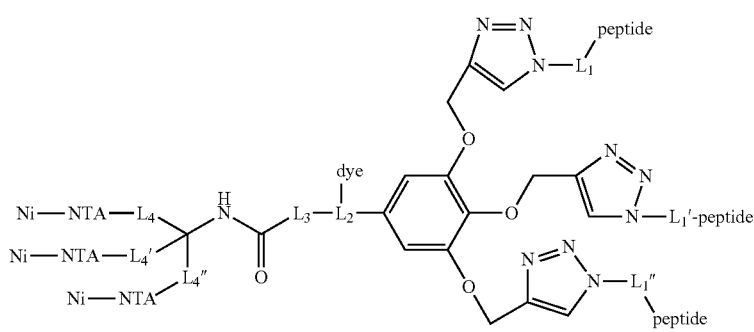

I wherein
each of $L_1$, $L_1'$ and $L_1''$ is independently a first linker, wherein each of said first linker is independently a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof;

$L_2$ is a second linker, wherein said second linker is a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof;

$L_3$ is a third linker, wherein said third linker is a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof;

each of $L_4$, $L_4'$, and $L_4''$ is independently a fourth linker, wherein each of said fourth linkers is a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof;

Ni-NTA is nickel complex of nitrilotriacetic acid, "dye" is solvatochromic dye, e.g. dansyl, and "peptide" is any peptide comprising 2-15 amino acids.

In one embodiment, each of $L_1$, $L_1'$ and $L_1''$ is independently a linear alkyl chain of 2-5 carbon atoms, $L_2$ is a substituted alkyl diamide, $L_3$ is a linear alkylether, and each of $L_4$, $L_4'$, and $L_4''$ is independently a combination of a linear alkyl ether and linear alkyl amide.

In another embodiment, the peptide comprises 3-8 amino acids. In another embodiment, the peptide is a hydrophobic peptide. In another embodiment, the peptide is SEQ ID No. 1. In another embodiment, the peptide comprises both hydrophobic and positively charged amino acids. In another embodiment, the peptide is SEQ ID No. 5. In another embodiment, the peptides are the same. In another embodiment, the peptides are different.

In another embodiment, the sensor is represented by the structure of formula II:

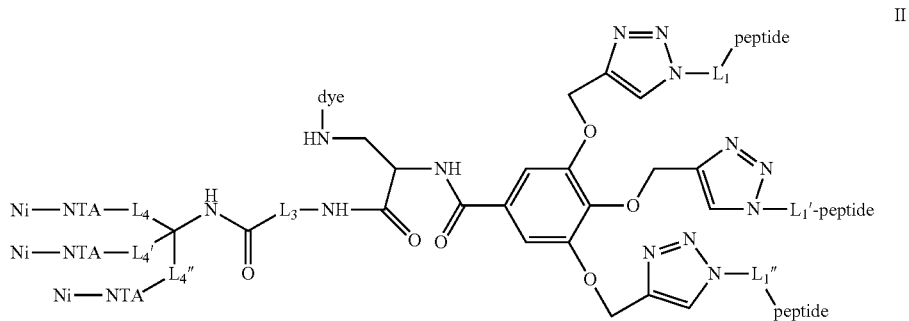

II wherein
each of $L_1$, $L_1'$ and $L_1''$ is independently a first linker, wherein each of said first linker is independently a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof;

pendently combination of a linear alkyl ether and linear alkyl amide of 3-10 carbon atoms (i.e., alkylether-alkylamide).

In another embodiment, the peptide comprises 3-8 amino acids. In another embodiment, the peptide is a hydrophobic peptide. In another embodiment, the peptide is SEQ ID No. 1. In another embodiment, the peptide comprises both hydrophobic and positively charged amino acids. In another embodiment, the peptide is SEQ ID No. 5.

In another embodiment, the sensor is represented by the structure of formula III:

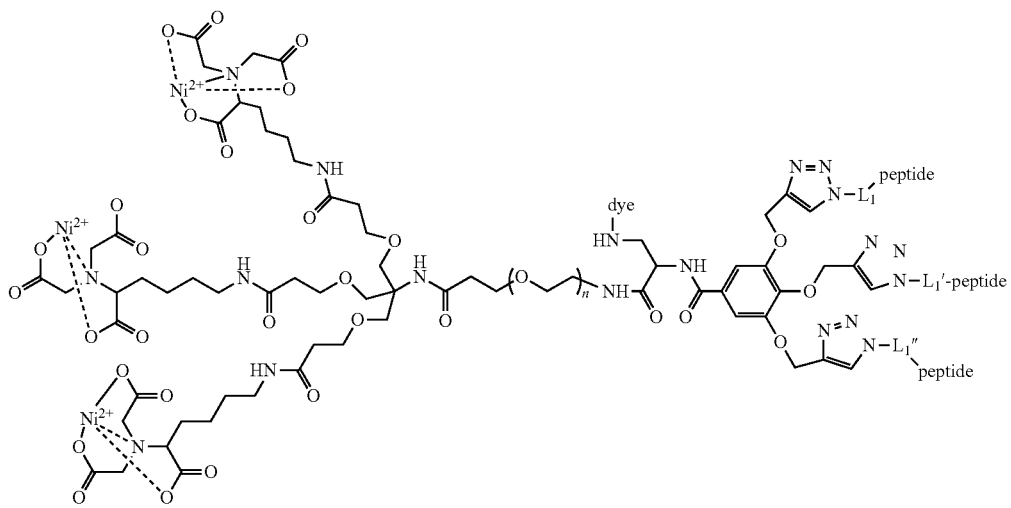

III $L_3$ is a third linker, wherein said third linker is a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof;

each of $L_4$, $L_4'$, and $L_4''$ is independently a fourth linker, wherein each of said fourth linkers is independently a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof;

Ni-NTA is nickel complex of nitrilotriacetic acid, "dye" is solvatochromic dye, e.g. dansyl, and "peptide" is any peptide comprising 2-15 amino acids.

In one embodiment, each of $L_1$, $L_1'$ and $L_1''$ is independently a linear alkyl chain of 2-6 carbon atoms, $L_3$ is polyethylene glycol, and each of $L_4$, $L_4'$, and $L_4''$ is indewherein each of $L_1$, $L_1'$ and $L_1''$ is independently a first linker, wherein each of said first linkers is a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof;

n is an integer number between 1 and 20;

Ni-NTA is nickel complex of nitrilotriacetic acid, "dye" is solvatochromic dye, e.g. dansyl, and "peptide" is any peptide comprising 2-15 amino acids.

In one embodiment, each of $L_1$, $L_1'$ and $L_1''$ is independently a linear alkyl chain of 2-6 carbon atoms. In another embodiment, each of $L_1$, $L_1'$ and $L_1''$ is propyl. In another embodiment, n is 3.

In another embodiment, the peptide comprises 3-8 amino acids. In another embodiment, the peptide is a hydrophobic peptide. In another embodiment, the peptide is SEQ ID No. 1. In another embodiment, the peptide comprises both hydrophobic and positively charged amino acids. In another embodiment, the peptide is SEQ ID No. 5.

In another embodiment, the sensor is represented by the structure of formula IV:

IV

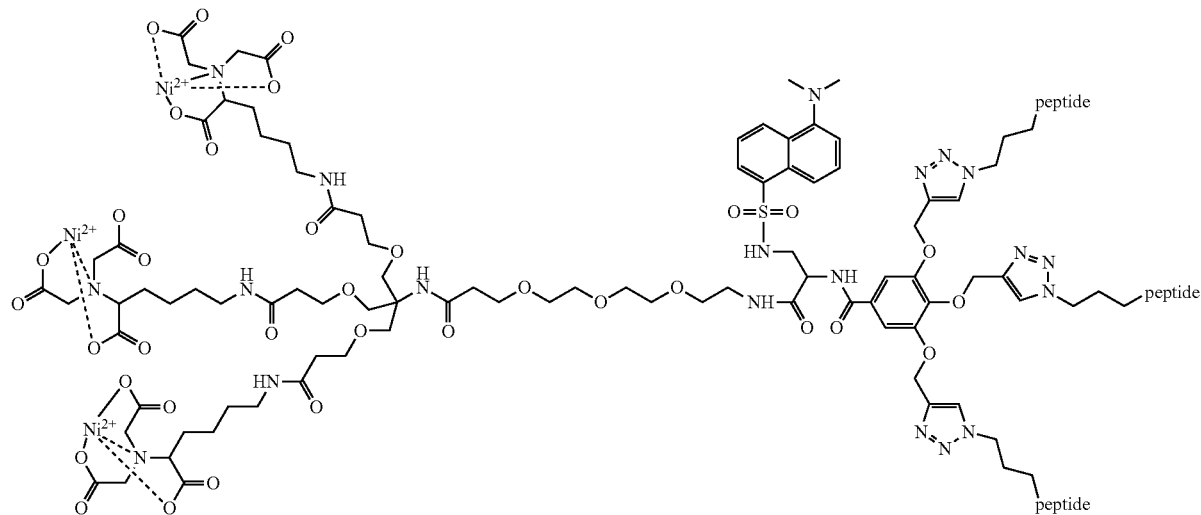

wherein "peptide" can be any peptide comprising 2-20 amino acids.

Universal His-Tag Binding Compounds.

In one embodiment, this invention is directed to a universal building block for preparing various His-tag-binding compounds and genetically targeted sensors.

The His-tag binding compounds (or building block) according to this invention, comprise three nitrilotriacetic acid (NTA) units that can bind the His-tags with low nanomolar affinities (after complexation with nickel (II) or other metal ions) and, most importantly, it also contains an auxiliary unit ($R_1$, as described herein below) that enables one to modify it using a wide range of functionalities. This building block is general for various protein binders and sensors.

This invention is therefore directed to a universal His-tag binding compounds and building blocks that, upon complexation with Ni(II), Co(II), or Co(III) can selectively bind histidine-tags of various labeled proteins with nanomolar affinities. Therefore, the His tag binding compounds and building blocks according to this invention, are useful in the preparation of various genetically targeted probes for various applications as described herein below.

In one embodiment, the His-tag binding compound is represented by the structure of formula X:

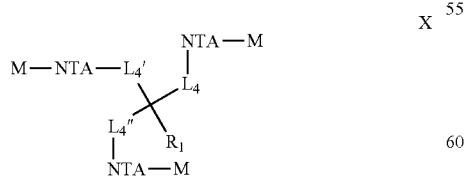

wherein $R_1$ is azide, amine, $C_2$-$C_6$ alkynyl, thioester, disulfide, maleimide, biotin, carboxyl, thiol, triazole, alkylamide, carbamate, or $R_1$ is selected from:

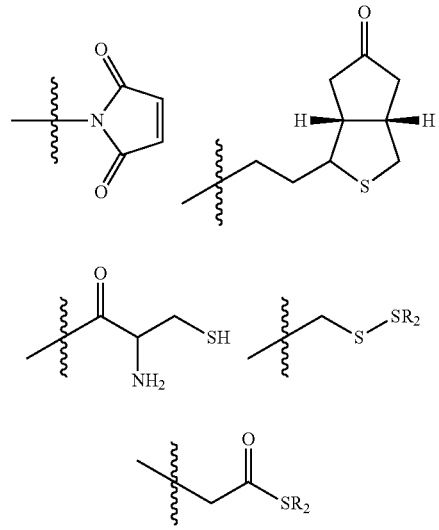

wherein $R_2$ is hydrogen, substituted or unsubstituted linear or branched $C_1$-$C_{12}$ alkyl, substituted or unsubstituted linear or branched $C_1$-$C_{12}$ arylalkyl or benzyl;

each of $L_4$, $L_4'$, and $L_4''$ is independently a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof;

M is a metal ion; and

NTA is nitrilotriacetic acid.

In another embodiment, the His-tag binding compound is represented by the structure of formula X(a):

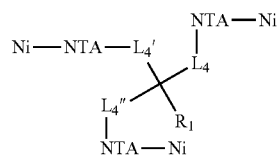

X(a)

wherein $R_1$ is azide, amine, $C_2$-$C_6$ alkynyl, thioester, disulfide, maleimide, biotin, carboxyl, thiol, triazole, alkylamide, carbamate, or $R_1$ is selected from:

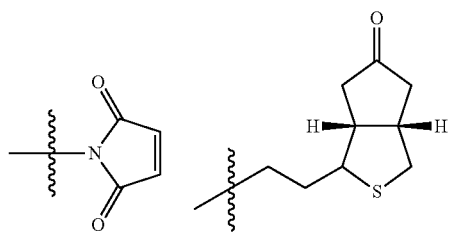

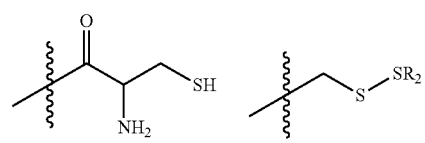

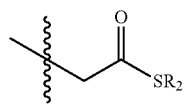

wherein $R_2$ is hydrogen, substituted or unsubstituted linear or branched $C_1$-$C_{12}$ alkyl, substituted or unsubstituted linear or branched $C_1$-$C_{12}$ arylalkyl or benzyl;

each of $L_4$, $L_4'$, and $L_4''$ is independently a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof.

In another embodiment, the His-tag binding compound is represented by the structure of formula XX:

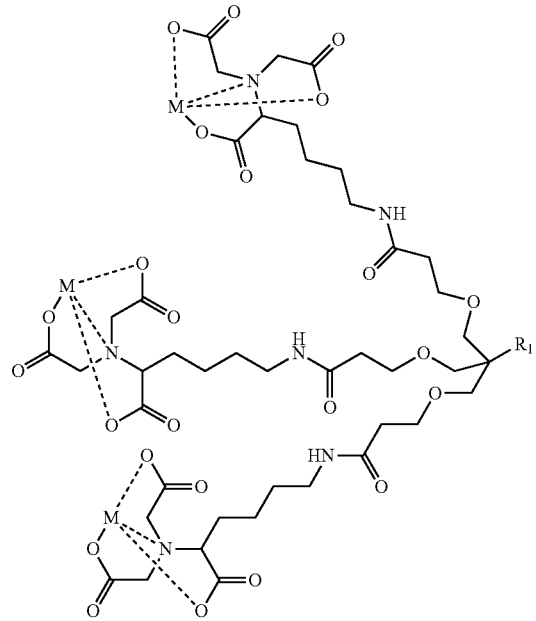

XX wherein $R_1$ is azide, amine, $C_2$-$C_6$ alkynyl, thioester, disulfide, maleimide, biotin, carboxyl, thiol, triazole, alkylamide, carbamate, or $R_1$ is selected from:

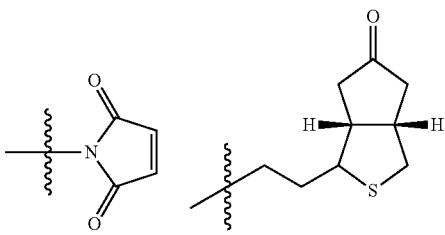

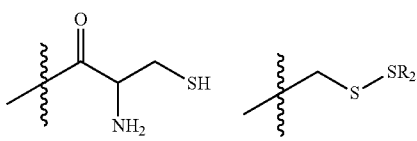

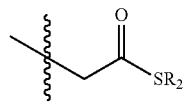

wherein $R_2$ is hydrogen, substituted or unsubstituted linear or branched $C_1$-$C_{12}$ alkyl, substituted or unsubstituted linear or branched $C_1$-$C_{12}$ arylalkyl or benzyl; and M is a metal ion.

In another embodiment, the His-tag binding compound is represented by the structure of formula XX(a):

XX(a)

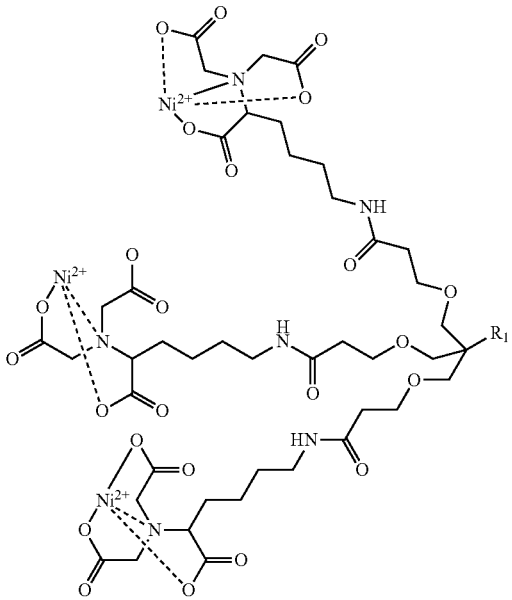

wherein
R$_1$ is azide, amine, C$_2$-C$_6$ alkynyl, thioester, disulfide, maleimide, biotin, carboxyl, thiol, triazole, alkylamide, carbamate, or R$_1$ is selected from:

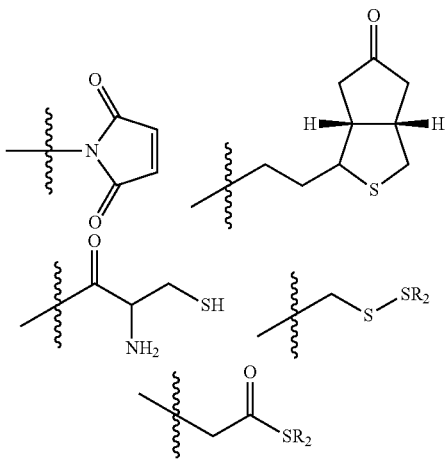

wherein
R$_2$ is hydrogen, substituted or unsubstituted linear or branched C$_1$-C$_{12}$ alkyl, substituted or unsubstituted linear or branched C$_1$-C$_{12}$ arylalkyl or benzyl.

In one embodiment, this invention is directed to a His-tag binding compound of formula X, X(a), XX or XX(a), coupled through the R$_1$ moiety to an oligonucleotide, a peptide, a protein, a small molecule, or any combination thereof. In another embodiment, the oligonucleotide is DNA. In another embodiment, the oligonucleotide is RNA. In another embodiment, the small molecule is a dye. In another embodiment, the small molecule is a solvatochromic dye. In another embodiment, the small molecule is a therapeutically active molecule.

In one embodiment, this invention is directed to a fluorescently tagged His-tag binding compound, comprising the compound of formula X, X(a), XX, or XX(a), wherein said compound is covalently linked to a fluorophore through the R$_1$ moiety.

In one embodiment, this invention is directed to a fluorescently tagged His-tag binding compound, comprising the compound of formula X, X(a), XX, or XX(a), wherein said compound is covalently linked to a fluorophore through a linker, which links between the R$_1$ moiety of said compound and said fluorophore.

In another embodiment, the linker is hydrophilic linker. In another embodiment, the linker is flexible linker. In another embodiment, the linker is flexible hydrophilic linker. In another embodiment, the linker is a polyethylene glycol (PEG) derivative. In another embodiment, the linker comprises a polyethylene glycol (PEG) moiety. In another embodiment, the linker is a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof.

In another embodiment, the fluorophore is a solvatochromic dye.

Specific Embodiments for Compounds of the Invention

In one embodiment, L$_1$ of formula I, II, III, (A) or (B) is a substituted or unsubstituted linear or branched alkyl chain of 2-50 carbon atoms. In another embodiment, unsubstituted linear alkyl chain of 2-50 carbon atoms. In another embodiment, unsubstituted linear alkyl chain of 2-6 carbon atoms. In another embodiment, L$_1$ is propyl. In another embodiment, L$_1$ is a substituted or unsubstituted linear or branched alkyl ether chain of 2-50 carbon atoms. In another embodiment, substituted or unsubstituted linear or branched alkyl phosphate chain of 2-50 carbon atoms. In another embodiment, substituted or unsubstituted linear or branched alkyl amide chain of 2-50 carbon atoms. In another embodiment, substituted or unsubstituted linear or branched alkyl diamide chain of 2-50 carbon atoms. In another embodiment, substituted or unsubstituted linear or branched alkyl amine chain of 2-50 carbon atoms. In another embodiment, L$_1$ is any combination of substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, and substituted or unsubstituted linear or branched alkyl amine chain of 2-50 carbon atoms.

In one embodiment, L$_1$' of formula I, II, III, (A) or (B) is a substituted or unsubstituted linear or branched alkyl chain of 2-50 carbon atoms. In another embodiment, unsubstituted linear alkyl chain of 2-50 carbon atoms. In another embodiment, unsubstituted linear alkyl chain of 2-6 carbon atoms. In another embodiment, L$_1$' is propyl. In another embodiment, L$_1$' is a substituted or unsubstituted linear or branched alkyl ether chain of 2-50 carbon atoms. In another embodiment, substituted or unsubstituted linear or branched alkyl phosphate chain of 2-50 carbon atoms. In another embodiment, substituted or unsubstituted linear or branched alkyl amide chain of 2-50 carbon atoms. In another embodiment, substituted or unsubstituted linear or branched alkyl diamide chain of 2-50 carbon atoms. In another embodiment, substituted or unsubstituted linear or branched alkyl amine chain of 2-50 carbon atoms. In another embodiment, $L_1'$ is any combination of substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, and substituted or unsubstituted linear or branched alkyl amine chain of 2-50 carbon atoms.

In one embodiment, $L_1''$ of formula I, II, III, (A) or (B) is a substituted or unsubstituted linear or branched alkyl chain of 2-50 carbon atoms. In another embodiment, unsubstituted linear alkyl chain of 2-50 carbon atoms. In another embodiment, unsubstituted linear alkyl chain of 2-6 carbon atoms. In another embodiment, $L_1''$ is propyl. In another embodiment, $L_1''$ is a substituted or unsubstituted linear or branched alkyl ether chain of 2-50 carbon atoms. In another embodiment, substituted or unsubstituted linear or branched alkyl phosphate chain of 2-50 carbon atoms. In another embodiment, substituted or unsubstituted linear or branched alkyl amide chain of 2-50 carbon atoms. In another embodiment, substituted or unsubstituted linear or branched alkyl diamide chain of 2-50 carbon atoms. In another embodiment, substituted or unsubstituted linear or branched alkyl amine chain of 2-50 carbon atoms. In another embodiment, $L_1''$ is any combination of substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, and substituted or unsubstituted linear or branched alkyl amine chain of 2-50 carbon atoms.

In one embodiment, $L_1$, $L_1'$ and $L_1''$ are different. In another embodiment, $L_1$, $L_1'$ and $L_1''$ are the same. In another embodiment, $L_1$ and $L_1'$ are the same and $L_1''$ is different. In another embodiment, $L_1$ and $L_1''$ are the same and $L_1'$ is different. In another embodiment, $L_1'$ and $L_1''$ are the same and $L_1$ is different.

In one embodiment, $L_2$ of formula I is a substituted or unsubstituted linear or branched alkyl diamide chain of 2-50 carbon atoms. In another embodiment, substituted alkyl diamide chain of 2-50 carbon atoms. In another embodiment, substituted linear alkyl diamide of 2-6 carbon atoms, wherein substitutions include: one or more groups selected from halogen, hydroxy, hydroxyalkyl, alkoxy, haloalkyl, carbonyl, amido, alkylamido, dialkylamido, nitro, cyano, amino, alkylamino, dialkylamino, carboxyl, thiol, thioalkyl and the like. In another embodiment, $L_2$ is

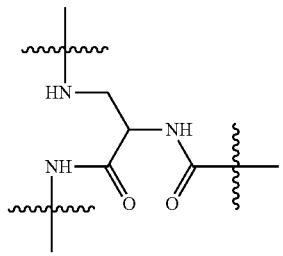

In another embodiment, $L_2$ is a substituted or unsubstituted linear or branched alkyl ether chain of 2-50 carbon atoms. In another embodiment, substituted or unsubstituted linear or branched alkyl phosphate chain of 2-50 carbon atoms. In another embodiment, substituted or unsubstituted linear or branched alkyl amide chain of 2-50 carbon atoms. In another embodiment, substituted or unsubstituted linear or branched alkyl chain of 2-50 carbon atoms. In another embodiment, substituted or unsubstituted linear or branched alkyl amine chain of 2-50 carbon atoms. In another embodiment, $L_2$ is any combination of substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, and substituted or unsubstituted linear or branched alkyl amine chain of 2-50 carbon atoms.

In one embodiment, $L_3$ of formula I or II is a substituted or unsubstituted linear or branched alkyl ether chain of 2-50 carbon atoms. In another embodiment, unsubstituted linear alkyl ether chain of 2-20 carbon atoms. In another embodiment, unsubstituted linear alkyl ether chain of 2-8 carbon atoms. In another embodiment, $L_3$ is $(CH_2CH_2O)_n$, wherein n is an integer between 1 and 10. In another embodiment, n is 3. In another embodiment, $L_3$ is polyethylene glycol (PEG). In another embodiment, $L_3$ is a substituted or unsubstituted linear or branched alkyl chain of 2-50 carbon atoms. In another embodiment, substituted or unsubstituted linear or branched alkyl phosphate chain of 2-50 carbon atoms. In another embodiment, substituted or unsubstituted linear or branched alkyl amide chain of 2-50 carbon atoms. In another embodiment, substituted or unsubstituted linear or branched alkyl diamide chain of 2-50 carbon atoms. In another embodiment, substituted or unsubstituted linear or branched alkyl amine chain of 2-50 carbon atoms. In another embodiment, $L_3$ is any combination of substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, and substituted or unsubstituted linear or branched alkyl amine chain of 2-50 carbon atoms.

In one embodiment, $L_4$ of formula I, II, (D), D(a), X, or X(a) is a combination of substituted or unsubstituted linear or branched alkyl ether chain of 2-50 carbon atoms and substituted or unsubstituted linear or branched alkyl amide chain of 2-50 carbon atoms. In another embodiment, a combination of unsubstituted linear alkyl ether chain of 2-50 carbon atoms and unsubstituted linear alkyl amide chain of 2-50 carbon atoms. In another embodiment, the unsubstituted linear alkyl ether chain is of 2-6 carbon atoms. In another embodiment, the unsubstituted linear alkyl amide chain is of 2-6 carbon atoms. In another embodiment, $L_4$ is a combination of a linear alkyl ether and linear alkyl amide of 3-10 carbon atoms (i.e., alkylether-alkylamide). In another embodiment, $L_4$ is $-(CH_2)_n-NHCO-(CH_2)_m-O-(CH_2)_l-$, wherein n, m and l are each independently an integer between 1 and 6. In another embodiment, $L_4$ is $-(CH_2)_4-NHCO-(CH_2)_2-O-CH_2-$. In another embodiment, $L_4$ is represented by the following structure:

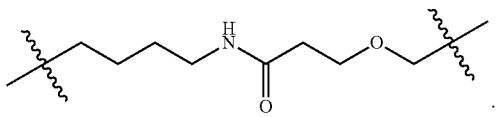 [SMILES: *CCCCNC(=O)CCOC*]

In another embodiment, $L_4$ is a substituted or unsubstituted linear or branched alkyl ether chain of 2-50 carbon atoms. In another embodiment, substituted or unsubstituted linear or branched alkyl chain of 2-50 carbon atoms. In another embodiment, substituted or unsubstituted linear or branched alkyl phosphate chain of 2-50 carbon atoms. In another embodiment, substituted or unsubstituted linear or branched alkyl amide chain of 2-50 carbon atoms. In another embodiment, substituted or unsubstituted linear or branched alkyl diamide chain of 2-50 carbon atoms. In another embodiment, substituted or unsubstituted linear or branched alkyl amine chain of 2-50 carbon atoms. In another embodiment, $L_4$ is any combination of substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, and substituted or unsubstituted linear or branched alkyl amine chain of 2-50 carbon atoms.

In one embodiment, $L_4'$ of formula I, II, (D), D(a), X, or X(a) is a combination of substituted or unsubstituted linear or branched alkyl ether chain of 2-50 carbon atoms and substituted or unsubstituted linear or branched alkyl amide chain of 2-50 carbon atoms. In another embodiment, a combination of unsubstituted linear alkyl ether chain of 2-50 carbon atoms and unsubstituted linear alkyl amide chain of 2-50 carbon atoms. In another embodiment, the unsubstituted linear alkyl ether chain is of 2-6 carbon atoms. In another embodiment, the unsubstituted linear alkyl amide chain is of 2-6 carbon atoms. In another embodiment, $L_4'$ is a combination of a linear alkyl ether and linear alkyl amide of 3-10 carbon atoms (i.e., alkylether-alkylamide). In another embodiment, $L_4'$ is $-(CH_2)_n-NHCO-(CH_2)_m-O-(CH_2)_l-$, wherein n, m and l are each independently an integer between 1 and 6. In another embodiment, $L_4'$ is $-(CH_2)_4-NHCO-(CH_2)_2-O-CH_2-$. In another embodiment, $L_4'$ is represented by the following structure:

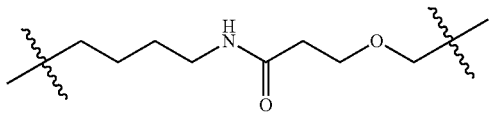

In another embodiment, $L_4'$ is a substituted or unsubstituted linear or branched alkyl ether chain of 2-50 carbon atoms. In another embodiment, substituted or unsubstituted linear or branched alkyl chain of 2-50 carbon atoms. In another embodiment, substituted or unsubstituted linear or branched alkyl phosphate chain of 2-50 carbon atoms. In another embodiment, substituted or unsubstituted linear or branched alkyl amide chain of 2-50 carbon atoms. In another embodiment, substituted or unsubstituted linear or branched alkyl diamide chain of 2-50 carbon atoms. In another embodiment, substituted or unsubstituted linear or branched alkyl amine chain of 2-50 carbon atoms. In another embodiment, $L_4'$ is any combination of substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, and substituted or unsubstituted linear or branched alkyl amine chain of 2-50 carbon atoms.

In one embodiment, $L_4''$ of formula I, II, (D), D(a), X, or X(a) is a combination of substituted or unsubstituted linear or branched alkyl ether chain of 2-50 carbon atoms and substituted or unsubstituted linear or branched alkyl amide chain of 2-50 carbon atoms. In another embodiment, a combination of unsubstituted linear alkyl ether chain of 2-50 carbon atoms and unsubstituted linear alkyl amide chain of 2-50 carbon atoms. In another embodiment, the unsubstituted linear alkyl ether chain is of 2-6 carbon atoms. In another embodiment, the unsubstituted linear alkyl amide chain is of 2-6 carbon atoms. In another embodiment, $L_4''$ is a combination of a linear alkyl ether and linear alkyl amide of 3-10 carbon atoms (i.e., alkylether-alkylamide). In another embodiment, $L_4''$ is $-(CH_2)_n-NHCO-(CH_2)_m-O-(CH_2)_l-$, wherein n, m and l are each independently an integer between 1 and 6. In another embodiment, $L_4''$ is $-(CH_2)_4-NHCO-(CH_2)_2-O-CH_2-$. In another embodiment, $L_4''$ is represented by the following structure:

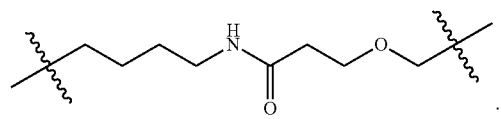 [SMILES: *CCCCNC(=O)CCOC*]

In another embodiment, $L_4''$ is a substituted or unsubstituted linear or branched alkyl ether chain of 2-50 carbon atoms. In another embodiment, substituted or unsubstituted linear or branched alkyl chain of 2-50 carbon atoms. In another embodiment, substituted or unsubstituted linear or branched alkyl phosphate chain of 2-50 carbon atoms. In another embodiment, substituted or unsubstituted linear or branched alkyl amide chain of 2-50 carbon atoms. In another embodiment, substituted or unsubstituted linear or branched alkyl diamide chain of 2-50 carbon atoms. In another embodiment, substituted or unsubstituted linear or branched alkyl amine chain of 2-50 carbon atoms. In another embodiment, $L_4''$ is any combination of substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, and substituted or unsubstituted linear or branched alkyl amine chain of 2-50 carbon atoms.

In one embodiment, $L_4$, $L_4'$ and $L_4''$ are different. In another embodiment, $L_4$, $L_4'$ and $L_4''$ are the same. In another embodiment, $L_4$ and $L_4'$ are the same and $L_4'$ is different. In another embodiment, $L_4$ and $L_4''$ are the same and $L_4'$ is different. In another embodiment, $L_4'$ and $L_4''$ are the same and $L_4$ is different.

In one embodiment, "dye" of formula I, II or III is a solvatochromic dye. In another embodiment, a fluorophore. In another embodiment, dansyl, fluorescein (6-FAM), FAM, cyanine dyes (e.g. Cy3, Cy5), sulfoindocyanine, nile red, rhodamine, perylene, fluorenyl, coumarin, 7-methoxycoumarin (Mca), dabcyl, NBD, Nile blue, Tamra, BODIPY, or derivative thereof. In another embodiment, dansyl. In another embodiment, fluorescein (6-FAM). In another embodiment, FAM. In another embodiment, cyanine dyes (e.g. Cy3, Cy5). In another embodiment, sulfoindocyanine. In another embodiment, nile red. In another embodiment, rhodamine. In another embodiment, perylene. In another embodiment, fluorenyl. In another embodiment, coumarin. In another embodiment, 7-methoxycoumarin (Mca). In another embodiment, dabcyl. In another embodiment, NBD. In another embodiment, Nile blue. In another embodiment, Tamra. In another embodiment, BODIPY. In another embodiment, a derivative of any one of dansyl, fluorescein (6-FAM), FAM, cyanine dyes (e.g. Cy3, Cy5), sulfoindocyanine, nile red, rhodamine, perylene, fluorenyl, coumarin, 7-methoxycoumarin (Mca), dabcyl, NBD, Nile blue, Tamra, or BODIPY.

In one embodiment, "peptide" of formula I, II, III, IV, (A) or (B) is any peptide comprising between 2 to 30 amino acid sequence. In another embodiment, the peptides possess between 4 to 15 amino acid sequences. In another embodiment, the peptides possess between 2 to 20 amino acid sequences. In another embodiment, the peptides possess between 3 to 10 amino acid sequences. In another embodiment, the peptide comprises 3-8 amino acids. In another embodiment, the peptide comprises 4 amino acids. In another embodiment, the peptide comprises 6 amino acids. In another embodiment, the peptides comprise hydrophobic amino acids. In another embodiment, the peptide is SEQ ID No. 1. In another embodiment, the peptides comprise polar amino acids. In another embodiment, the peptide is SEQ ID No. 3. In another embodiment, the peptides comprise negatively charged amino acids. In another embodiment, the peptide is SEQ ID No. 2. In another embodiment, the peptides comprise positively charged amino acids. In another embodiment, the peptide is SEQ ID No. 4. In another embodiment, the peptides comprise combination of hydrophobic and negatively charged amino acids. In another embodiment, the peptides comprise combination of hydrophobic and positively charged amino acids. In another embodiment, the peptide is SEQ ID No. 5. In another embodiment, the peptides comprise combination of hydrophobic and polar amino acids. In another embodiment, the peptides comprise combination of polar and negatively charged amino acids. In another embodiment, the peptides comprise combination of polar and positively charged amino acids. In another embodiment the peptides are as described in Table 1, 1A and FIG. 14.

In another embodiment, n of formula III is an integer number between 1 and 20. In another embodiment, between 2 and 10. In another embodiment, between 1 and 8. In another embodiment, 2. In another embodiment, 3. In another embodiment, 4. In another embodiment, 5. In another embodiment, 6. In another embodiment, 7.

In one embodiment, M of formula X or XX is cobalt (Co). In another embodiment, M is nickel (Ni). In another embodiment, M is Ni(II). In another embodiment, M is Co(II). In another embodiment, M is Co(III).

In one embodiment, $R_1$ of formula X, X(a), XX or XX(a) is azide. In another embodiment, amine. In another embodiment, $C_2$-$C_6$ alkyne. In another embodiment, $C_2$ alkyne. In another embodiment, thioester. In another embodiment, disulfide. In another embodiment, maleimide. In another embodiment, biotin. In another embodiment, carboxyl. In another embodiment, thiol. In another embodiment, triazole.

In another embodiment, alkylamide. In another embodiment, carbamate. In another embodiment,

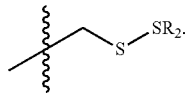

In another embodiment,

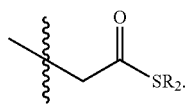

In another embodiment,

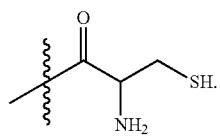

In another embodiment,

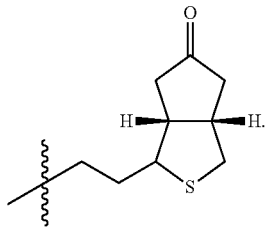

In another embodiment,

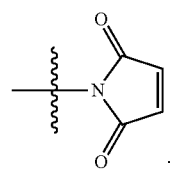

In one embodiment, $R_2$ of formula X, X(a), XX or XX(a) is a hydrogen. In another embodiment, substituted or unsubstituted linear or branched arylalkyl. In another embodiment, unsubstituted linear arylalkyl. In another embodiment, benzyl (i.e., —$CH_2$-Ph). In another embodiment, substituted or unsubstituted linear or branched $C_1$-$C_{12}$ alkyl. In another embodiment, unsubstituted linear $C_1$-$C_6$ alkyl. In another embodiment, methyl. In another embodiment, propyl. In another embodiment, ethyl. In another embodiment, t-Butyl. In another embodiment, hexyl. In another embodiment, $C_1$-$C_{12}$ haloalkyl. In another embodiment, $CF_3$.

An "alkyl" or "alkylene" group refers, in one embodiment, to a saturated aliphatic hydrocarbon, including straight-chain and branched-chain. In one embodiment, the alkyl group has 1-20 carbons. In another embodiment, the alkyl has 1-12 carbons. In another embodiment, the alkyl group has 1-7 carbons. In another embodiment, the alkyl group has 1-5 carbons. In another embodiment, the alkyl group has 1-6 carbons. In another embodiment, the alkyl group has 1-4 carbons. The alkyl group may be unsubstituted or substituted by one or more groups selected from halogen, hydroxy, hydroxyalkyl, alkoxy, haloalkyl, carbonyl, amido, alkylamido, dialkylamido, nitro, cyano, amino, alkylamino, dialkylamino, carboxyl, thiol and thioalkyl. In another embodiment, the alkyl is —$(CH_2)_6$—. In another embodiment, the alkyl is —$(CH_2)_2$—. In another embodiment, the alkyl is —$(CH_2)_3$—. In another embodiment, the alkyl is —$CH_2$—. In another embodiment, the alkyl is —$CH_2$—$CH(CH_2$—$OH)$—$(CH_2)_4$—. In another embodiment, the alkyl is —$CH_2$—$CH(CH_2$—$OH)$—. In some embodiments the alkyl of this invention is optionally substituted and optionally interrupted by a heteroatom consisting of O, N, P, S or combination thereof.

A "haloalkyl" group refers, in another embodiment, to an alkyl group as defined above, which is substituted by one or more halogen atoms, e.g. by F, Cl, Br or I.

A "hydroxyl" group refers, in another embodiment, to an OH group. It is understood by a person skilled in the art that when $R_1$, $R_2$ or $R_3$ in the compounds of the present invention is OR, then R is not OH.

In one embodiment, the term "halogen" or "halo" refers to a halogen, such as F, Cl, Br or I.

An "alkynyl" refers to unsaturated hydrocarbon which comprises at least one carbon-carbon triple bond. In one embodiment, the alkynyl group has 2-20 carbons. In another embodiment, the alkynyl has 2-12 carbons. In another embodiment, the alkynyl has 2-6 carbons. In another embodiment, the alkynyl has 2 carbons.

An "arylalkyl" group refers to an alkyl bound to an aryl, wherein alkyl and aryl are as defined above. An example of an aralkyl group is a benzyl group.

An "aryl" group refers to an aromatic group having at least one carbocyclic aromatic group or heterocyclic aromatic group, which may be unsubstituted or substituted by one or more groups selected from halogen, haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like. In one embodiment, the aryl group is a 4-8 membered ring. In another embodiment, the aryl group is a 4-12 membered ring(s). In another embodiment, the aryl group is a 6 membered ring. In another embodiment, the aryl group is a 5 membered ring. In another embodiment, the aryl group is 2-4 fused ring system.

An "alkyl ether" of this invention refers to an alkyl as defined above interrupted by one or more oxygen atoms. In another embodiment, alkyl ether refers to a PEG (poly ethylene glycol). In one embodiment, the alkylether has 1-6 carbon atoms. In another embodiment, the alkylether has 1-12 carbon atoms. In another embodiment, the alkylether has 1-20 carbon atoms. In another embodiment, the alkylether has 3 carbon atoms. In another embodiment, the alkylether has 4 carbon atoms. In another embodiment, the alkylether has 2-5 carbon atoms. In another embodiment, the alkylether has 2 carbon atoms. In another embodiment, the alkylether is —$CH_2$—$CH_2$—$O$—$CH_2$—.

An "alkyl amine" of this invention refers to an alkyl as defined above which has an amine moiety within the carbon atom chain. In another embodiment, alkyl amine refers to $(CH_2)_n$—NH—. In another embodiment, the amine moiety is at one end of the carbon chain. In another embodiment, the amine moiety is within the backbone of the carbon chain. In another embodiment, the alkyl amine is a substituted or unsubstituted linear or branched alkyl of 1-6 carbon atoms which has an amine moiety at one end. In another embodiment, the alkyl amine is a substituted or unsubstituted linear or branched alkyl of 1-12 carbon atoms which has an amine moiety at one end. In another embodiment, the alkyl amine is a substituted or unsubstituted linear or branched alkyl of 1-3 carbon atoms which has an amine moiety at one end.

An "alkyl amide" of this invention refers to an alkyl as defined above which has an amide moiety at one end. In another embodiment, alkyl amide refers to $(CH_2)_n$—NHC(O). In another embodiment, alkyl amide refers to $(CH_2)_n$—C(O)NH wherein n is an integer between 1 and 10. In another embodiment, the alkyl amide is a substituted or unsubstituted linear or branched alkyl of 1-6 carbon atoms which has an amide moiety at one end. In another embodiment, the alkyl amide is a substituted or unsubstituted linear or branched alkyl of 1-12 carbon atoms which has an amide moiety at one end. In another embodiment, the alkyl amide is a substituted or unsubstituted linear or branched alkyl of 1-3 carbon atoms which has an amide moiety at one end. In another embodiment, the alkyl amide is —$(CH_2)_6$—NHC(O). In another embodiment, the alkyl amide is —$(CH_2)_2$—NHC(O). In another embodiment, the alkyl amide is —$CH_2$—NHC(O). In another embodiment, the alkyl amide is —$CH_2$—$CH(CH_2$—$OH)$—$(CH_2)_4$—NHC(O). In another embodiment, the alkyl amide is —$CH_2$—$CH(CH_2$—$OH)$—NHC(O).

An "alkyl di-amide" of this invention refers to an alkyl as defined above which is interrupted by two amide moieties. In one embodiment, alkyl di-amide refers to $(CH_2)_n$—NHC(O)—$(CH_2)_m$—NHC(O) wherein n is an integer between 1 and 10. In another embodiment, the alkyl di-amide is a substituted or unsubstituted linear or branched alkyl of 1-6 carbon atoms which has an amide moiety at one end of the carbon chain and another amide moiety inside the backbone of the chain. In another embodiment, the alkyl di-amide is a substituted or unsubstituted linear or branched alkyl of 2-12 carbon atoms which has two amide moieties within the carbon chain. In another embodiment, the alkyl di-amide is a substituted or unsubstituted linear or branched alkyl of 2-6 carbon atoms which has two amide moieties within the carbon chain. In another embodiment, the alkyl di-amide is a substituted or unsubstituted linear or branched alkyl of 1-20 carbon atoms which has two amide moieties within the carbon chain. In another embodiment, the alkyl di-amide is —$CH_2$—$CH(CH_2OH)$—NHC(O)—$(CH_2)_2$—NHC(O)—. In another embodiment, the alkyl di-amide is —NHC(O)—$(CH_2)_2$—NHC(O)—.

An "alkyl triazole" of this invention refers to an alkyl as defined above which has a triazole moiety at one end. In one embodiment, alkyl triazole refers to $(CH_2)_n$-triazole wherein n is an integer between 1 and 10. In another embodiment n is 3. In another embodiment, the alkyl triazole is a substituted or unsubstituted linear or branched alkyl of 1-6 carbon atoms which has a triazole moiety at one end. In another embodiment, the alkyl triazole has 1-12 carbon atoms. In another embodiment, the alkyl triazole has 1-3 carbon atoms.

The term "substituted" refer to substitutions that include one or more groups selected from: halogen, hydroxy, hydroxyalkyl, alkoxy, haloalkyl, carbonyl, amido, alkylamido, dialkylamido, nitro, cyano, amino, alkylamino, dialkylamino, carboxyl, thiol, thioalkyl and the like.

In another embodiment, a "subject" refers to a mammal, a human, a female or a male.

The terms "comprises" and variations thereof do not have a limiting meaning where these terms appear in the description and claims.

Unless otherwise specified, "a," "an," "the," and "at least one" are used interchangeably and mean one or more than one.

Figure 3:
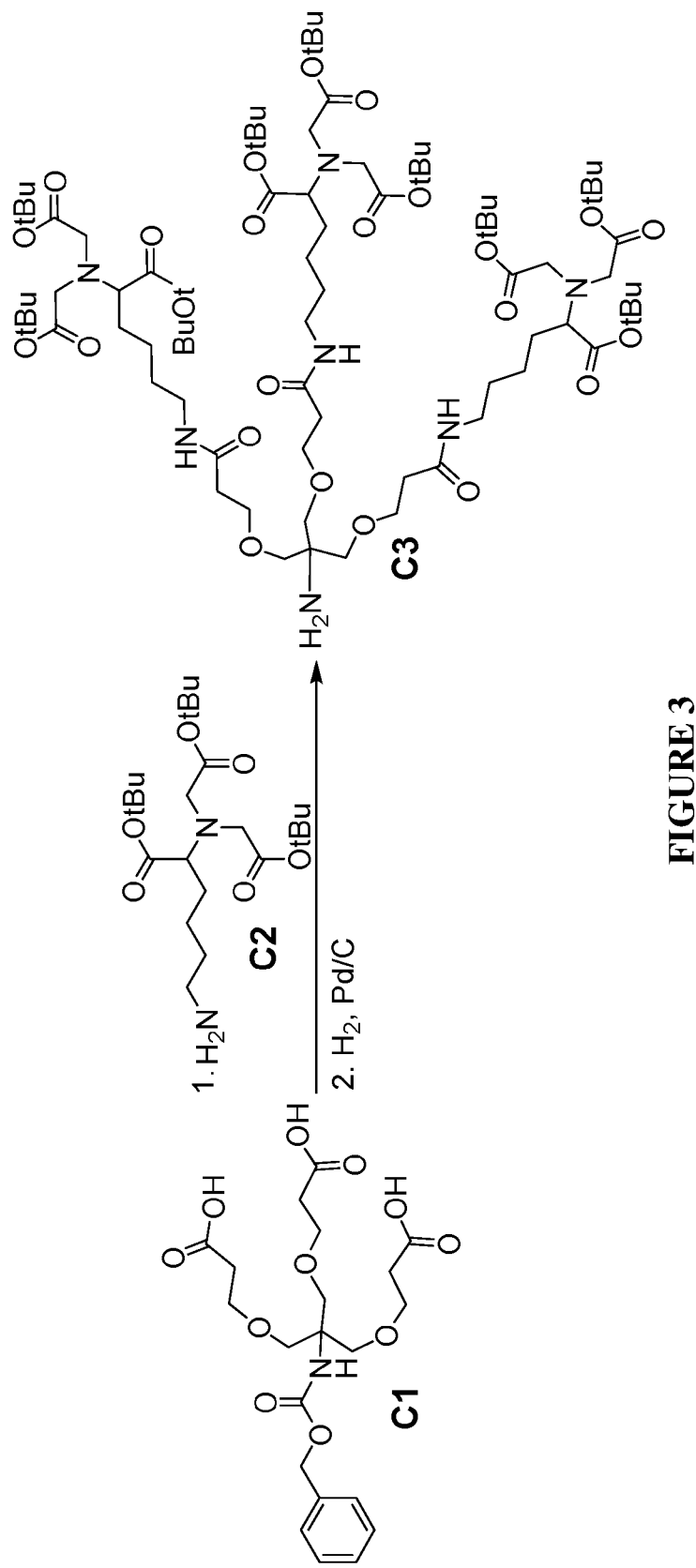
FIG. 3 depicts a synthetic scheme of the synthesis of a His-tag binder comprising tri-Nitrilotriacetic Acid (C3).

In one embodiment, this invention is further directed to the process for the preparation of His-tag binding compound, as described in Example 1, and FIG. 3. In another embodiment, this invention is directed to the process for the preparation of His-tag binding compound, as described in Example 2 and FIGS. 6-10.

Figure 4:
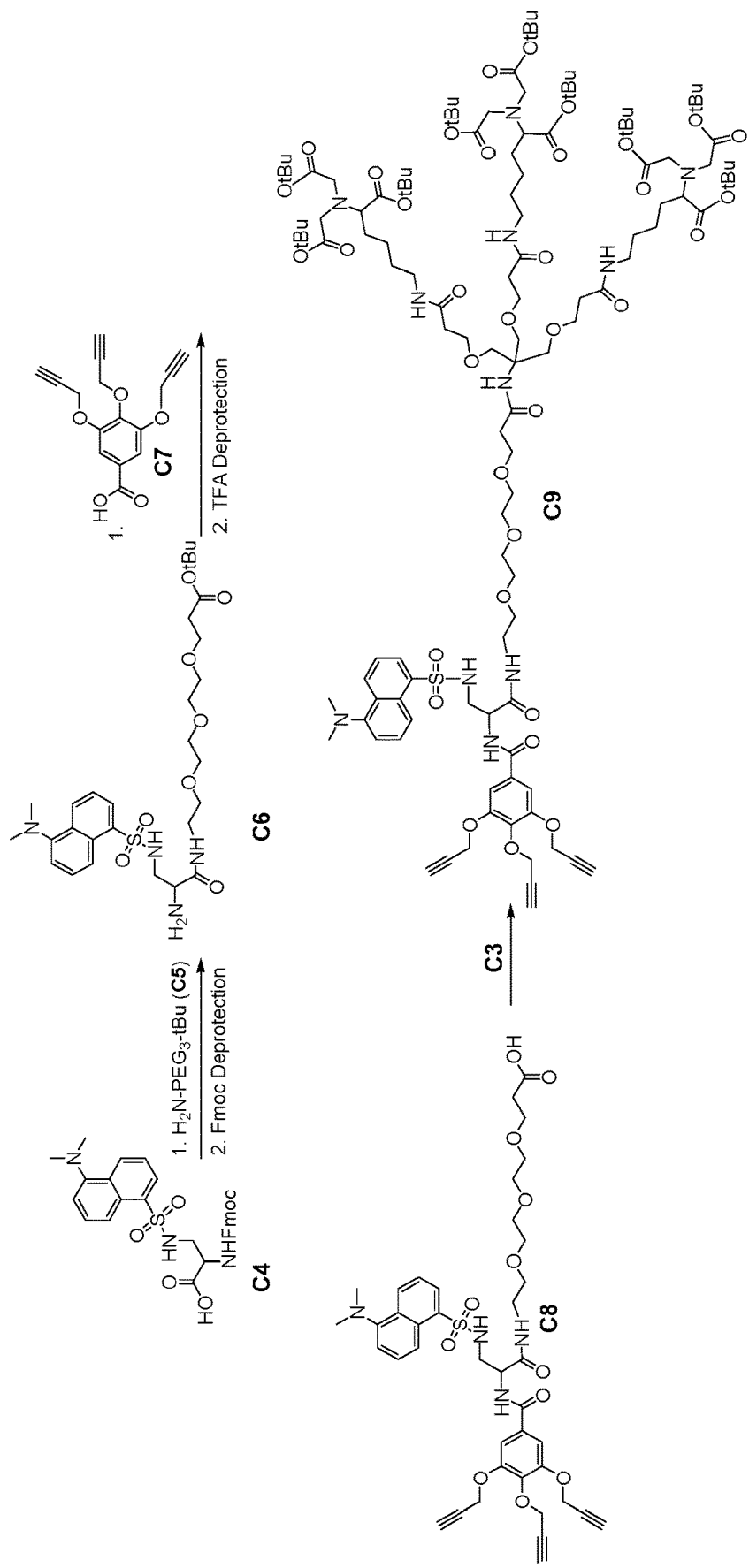
FIG. 4 depicts a synthetic scheme of the synthesis of compound C9.
Figure 5:
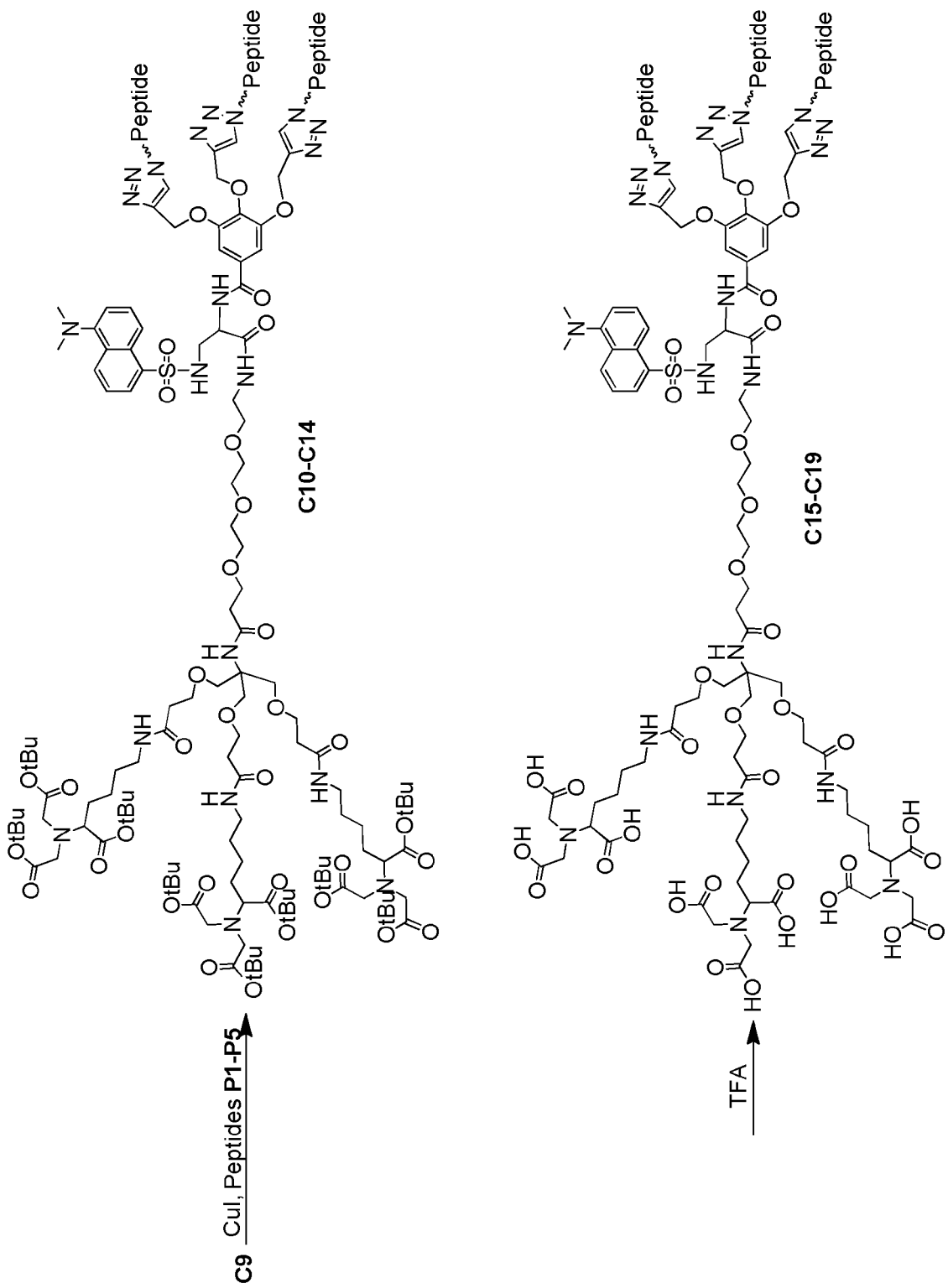
FIG. 5 depicts a synthetic scheme of the synthesis of compounds 1-5.
Figure 5:
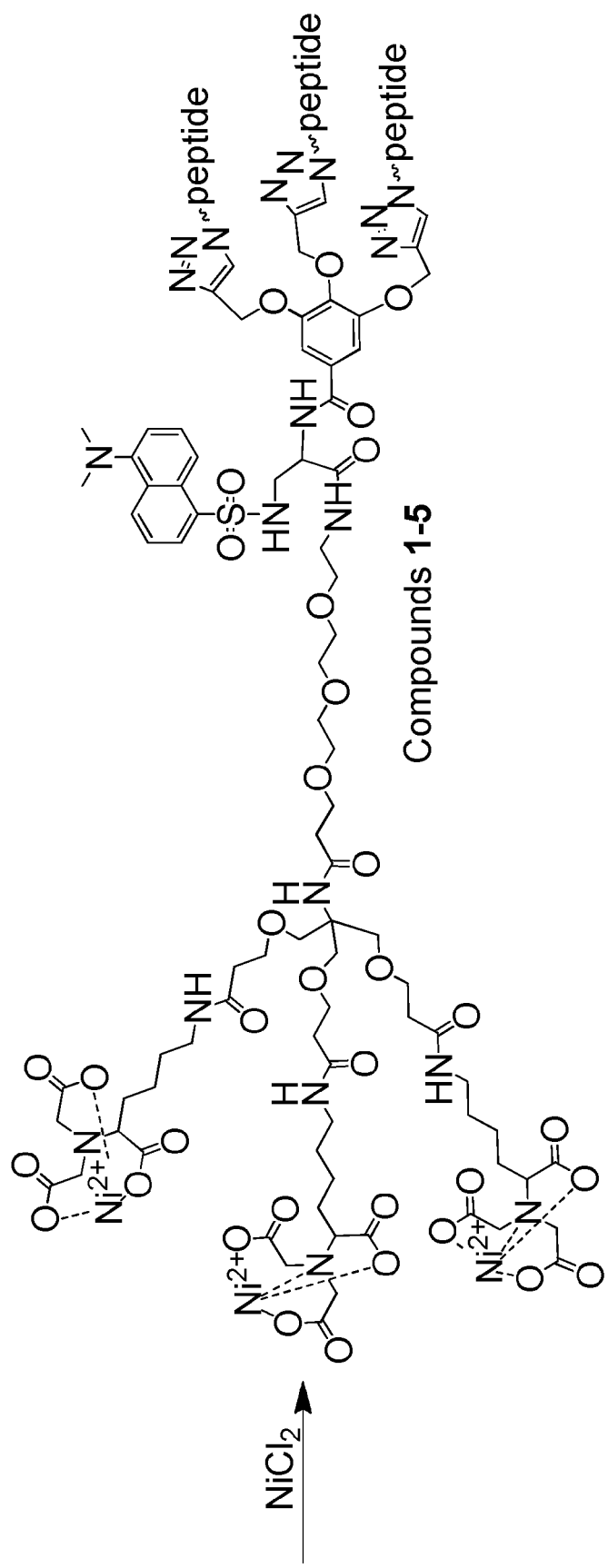
Figure 6:
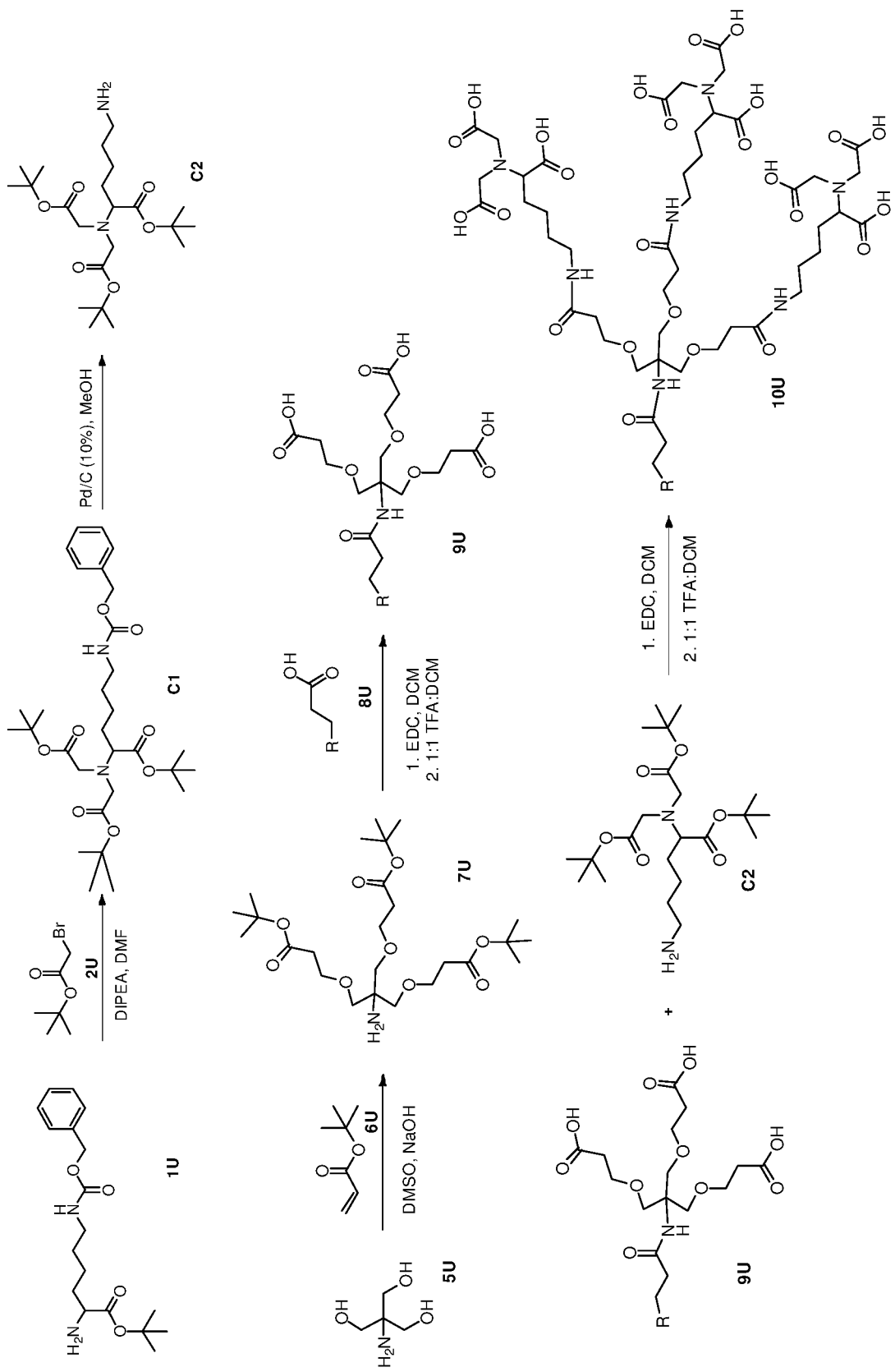
FIG. 6 depicts a synthetic scheme for preparing a variety of modified tri NTA compounds (10u) whose complex with Ni(II) can selectively bind His Tags.
Figure 14:
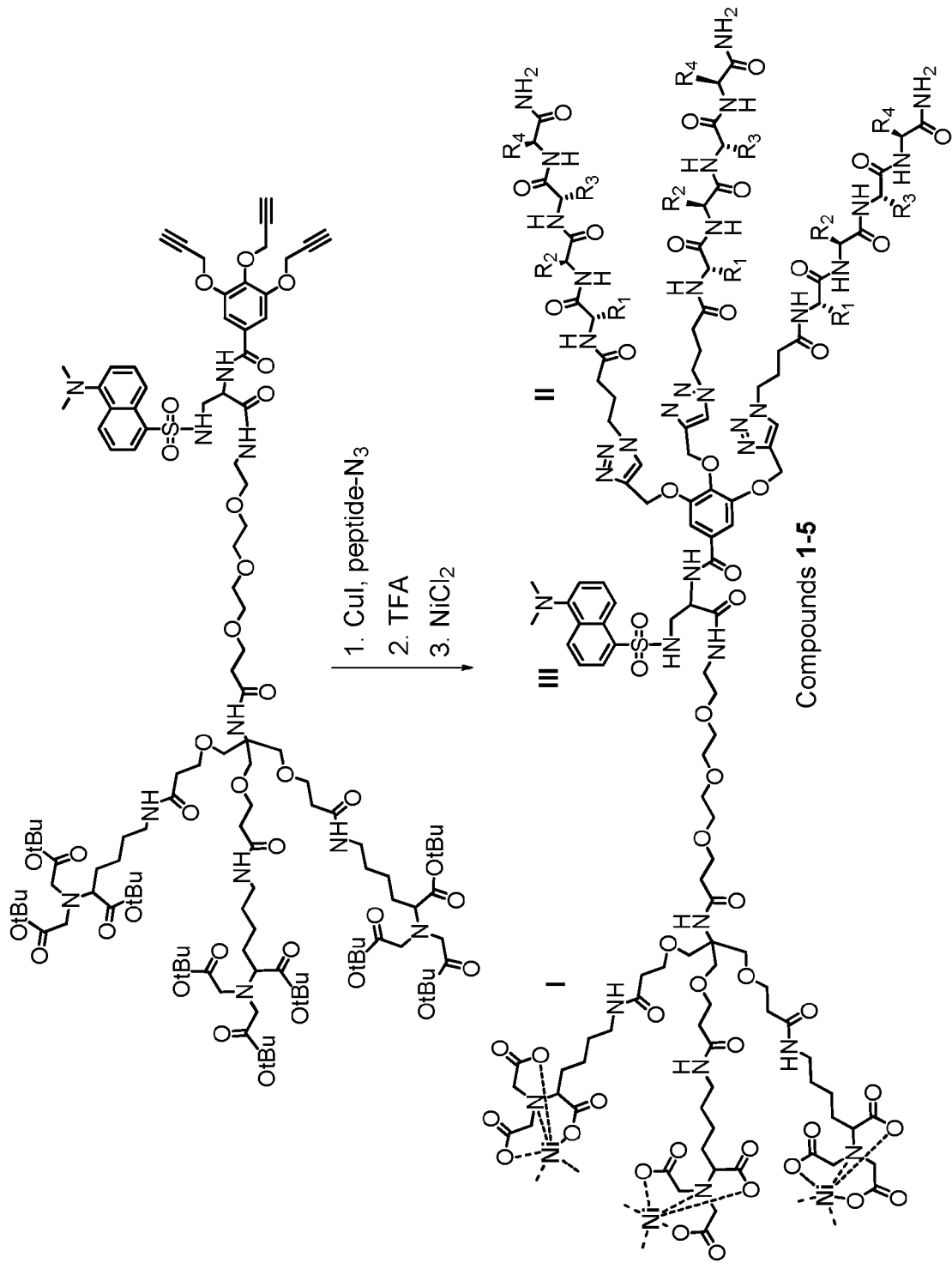
FIG. 14 depicts a method for preparing different protein surface sensors comprising a tri-$Ni^{+2}$-NTA complex (I), a tripodal peptide receptor (II), and a dansyl group (III), which serve as a His-tag binder, a protein surface receptor, and a solvatochromic probe, respectively.

In another embodiment, this invention is directed to the process for the preparation of His-tag binding compound attached to a protein surface receptor according to this invention, as described in Example 1 and FIGS. 4-5 and 14.

Figure 10:
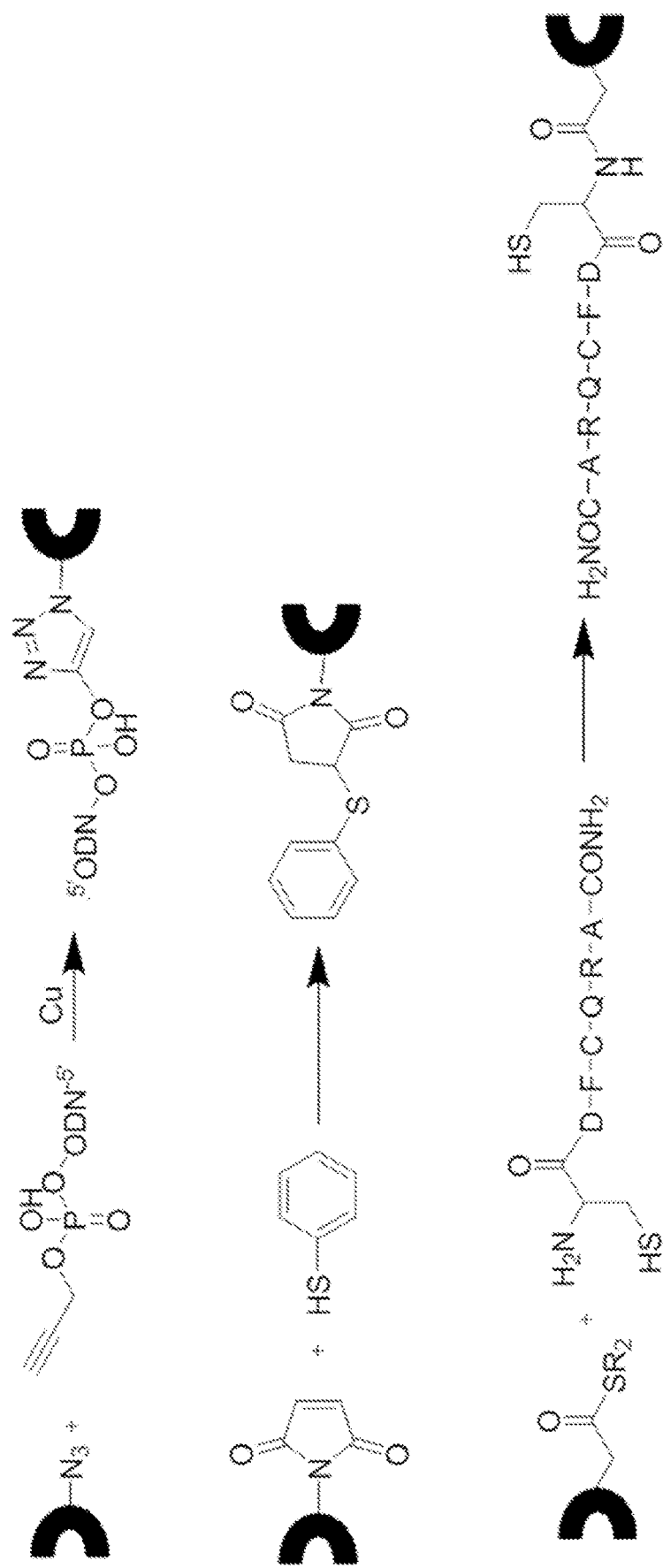
FIG. 10 depicts specific examples for modifying His-tag binding compounds of the invention to oligonucleotides (top), to small molecules (middle), and to peptides (bottom).
Figure 11:
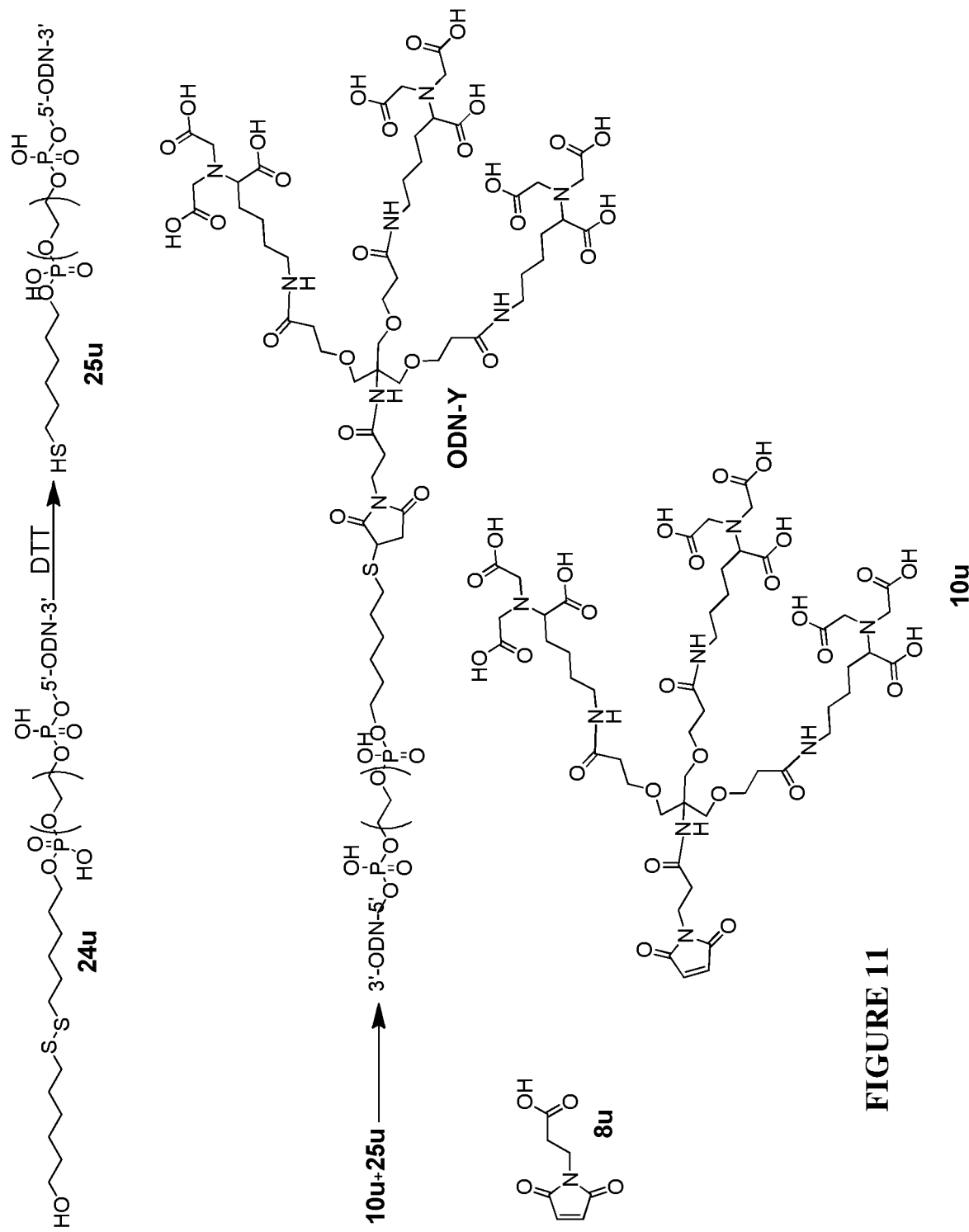
FIG. 11 depicts a synthetic scheme for an ODN modified with specific His-tag compound of the invention (ODN-Y), as well as the structures of a Maleimidopropionic acid (compound 8u), which was used to prepare the maleimide-modified His-tag binding compound (10u).

In another embodiment, this invention is directed to the process for the preparation of His-tag binding compound, attached to an oligonucleotide, as described in Example 3 and FIGS. 10 and 11.

In another embodiment, this invention is directed to the process for the preparation of His-tag binding compound, attached to a small molecule, as described in Example 2 and FIG. 10.

In another embodiment, this invention is directed to the process for the preparation of His-tag binding compound, attached to a peptide, as described in Example 2 and FIG. 10.

Applications of his-Tag Binding Compounds of the Invention.

Upon complexation with nickel, the His-tag binder described herein above, which comprise tri-NTA Nickel complex, can selectively attach to His-tagged labeled proteins inside living (in vivo) and/or fixed cells (in-vitro). Because the His-tag binding compounds and precursors according to this invention can bear various functional groups, these tri-NTA derivatives can be easily attached to various detectable probes. In one embodiment, functional groups are at position $R_1$ of compounds of formulas X, X(a), XX and XX(a) as described above. In another embodiment, derivatives may be attached by using, for example, the 'click' chemistry, amide coupling, thiol-maleimide conjugation, etc. Such probes, (e.g. fluorescent probes) therefore, could be easily generated and complexed with nickel ions to detect or label His-tagged proteins (e.g. within cells). Owing to the simple conjugation methods (i.e., 'click' chemistry, amide coupling, thiol-maleimide conjugation, etc.), this approach should enable one to attach various synthetic agents (e.g., fluorescent dyes, small molecules, peptides, oligonudleotides, and the like) to the His-tag binding compounds of this invention, which will enable bringing these synthetic agents into close proximity of His-tagged polypeptides and proteins targeted by the His-tag-binding compounds comprising the specific agents.

Accordingly, the His-tag binding compounds according to this invention may be engineered to comprise a variety of detectable groups.

"Detectable group" as used herein refers to any atom or molecule that can be engineered into the His-tag binding compound to aid in the detection of the His-tag binding compounds without significantly destroying the His-tag binding compound's ability to react with a target sequence. The His-tag binding compound may be substituted at one or more positions to add a signal generating detectable group(s). Preferably, the His-tag binding compound is substituted at the $R_1$ position of compounds of formulas X, X(a), XX and XX(a) described above.

Inclusion of more than one detectable group is also within the scope of this invention. The selection of a detectable group may be made based on the ease of the protocol for engineering the detectable group into the His-tag binding compound, and on the end use of the His-tag binding compound.

Examples of detectable groups include fluorescent groups, phosphorescent groups, luminescent groups, spin labels, photosensitizers, photocleavable moieties, chelating centers, heavy atoms, radioactive isotopes, isotopes detectable by nuclear magnetic resonance, paramagnetic atoms, and combinations thereof.

Typically, a detectable group generates a detectable signal that can be readily monitored. Examples of detectable signals that can be monitored include fluorescence, fluorescence anisotropy, time-resolved luminescence, phosphorescence amplitude and anisotropy, electron spin resonance (ESR), singlet oxygen production, hydroxy radical-mediated protein inactivation, metal-ion sensing, X-ray scattering, radioactivity, nuclear magnetic resonance spectroscopy of the attached isotope, and enhanced relaxivity of protons in the immediate vicinity of a paramagnetic species.

Other modifying groups that aid in the use of the His-tag binding compound may also be incorporated. For example, the His-tag binding compound may be substituted at one or more positions to add a solid phase binding group or a cross linking group. Preferably, the His-tag binding compound is substituted with a solid phase binding group at the $R_1$ position of compounds of formulas X, X(a), XX and XX(a) described above. The His-tag binding compound may be further coupled to a solid phase.

In one embodiment, the His-tag binding compound is capable of traversing a biological membrane. The small size of the His-tag binding compound can contribute toward the ability of the His-tag binding compound to traverse a biological membrane.

A His-tag binding compound that is unable to traverse a biological membrane may be derivatized. In one embodiment, a His-tag binding compound may be derivatized by addition of groups that enable or enhance the ability of the His-tag binding compound to traverse a biological membrane. In another embodiment, derivatization of the His-tag binding compound does not significantly alter the ability of the His-tag binding compound to subsequently react with the target sequence. In another embodiment, a His-tag binding compound may be derivatized transiently. In such instances, after traversing the membrane, the derivatizing group is eliminated to regenerate the original His-tag binding compound. Examples of derivatization methods that increase membrane traversability include esterification of phenols, ether formation with acyloxyalkyl groups, and reduction of chromophores to uncharged leuco compounds.

In some embodiments, the His-tag binding compound, engineered to comprise a detectable group, may be nearly or completely undetectable until it specifically reacts with a target sequence (i.e., with a His-tag peptide motif). Such engineered His-tag binding compound can be particularly useful because it provides a means to specifically and accurately detect the presence of the His-tag binding compound/target sequence complex with very little background signal.

Also within the scope of this invention is a His-tag binding compound that may be detectable before and after it specifically reacts with a target sequence to form the His-tag binding compound/target sequence complex. In such instances, it is preferable if the detectable signal of the His-tag binding compound can be differentiated from the detectable signal of the complex. For example, if the detectable signal of the His-tag binding compound is a fluorescent signal, it would be preferable if the fluorescence of the complex is red-shifted or blue-shifted relative to the detectable signal produced by the His-tag binding compound alone.

The His-tag binding compound may also lack a detectable signal, both before and even after specifically reacting with a target sequence. These His-tag binding compounds can be useful in many techniques that do not require a detectable signal, or that use other methods of detection. These His-tag binding compounds may be useful when the goal is to attach a polypeptide to a solid substrate, or cross-link two polypeptides.

In one embodiment, use of His-tag binding compounds according to this invention may provide a means to detect proteins of interest, wherein it may be advantageous to express these proteins of interest as His-tagged fusion proteins instead of expressing the protein as a fusion protein with a very large fluorescent protein (FP) attached to it. A His-tag binding compound of this invention, coupled to a detectable group, e.g. a fluorescent dye, may then be used to target the protein of interest (See for examples FIGS. 1 and 2). Such His-tag targeted fluorescent agent is expected to fluoresce upon binding to the targeted His-tagged protein, which may serve as a genetically targeted probe. In one embodiment, the His-tag binding compound is coupled to a protein surface receptor according to this invention. In another embodiment, the His-tag binding compound is coupled to a fluorescent dye.

In one embodiment, this invention is directed to a His-tag binding compound for use as a genetically targeted probe; or in another embodiment, for use in the detection of a protein of interest (POI) in it native environment; or in another embodiment, for use in measuring gene expression of a His-tagged polypeptide in a living and/or fixed cells; or in another embodiment, for the localization of a POI in a living and/or fixed cells.

In another embodiment, the His-tag binding compound is coupled to a fluorescent dye. In another embodiment, the His-tag binding compound is coupled to a protein surface receptor. In another embodiment, the His-tag binding compound is a sensor according to this invention.

In another embodiment, said His-tag binding compound according to this invention is covalently linked to a fluorophore, thereby obtaining said fluorescently tagged His-tag binding compound. In another embodiment, said His-tag binding compound is linked to a fluorophore through the $R_1$ moiety of compounds of formulas X, X(a), XX and XX(a). In another embodiment, said $R_1$ of compounds of formulas X, X(a), XX and XX(a) are linked to said fluorophore through a linker, wherein said linker is as described herein above for sensors according to this invention.

In one embodiment, a fluorophore comprises a solvatochromic dye. Solvatochromic fluorophores display sensitivity to the polarity of the local environment. These molecules exhibit a low quantum yield in aqueous solution, but become highly fluorescent in nonpolar solvents or when bound to hydrophobic sites in proteins or membranes. In certain embodiments, solvatochromic fluorophores include 2-propionyl-6-dimethylaminonaphthalene (PRODAN) (Weber et al. *Biochemistry* 1979, 18, 3075-3078; Cohen et al. *Science* 2002, 296, 1700-1703), 4-dimethylamino phthalimide (4-DMAP) (Saroja et al. *J. Fluoresc.* 1998, 8, 405-410), and 4-amino-1,8-naphthalimide derivatives (Grabchev et al. *J. Photochem. Photobiol., A* 2003, 158, 37-43; Martin et al. *J. Lumin.* 1996, 68, 157-146). In another embodiment, the solvatochromic fluorophore is selected from: fluorescein (6-FAM), FAM, cyanine dyes (e.g. Cy3, Cy5), sulfoindocyanine, nile red, rhodamine, perylene, fluorenyl, coumarin, 7-methoxycoumarin (Mca), dabcyl, NBD, Nile blue, Tamra, and BODIPY. In another embodiment, said solvatochromic dye is dansyl.

In one embodiment, fluorescence emission is measured over time. In another embodiment, fluorescence emission is measure before and after a His-binding compound is incubated with a His-tagged polypeptide or a cell comprising a His-tagged polypeptide. In another embodiment, said measuring is of a live cell. In another embodiment, said measuring of is a fixed cell. In another embodiment, said measuring is of a cell supernatant.

In one embodiment, a cell is a mammalian cell. In another embodiment, a cell is a rat, a mouse, a dog, or a human cell. In another embodiment, a cell is a yeast cell. In another embodiment, a cell is a tissue culture cell-line cell. In another embodiment, a cell is a primary culture cell from a transgenic mammal. In another embodiment, a cell is a recombinant cell. In yet another embodiment, a cell comprises a nucleic acid encoding a His-tagged polypepetide of interest. In another embodiment, a cell expresses a His-tagged polypeptide of interest. In another embodiment a cell secretes a His-tagged polypeptide of interest. Each possibility comprises an embodiment of this invention.

In one embodiment, this invention is directed to a method of localizing a His-tagged polypeptide of interest within a cell, said method comprising the steps of:
a. expressing said His-tagged polypeptide in a recombinant cell;
b. incubating said recombinant cell with a fluorescently-tagged His-tag binding compound; and
c. visualizing the fluorescence emission of said compound.

In one embodiment, said recombinant cell is fixed using any method known in the art, prior to the incubating step. In another embodiment, the fluorescently tagged His-tag binding compound passively crosses the plasma membrane of a live cell. In another embodiment, the fluorescently tagged His-tag binding compound is micro-injected into a live cell. In another embodiment, the fluorescently tagged His-tag binding compound is derivatized in a way that allows its crossing of the plasma membrane of a live cell. In another embodiment, said visualizing is observing under a microscope. In one embodiment, a fluorescent microscope is used to detect and localize the fluorescent signal. In another embodiment, a fluorescent microscope with a plate reader or the ability to record images at multiple locations over time is used to detect and localize the fluorescent signal.

In one embodiment, this invention is directed to a method of labeling a protein of interest (POI) in complex environment using a fluorescently tagged His-tag binding compound, said method comprising:
a. expressing a His-tagged POI in a complex environment;
b. incubating the His-tagged POI with a fluorescently tagged His-tag binding compound; and
c. measuring the fluorescence emission of said fluorescently tagged His-tag binding compound: His-tagged POI complex;
wherein detection of a fluorescent signal is dependent on the formation of said His-tag binding compound: His-tagged POI complex.

In another embodiment, said fluorescently tagged His-tag binding compound is a sensor according to this invention. In another embodiment, said fluorescently tagged His-tag binding compound is a His-tag binding compound according to this invention coupled to a fluorophore.

The term "complex environment" refers, in one embodiment, to an environment that comprises large proteins that tend to engage in non-specific interactions such as serum albumin (e.g., BSA and HSA). In another embodiment, the complex environment comprises —, IgG, IgA, Avidine, Insulin, SAv, BSA, GST-P1, HSA, AGP or any combination thereof. In another embodiment, the complex environment is an environment that stabilizes the POI. In another embodiment, the complex environment is the native environment of the POI.

In one embodiment, this invention is directed to a method of identifying a protein of interest (POI) in complex environment using a fluorescently tagged His-tag binding compound according to this invention, said method comprising:
  a. expressing a His-tagged POI in a complex environment;
  b. incubating the His-tagged POI with a fluorescently tagged His-tag binding compound; and
  c. measuring the fluorescence emission of said fluorescently tagged His-tag binding compound: His-tagged POI complex;
wherein detection of a fluorescent signal is dependent on the formation of said His-tag binding compound: His-tagged POI complex.

In another embodiment, said fluorescently tagged His-tag binding compound is a sensor according to this invention. In another embodiment, said fluorescently tagged His-tag binding compound is a His-tag binding compound according to this invention coupled to a fluorophore.

In one embodiment, this invention is directed to a method of measuring gene expression of a His-tagged polypeptide in a cell said method comprising the steps of:
  a. expressing a His-tagged polypeptide in a cell;
  b. incubating the cell with a fluorescently-tagged His-tag binding compound; and
  c. measuring the fluorescence of said cell;
wherein detection of a fluorescent signal is dependent on the formation of a His-tagged polypeptide:fluorescently tagged His-tag binding compound complex.

In another embodiment, the His-tagged polypeptide is a cell surface receptor and measuring comprising use of a fluorescent cell sorter. In another embodiment, the His-tagged polypeptide is secreted from the cells, and said measuring involves collecting the cell supernatant and measuring the fluorescence of the supernatant. In yet another embodiment, a method of measuring gene expressing comprises a further step of homogenizing a cell comprising a His-tagged polypeptide at a given time point, incubating the His-tag binding compound with the cell homogenate, and measuring the resultant fluorescence. In another embodiment, a plate reader is used to measure the fluorescence of an array of cells. In another embodiment, a low density array is used. In another embodiment, the fluorescently tagged His-tag binding compound is a sensor according to this invention. Each possibility comprises an embodiment of the invention. Methods for measuring fluorescence are well known in the art.

In one embodiment, a His-tagged polypeptide comprises a polyhistidine tag. In another embodiment, the His-tagged polypeptide comprises a 6x-His-tag. In another embodiment, said His-tagged polypeptide comprises a 10x-His-tag.
Applications of Sensor Compounds of the Invention.

Protein surface recognition by synthetic receptors is an important research direction in the areas of bioorganic and medicinal chemistry, particularly due to the ability of such receptors to disrupt the interactions between two proteins.

Herein, it is demonstrated how the attachment of protein surface receptors to genetically targeted molecules (e.g., His-tag binding compounds) can afford fluorescent sensors that respond to changes in the surfaces of affinity-labelled proteins, upon binding to metal ions, small molecules, and protein partners. It is herein demonstrated how combination of flexible linker with a modifiable synthetic receptor enables the design of various sensors that match different regions on the surface of various proteins.

In one embodiment, this invention is directed to a method of detecting changes in a protein surface using a sensor of the invention; or in another embodiment, to a method of detecting conformational changes of a protein of interest using a sensor of the invention; or in another embodiment, to a method of sensing binding interactions of a protein of interest using a sensor of the invention.

The ability to detect changes in protein surfaces opens up new possibilities for using sensors according to this invention, to identify binding partners (FIG. 2, state c). Unlike enzyme inhibitors that can be readily detected by enzymatic assays, identifying molecules that interact with protein surfaces is generally complicated by the need to use antibodies and stepwise protocols, or special techniques such as fluorescence anisotropy or SPR.

In one embodiment, this invention is directed to a method of detecting protein modifications and binding interactions, which are difficult to sense using the current available probes, using a sensor of the invention. In another embodiment, the protein is labeled. In another embodiment, a protein is labeled with any tag known in the art. In another embodiment the protein is labeled with a polyhistidine tag (His-tag). In another embodiment, said polyhistidine tag (His-tag) comprises a 6xHis-tag. In another embodiment, said polyhistidine tag (His-tag) comprises a 10xHis-tag. In another embodiment, a protein is labeled with a FLAG-tag. In another embodiment, a FLAG-tag label is a multi-FLAG tag. In another embodiment, a FLAG tag is a dimmer (2x). In another embodiment, a FLAG tag is a 3x tag. In another embodiment, a protein is labeled with a c-myc tag. In another embodiment, said label does not interfere with a protein's tertiary structure. In another embodiment, said label does not interfere with a proteins quaternary structure. Each possibility comprises an embodiment of this invention.

In one embodiment, a protein to be labeled comprises any protein known in the art, wherein a tagged-protein may be encoded by a nucleic acid sequence. In another embodiment the protein is calmodulin (CaM), G protein or B-cell lymphoma 2 protein (Bcl-2).

The terms "polypeptide", "protein", "polypeptide of interest" and "protein of interest (POI)" are used interchangeably having all the same meanings and qualities. In some embodiments, a "polypeptide" or "protein" as used herein encompasses native polypeptides (either degradation products, fractions thereof, or recombinant polypeptides, or any combination thereof). In some embodiments, modifications include, but are not limited to N terminus modification, C terminus modification, and residue modification. In certain embodiments, a polypeptide or protein may comprise a fraction of the wild-type polypeptide or protein. In some embodiments, a polypeptide or protein may comprise a mutated amino acid sequence.

In one embodiment, this invention is directed to a method of identifying a binding partner of protein of interest (POI), said method comprises:

a. incubating a sensor according to this invention with a tagged POI in solution, wherein said sensor comprises a tag binding region;
b. measuring the fluorescence intensity of said solution;
c. adding a test compound to said solution;
d. remeasuring the fluorescence intensity of said solution; and
e. determining binding of said test compound to said tagged POI based on a change in fluorescence intensity, wherein decreased fluorescent intensity indicates binding of said test compound;

thereby identifying said binding partner for said POI.

In another embodiment, said tagged-POI comprises an affinity tag. In another embodiment, said tagged-POI comprises any tag known in the art. Non limiting examples for tag are: His-tag, FLAG tag, HA tag, C-myc tag, AviTag, Calmodulin-tag, polyglutamate tag, E-tag, Myc-tag, S-tag, SBP-tag, Softag, Strep-tag, TC tag, V5 tag, VSV-tag, Xpress tag, etc. In another embodiment, said tagged-POI comprises a polyhistidine tag (His-tag). In another embodiment, said polyhistidine tag (His-tag) comprises a 6×His-tag. In another embodiment, said polyhistidine tag (His-tag) comprises a 10×His-tag. In another embodiment, said tagged-POI comprises a FLAG-tag. In another embodiment, a FLAG-tag label is a multi-FLAG tag. In another embodiment, a FLAG tag is a dimmer (2×). In another embodiment, a FLAG tag is a 3× tag. In another embodiment, said tagged-POI comprises a c-myc tag. In another embodiment, said tag does not interfere with a protein's tertiary structure. In another embodiment, said tag does not interfere with a proteins quaternary structure.

In another embodiment, said POI is calmodulin (CaM). In another embodiment, said POI is calmodulin-$Ca^{2+}$ (CaM ($Ca^{2+}$)). In another embodiment, said POI is B-cell lymphoma 2 protein (Bcl-2).

In another embodiment, the solution further comprises proteins that tend to engage in non-specific interactions. In another embodiment, the proteins that tend to engage in non-specific interactions are selected from, IgG, IgA, Avidine, Insulin, SAv, BSA, GST-P1, HSA, AGP.

In another embodiment, the binding partner is a protein. In another embodiment, the binding partner is a peptide. In another embodiment, the binding partner is a synthetic molecule. In another embodiment, the binding partner is a small molecule. In another embodiment, the binding partner is a drug. Each possibility comprises an embodiment of this invention.

In one embodiment, this invention is directed to a method of identifying binding partners of protein of interest (POI) in a complex environment, said method comprises:
a. incubating a sensor according to this invention with a tagged POI in solution, wherein said sensor comprises a tag binding region;
b. measuring the fluorescence intensity of said solution;
c. adding a complex environment comprising a test compound to said solution;
d. remeasuring the fluorescence intensity of said solution; and
e. determining binding of said test compound in complex environment to said tagged POI based on a change in fluorescence intensity, wherein decreased fluorescent intensity indicates binding of said test compound;

thereby identifying a binding partner for said POI in a complex environment.

In another embodiment, said tagged-POI comprises an affinity tag. In another embodiment, said tagged-POI comprises any tag known in the art. In another embodiment, said tagged-POI comprises a polyhistidine tag (His-tag). In another embodiment, said polyhistidine tag (His-tag) comprises a 6×His-tag. In another embodiment, said polyhistidine tag (His-tag) comprises a 10×His-tag. In another embodiment, said tagged-POI comprises a FLAG-tag. In another embodiment, a FLAG-tag label is a multi-FLAG tag. In another embodiment, a FLAG tag is a dimmer (2×). In another embodiment, a FLAG tag is a 3× tag. In another embodiment, said tagged-POI comprises a c-myc tag. In another embodiment, said tag does not interfere with a protein's tertiary structure. In another embodiment, said tag does not interfere with a proteins quaternary structure.

In another embodiment, said POI is calmodulin (CaM). In another embodiment, said POI is calmodulin-$Ca^{2+}$ (CaM ($Ca^{2+}$)). In another embodiment, said POI is B-cell lymphoma 2 protein (Bcl-2).

In another embodiment, the binding partner is a protein. In another embodiment, the binding partner is a peptide. In another embodiment, the binding partner is a synthetic molecule. In another embodiment, the binding partner is a small molecule. In another embodiment, the binding partner is a drug. Each possibility comprises an embodiment of this invention.

In one embodiment, this invention is directed to a method of measuring gene expression of a His-tagged polypeptide in a cell, said method comprising the steps of:
a. expressing a His-tagged polypeptide in a cell;
b. incubating the cell with a sensor according to this invention; and
c. measuring the fluorescence of said cell;

wherein detection of a fluorescent signal is dependent on the formation of a His-tagged polypeptide:sensor complex.

In another embodiment, said His-tagged polypeptide comprises a polyhistidine-tag. In another embodiment, said sensor comprises a tag-binding region. In another embodiment, said sensor comprises a fluorophore according to this invention. In another embodiment, said fluorophore comprises a solvatochromic dye. In another embodiment, said solvatochromic dye is dansyl. In another embodiment, said fluorescence is measured over time. In another embodiment, said measuring is of a live cell. In another embodiment, said measuring of is a fixed cell. In one embodiment, said cell is a human cell. In another embodiment, said cell is a recombinant primary culture cell. In another embodiment, said cell is a tissue culture cell.

In one embodiment, this invention is directed to a method of localizing a His-tagged polypeptide of interest within a cell, said method comprises the steps of:
a. expressing said His-tagged polypeptide in a recombinant cell;
b. incubating said recombinant cell with a sensor according to this invention; and
c. visualizing the fluorescence emission of said sensor.

In one embodiment, said recombinant cell is fixed using any method known in the art, prior to the incubating step. In another embodiment, the sensor passively crosses the plasma membrane of a live cell. In another embodiment, the sensor is micro-injected into a live cell. In another embodiment, the sensor is derivatized in a way that allows its crossing of the plasma membrane of a live cell. In another embodiment, said visualizing is observing under a microscope. In one embodiment, a fluorescent microscope is used to detect and localize the fluorescent signal. In another embodiment, a fluorescent microscope with a plate reader or the ability to record images at multiple locations over time is used to detect and localize the fluorescent signal.

In one embodiment, this invention is directed to a method of identifying the phosphorylation state of calmodulin-dependent protein kinase II (CaMKII) using a complex of His-tag labeled CaM($Ca^{2+}$) and a sensor according to this invention, said method comprises:
 a. incubating a sensor according to this invention, with a His-tag labeled CaM($Ca^{2+}$), thereby forming said complex of His-tag labeled CaM($Ca^{2+}$) and said sensor;
 b. recording the fluorescence response of said complex to addition of CaMKII in an unknown state (i.e., either phosphorylated or dephosphorylated);
wherein a decrease in the fluorescence response is indicative of CaMKII in a phosphorylated state (i.e., p-CaMKII), and increase in the fluorescence response is indicative of CaMKII in a dephosphorylated state (CaMKII).

In one embodiment, this invention is directed to a method of detecting changes that occur in the surface of a His-tag labeled protein using a sensor according to this invention, said method comprises incubating said sensor with said His-tag labeled protein, wherein an enhancement in the optical signal of said sensor is indicative of a bound sensor-protein complex, which is indicative of a specific conformational state of said protein. In another embodiment, the optical signal is fluorescence emission. In another embodiment, the His-tag labeled protein is a His-CaM. In another embodiment, the His-tag labeled protein is a His-CaM ($Ca^{2+}$). In another embodiment, the His-tag labeled protein is a His-Bcl-2.

In one embodiment, this invention is directed to a method of identifying a compound that binds to a His-tag labeled protein of interest (His-tag-POI), said method comprises:
 a. incubating a sensor according to this invention, with said His-tag labeled protein of interest (His-tag-POI) in solution, wherein said sensor comprises a tag binding region;
 b. measuring the fluorescence intensity of said solution;
 c. adding a test compound to said solution;
 d. remeasuring the fluorescence intensity of said solution; and
 e. determining binding of said test compound to said His-tag-POI based on a change in fluorescence intensity, wherein decreased fluorescent intensity indicates binding of said test compound;
thereby identifying a compound that binds said His-tag-POI.

In another embodiment, the POI is calmodulin (CaM). In another embodiment, said POI is calmodulin-$Ca^{2+}$ (CaM ($Ca^{2+}$)). In another embodiment, said POI is B-cell lymphoma 2 protein (Bcl-2).

In another embodiment, the solution further comprises proteins that tend to engage in non-specific interactions. In another embodiment, the proteins that tend to engage in non-specific interactions are selected from IgG, IgA, Avidine, Insulin, SAv, BSA, GST-P1, HSA, AGP.

In another embodiment, the test compound is a protein. In another embodiment, the test compound is a peptide. In another embodiment, the test compound is a synthetic molecule. In another embodiment, the test compound is a small molecule. In another embodiment, the test compound is a drug. Each possibility comprises an embodiment of this invention.

In one embodiment, this invention is directed to a method of identifying a compound that binds to a protein of interest (POI), said method comprises:
 a. incubating a sensor according to this invention, with a protein of interest labeled with a histidine tag (His-tag-POI) in solution;
 b. measuring the fluorescence intensity of said solution;
 c. adding a test compound to said solution;
 d. remeasuring the fluorescence intensity of said solution; and
 e. determining binding of said test compound to said His-tag-POI based on a change in fluorescence intensity, wherein decreased fluorescent intensity indicates binding of said test compound;
thereby identifying a compound that binds said POI.

In another embodiment, the POI is calmodulin (CaM). In another embodiment, said POI is calmodulin-$Ca^{2+}$ (CaM ($Ca^{2+}$)). In another embodiment, said POI is B-cell lymphoma 2 protein (Bcl-2).

In another embodiment, the solution further comprises proteins that tend to engage in non-specific interactions. In another embodiment, the proteins that tend to engage in non-specific interactions are selected from—IgG, IgA, Avidine, Insulin, SAv, BSA, GST-P1, HSA, AGP.

In another embodiment, the test compound is a protein. In another embodiment, the test compound is a peptide. In another embodiment, the test compound is a synthetic molecule. In another embodiment, the test compound is a small molecule. In another embodiment, the test compound is a drug.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

The following examples are presented in order to more fully illustrate the preferred embodiments of the invention. They should in no way be construed, however, as limiting the broad scope of the invention.

EXAMPLES

Materials and Methods

All solvents and reagents were obtained from commercial suppliers and used without further purification. Dry solvents were purchased from Sigma Aldrich with the exception of dry DMSO, which was purchased from Arcos.

IgG from human serum, IgA from human serum, human serum albumin (HSA), human $\alpha_1$ acid glycoprotein (AGP) and calmodulin (CaM) from bovine testes were purchased from Sigma Aldrich. Human recombinant GST-P1-1, mouse recombinant His-calmodulin, human recombinant Drp1 (DAPK-related protein 1), and human recombinant CaMKII were obtained from the Israel Structural Proteomics Center (Weizmann Institute of Science). M13 and Bax BH3 peptide (55-74) wild type were purchased from Anaspec (Fremont, Calif.). Protein G protein fragment His-Tag was purchased from abcam. Recombinant human insulin from yeast, recombinant human B-cell lymphoma protein 2 alpha His-Tag (Bcl-2), recombinant streptavidin from *streptomyces avidinii*, and avidin from hen's egg white were all purchased from ProSpec-Tany TechnoGene Ltd. (Ness Ziona, Israel). Bovine serum albumin (BSA) was purchased from MP biomedicals (Santa Ana, Calif.). Fmoc-L-2,3-diaminopropionic acid, cholesterol and paclitaxel were purchased from Chem-Impex International (Wood Dale, Ill.). $H_2N$-$PEG_3$-tBu, 4-Azidobutyric acid and tolbutamide were purchased from Chem-Impex International (Wood Dale, Ill.), ChemPep, Inc. (Wellington, Fla.), and Chiralix (Nijmegen, The Netherlands), respectively. Calmidazolium, Mastoparan, sodium salicylate, andrographolide, pioglitazone, DPC (fenamic acid), apigenin, aspirin, carbimazole, α-D-glucose-6-phosphate monosodium salt (α-G6P), angiotensin II human, 1,3-PB-ITU dihydrobromide, irsogladine maleate, and PP2 (4-amino-5-(4-chlorophenyl)-7-(t-butyl)pyrazolo [3,4-d]pyrimidine) were purchased from Santa Cruz Biotechnology. Dopamine, histamine dihydrochlorine, ouabain octhahydrate, naringin, amikacin, biotin, digitoxin, estrone, glucose pentaacetate, podophyllotoxin, colchicine, neocuproine hydrate, and erythromycin were purchased from Sigma Aldrich. λ-protein phosphatase and CaMKII (phospho Thr305) antibody were purchased from New England Biolabs (UK) Ltd, and GeneTex (Irvine, Calif.), respectively. Anti-flag-tag antibody was purchased from Pierce thermo scientific (Rockford, Ill.). The $^1$H NMR spectra were recorded on a Bruker Avance 300 MHz NMR instrument. Electrospray mass spectrometry was performed either with a Micromass Platform LCZ-4000 instrument at the Weizmann Institute of Science mass spectrometry facility or by using the LTQ Orbitrap Discovery hybrid FT mass spectrometer (Thermo Fisher Scientific, Inc.) equipped with an electrospray ionization ion source at the Faculty of Agriculture, Hebrew University of Jerusalem. The exact masses from elemental compositions were calculated using Chem-Draw Ultra 12.0. Analytical reversed phase high-performance liquid chromatography (RP-HPLC) analysis was performed either on a Waters liquid chromatography system equipped with a 2487 dual wavelength UV detector, 600 gradient pump, and a 717 plus autosampler or an Agilent 1260 infinity quaternary pump LC system, maximum pressure 400 bar, equipped with a diode-array detector with max-light high-sensitivity cartridge cell.

Peptides were either synthesized manually (peptide P1, Table 1) or purchased from Synpeptide Co., Ltd. Shanghai, China (peptides P2 and P3, Table 1) or using an automated synthesizer (Advanced ChemTech, Apex 396) (peptides P4 and P5, Table 1). The azido-modified peptides (Table 1) and compounds C10-C19 (Table 1) were purified by RP-HPLC using a ThermoSeparation instrument (P200 pump, UV 100 detector), and a pre-packed Vydac $C_{18}$ column. Protein structures were produced using Discovery Studio Visualizer, version 2.5 (Accelrys, San Diego, Calif.). Structures of CaM, CaM($Ca^{+2}$), CaM-M13, CaMKII, and CaMKII/CaM ($Ca^{+2}$) were taken from the Protein Databank codes 1CFD, 1CLL, 2BBM, 2VN9, 2WEL, respectively.

Fluorescence was measured using a BioTek synergy H4 hybrid multiwell plate reader, in black flat-bottom polystyrene NBS 384-well microplates (Corning). The same machine was used to calculate the concentration of the final sensors using clear flat-bottom polystyrene 384 well microplates (Corning). The concentrations of compounds 1-5 were determined by measuring the absorbance of dansyl at 330 nm and using an extinction coefficient ε=4300 $M^{-1}cm^{-1}$. Protein concentrations were determined using a NanoDrop ND-1000 spectrophotometer (Thermo Scientific).

Example 1

Synthetic Details for Various Compounds of the Invention Synthesis of Tri-Nitrilotriacetic Acid (C3) (FIG. 3)

Compounds C1 and C2 were synthesized according to published procedures. The synthetic details of compounds C1 and C2 are described in Example 3 below.

Compound C1 (615 mg, 1.3 mmol), compound C2 (1.8 g, 4.18 mmol), EDC (996.8 mg, 5.2 mmol), HOBt (175.63 mg, 1.3 mmol), and triethyl amine (725.2 μL, 5.2 mmol) were mixed under argon in dry THF (40 mL) for 36 hours. The solvent was evaporated and the mixture was re-dissolved in diethyl ether and washed with HCl (0.5 M) and brine. After drying with $Na_2SO_4$, the product was purified by combiflash silica column chromatography using a gradient of 0-7% MeOH in DCM to afford the pure material (1.16 g, 52% yield).

$^1$H NMR (300 MHz, $CDCl_3$): δ=1.43 (s, 54H), 1.44 (s, 27H), 1.50-1.56 (m, 12H), 1.63-1.65 (m, 6H), 2.40 (t, J=5.7 Hz, 6H), 3.15-3.22 (m, 6H), 3.32 (t, J=7.4 Hz, 3H), 3.40-3.54 (m, 12H), 3.62 (s, 6H), 3.67 (t, J=5.6 Hz, 6H), 5.01 (s, 2H), 5.40 (s, 1H), 6.78-6.79 (m, 2H), 7.32-7.33 (m, 5H).

$ESI^+$-MS (m/z): calcd. for $[M+Na]^+$ 1732.04. found 1732.42. calcd. for $[M+2Na]^{+2}$ 877.01. found 877.40. calcd. for $[M+3Na]^{+3}$ 592.34. found 592.84.

This product was then hydrogenated using 10% Pd/C (86 mg) in methanol (20 mL) under $H_2$ atmosphere (1 atm) overnight. After complete removal of the benzyl group, as determined by TLC and ninhydrin staining, the palladium catalyst was filtered through cotton to afford a viscous oily product (925 mg, 87% yield).

$^1$H NMR (300 MHz, $CDCl_3$): δ=1.44 (s, 54H), 1.45 (s, 27H), 1.52-1.58 (m, 12H), 1.63-1.64 (m, 6H), 2.42-2.50 (m, 6H), 3.22-3.24 (m, 6H), 3.27-3.32 (m, 3H), 3.36-3.47 (m, 12H), 3.50-3.62 (m, 6H), 3.72-3.75 (m, 6H), 6.65-6.68 (m, 1H), 7.17 (br-s, 2H). $ESI^+$-MS (m/z): calcd. for $[M+H]^+$ 1575.03. found 1575.29. calcd. for $[M+2H]^{+2}$ 788.01. found 788.40.

Synthesis of Compound C9 (FIG. 4)

C4, C7 were synthesized according to previously published procedures.

Compound C6

C4 (1.64 g, 2.9 mmol), C5 (805 mg, 2.9 mmol), DIPEA (1 mL, 5.8 mmol), and HATU (1.1 g, 2.9 mmol) were stirred in dry THF (50 mL) under argon at room temperature overnight. The reaction mixture was evaporated and then purified by combiflash silica column chromatography using a gradient of 0-8% MeOH in DCM to afford the Fmoc protected product (2.13 g, 89% yield).

$^1$H NMR (300 MHz, $CDCl_3$): δ=1.42 (s, 9H), 2.45 (t, J=6.6 Hz, 2H), 2.86 (s, 6H), 3.10-3.33 (m, 2H), 3.38-3.45 (m, 2H), 3.54-3.60 (m, 10H), 3.65 (t, J=6.5 Hz, 2H), 4.17-4.21 (m, 1H), 4.27 (m, 1H), 4.31-4.33 (m, 2H), 5.99-6.06 (m, 2H), 6.97 (br-s, 1H), 7.16 (d, J=7.5 Hz, 1H), 7.29-7.34 (m, 2H), 7.37-7.42 (m, 2H), 7.49-7.60 (m, 4H), 7.76 (d, J=7.5 Hz, 2H), 8.25-8.28 (m, 2H), 8.54 (d, J=8.4 Hz, 1H).

$ESI^+$-MS (m/z): calcd. for $[M+Na]^+$ 841.34. found 841.39.

Next, the Fmoc group of the residue (321 mg, 0.39 mmol) was deprotected by 20% piperidine in dry DMF (15 mL) for 1 hour. The solvent was then evaporated and the residue was further placed under high vacuum for 6 h. The product was purified by combiflash silica column chromatography using a gradient of 0-3.5% MeOH in DCM to afford C6 (170 mg, 65% yield).

$^1$H NMR (300 MHz, $CDCl_3$): δ=1.42 (s, 9H), 2.50 (t, J=6 Hz, 2H), 2.88 (s, 6H), 3.09 (dd, J=4.8, 13.5 Hz, 1H), 3.18-3.24 (m, 2H), 3.40-3.45 (m, 2H), 3.50 (t, J=5.3 Hz, 1H), 3.54-3.57 (m, 2H), 3.60-3.62 (m, 8H), 3.69 (t, J=6.2

Hz, 2H), 7.18 (d, J=7.5 Hz, 1H), 7.49-7.60 (m, 2H), 7.64-7.65 (m, 1H), 8.18-8.26 (m, 2H), 8.54 (d, J=8.4 Hz, 1H).

ESI$^+$-MS (m/z): calcd. for [M+H]$^+$ 597.29. found 597.40. calcd. for [M+Na]$^+$ 619.27. found 619.40.

Compound C8

C6 (168 mg, 0.281 mmol), C7 (88.04 mg, 0.309 mmol), N,N-Diisopropylethylamine (DIPEA) (97.88 µL, 0.56 mmol), and HCTU (290.6 mg, 0.70 mmol) were stirred in 10 mL dry THF under argon at room temperature overnight. Then the solvent was evaporated and the residue was purified by combiflash silica column chromatography using a gradient of 0-5% MeOH in DCM. The fractions containing the product were collected, dissolved with ethyl acetate, and washed with 0.5M HCl, 0.5 M NaOH and brine, and then the organic layer was dried with Na$_2$SO$_4$. The tert-butyl protected product (130 mg) was obtained with a 53% yield.

$^1$H NMR (300 MHz, CDCl$_3$): δ=1.42 (s, 9H), 2.44-2.49 (m, 2H), 2.58-2.59 (m, 1H), 2.79 (s, 2H), 2.89 (s, 6H), 3.15-3.24 (m, 1H), 3.42-3.46 (m, 3H), 3.56 (br-s 6H), 3.60 (br-s 4H) 3.66 (t, J=6.5 Hz, 2H), 4.59-4.61 (m, 1H), 4.82-4.84 (m, 6H), 6.39-6.43 (m, 1H), 7.19 (d, J=7.5 Hz, 1H), 7.31 (t, J=5.3 Hz, 1H), 7.36 (s, 2H), 7.48-7.57 (m, 2H), 7.82 (d, J=6.9 Hz, 1H), 8.23-8.27 (m, 2H), 8.56 (d, J=8.4 Hz, 1H).

ESI$^+$-MS (m/z): calcd. for [M+Na]$^+$ 885.33. found 885.19. calcd. for [2M+Na]$^{+1}$ 1747.68. found 1747.50.

The tert-butyl protected product (120 mg) was then dissolved in a mixture of TFA/DCM (6 mL; 1:1) and stirred for 2 h. The reaction mixture was diluted with chloroform (50 mL) and evaporated 5 times and placed under high vacuum overnight to afford C8 in a quantitative yield.

$^1$H NMR (300 MHz, CDCl$_3$): δ=2.47 (t, J=2.1 Hz, 1H), 2.55-2.58 (m, 4H), 2.95 (s, 6H), 3.24-3.34 (m, 2H), 3.43-3.47 (m, 2H), 3.58-3.70 (m, 10H), 3.73-3.80 (m, 2H), 4.79-4.81 (m, 7H), 6.82 (t, J=6.2 Hz, 1H), 7.21-7.24 (m, 1H), 7.28 (s, 2H), 7.48-7.56 (m, 2H), 7.77-7.82 (m, 1H), 7.91 (d, J=7.5 Hz, 1H), 8.25 (d, J=7.2 Hz, 1H), 8.36 (d, J=8.7 Hz, 1H), 8.58 (d, J=8.4 Hz, 1H).

ESI$^+$-MS (m/z): calcd. for [M+Na]$^+$ 829.27. found 829.35, calculated for [M−H+2Na]$^+$ 851.25. found 851.41. ESI$^-$-MS (m/z): calcd. for [M−H]$^-$ 805.27. found 805.39.

Compound C9

A solution of C8 (40 mg, 49.5 µmol), C3 (186 mg, 118 µmol), HCTU (56.29 mg, 136 µmol), and DIPEA (23.6 µL, 135.5 µmol) in 3 mL dry THF was stirred overnight under argon. The solvent was evaporated and the reaction was purified by combiflash silica column chromatography using a gradient of 0-4.8% MeOH in EtOAc to afford C9 (74 mg, 63% yield).

$^1$H NMR (300 MHz, CD$_3$CN): δ=1.40-1.42 (m, 81H), 1.56-1.61 (m, 18H), 2.29-2.31 (m, 11H), 2.82-2.84 (m, 6H), 2.90 (br-s, 1H), 3.09-3.11 (m, 6H), 3.25-3.32 (m, 8H), 3.36-3.41 (m, 10H), 3.45-3.48 (m, 11H), 3.58 (br-s, 13H), 4.42-4.46 (m, 1H), 4.74-4.76 (m, 2H), 4.80-4.81 (m, 4H), 6.66-6.67 (m, 1H), 6.83-6.85 (m, 3H), 7.16-7.21 (m, 3H), 7.49-7.58 (m, 2H), 7.68-7.70 (m, 1H), 8.17-8.24 (m, 2H), 8.47-8.52 (m, 1H).

ESI$^+$-MS (m/z): calcd. for [M+3Na]$^{+3}$ 810.75. found 810.84 calcd. for [M+2Na]$^{+2}$ 1204.63. found 1204.67.

Synthesis of Compounds 1-5. (FIGS. 5, 14)

TABLE 1

The sequences of the peptides used in this study.

| Compound peptide | Peptide | sequence |
|---|---|---|
| C10, C15 | P1 | N$_3$-(CH$_2$)$_3$-I-L-S-G-CONH$_2$ |
| C11, C16 | P2 | N$_3$-(CH$_2$)$_3$-G-E-S-E-COOH |
| C12, C17 | P3 | N$_3$-(CH$_2$)$_3$-S-G-S-S-COOH |
| C13, C18 | P4 | N$_3$-(CH$_2$)$_3$-S-K-S-K-CONH$_2$ |
| C14, C19 | P5 | N$_3$-(CH$_2$)$_3$-I-L-K-S-I-K-CONH$_2$ |

Table 1A
SEQ ID Nos. of the peptides used in this study.

| Peptide sequence | SEQ ID No. |
|---|---|
| I-L-S-G | SEQ ID No. 1 |
| G-E-S-E | SEQ ID No. 2 |
| S-G-S-S | SEQ ID No. 3 |
| S-K-S-K | SEQ ID No. 4 |
| I-L-K-S-I-K | SEQ ID No. 5 |

Compound C10

C9 (6.52 mg, 2.76 µmol) and P1 (Table 1, 8.25 mg, 16.5 µmol) were dissolved in 200 µL DMSO and 2 mL acetonitrile under argon. Then 2,6-lutidine (3.82 µL, 33 µmol), DIPEA (5.75 µL, 33 µmol), and CuI (1.84 mg, 9.65 µmol) were sequentially added under argon. The reaction mixture was stirred overnight. The solvents were removed and the residue was purified using RP-HPLC. Yield: 22.5%.

HRMS-ESI$^+$ (m/z) calcd. for [M+2Na]$^{+2}$, 1952.5753. found, 1952.5712. calcd. for [M+3Na]$^{+3}$, 1309.3800. found 1309.3784.

Compound C11

C9 (5.18 mg, 2.19 µmol) and P2 (7 mg, 13.1 µmol) were dissolved in 100 µL DMSO under argon. Then 2,6-lutidine (3.07 µL, 26.3 µmol), DIPEA (4.58 µL, 26.3 µmol), and CuI (5 mg, 26.3 µmol) were sequentially added under argon. The reaction mixture was stirred overnight. The reaction was purified using RP-HPLC. Yield 23%. C11 was used directly for the next step.

Compound C12

C9 (3.64 mg, 1.54 µmol) and P3 (4.14 mg, 9.255 µmol) were dissolved in 100 µL DMSO under argon. Then 2,6-lutidine (2.15 µL, 18.5 µmol), DIPEA (3.22 µL, 18.5 µmol), and CuI (3.52 mg, 18.5 µmol) were sequentially added under argon. The reaction mixture was stirred overnight. The reaction was purified using RP-HPLC. Yield 52.6%.

HRMS-ESI$^-$ (m/z) calcd. for [M−2H]$^{-2}$, 1851.8987. found 1851.8998. calcd. for [M−3H]$^{-3}$, 1234.2634. found 1234.2618.

Compound C13

C9 (6.13 mg, 2.59 µmol) and P4 (8.7 mg, 15.6 µmol) were dissolved in 100 µL DMSO under argon. Then 2,6-lutidine (3.62 µL, 31.1 µmol), DIPEA (5.42 µL, 31.1 µmol), and CuI (5.93 mg, 31.1 µmol) were sequentially added under argon. The reaction mixture was stirred overnight. The reaction was purified using RP-HPLC. Yield 42%.

HRMS-ESI$^+$ (m/z) calcd. for [M+3H]$^{+3}$ 1347.4304. found 1347.4290. calcd. for [M+4H]$^{+4}$ 1010.8246. found 1010.8240. calcd. for [M+5H]$^{+5}$ 808.8611. found 808.8604.

Compound C14

C9 (3.93 mg, 1.66 µmol) and P5 (8.1 mg, 9.98 µmol) were dissolved in 100 µL DMSO under argon. Then 2,6-lutidine (2.32 µL, 19.9 µmol), DIPEA (3.46 µL, 19.9 µmol), and CuI (3.79 mg, 19.9 µmol) were sequentially added under argon. The reaction mixture was stirred overnight. The reaction was purified using RP-HPLC. Yield 37%.

HRMS-ESI$^-$ (m/z) calcd. for [M−3H]$^{-3}$ 1597.6360. found 1597.6362.

Compounds C15-C19

Compounds C10-C14 were deprotected using 50% TFA in DCM (1 mL) for 6 h. The solvent and TFA were removed and the products were purified using RP-HPLC.

Compound C15: yield 40%, HRMS-EST (m/z) calcd. for [M−3H+Na]$^{-2}$ 1686.7864. found 1686.7852. calcd. for [M−3H]$^{-3}$ 1116.8612. found 1116.8598.

Compound C16: yield 32%, HRMS-ESI$^-$ (m/z) calcd. for [M−2H]$^{-2}$ 1725.1470. found 1725.1455. calcd. for [M−3H]$^{-3}$ 1149.7623. found 1149.7610.

Compound C17: yield 29%, HRMS-ESI$^-$ (m/z) calcd. for [M−2H]$^{-2}$ 1599.1153. found 1599.1142. calcd. for [M−3H]$^{-3}$ 1065.7411. found 1065.7411.

Compound C18: yield 38%, HRMS-ESI$^-$ (m/z) calcd. for [M−2H]$^{-2}$ 1766.3456. found 1766.3456. calcd. for [M−3H]$^{-3}$ 1177.2280. found 1177.2273.

Compound C19: yield 64%, HRMS-ESI$^-$ (m/z) calcd. for [M−3H]$^{-3}$ 1429.4482. found 1429.4482.

General Procedure for Peptide Synthesis

Peptide 1 (P1, Table 1) was synthesized manually on Rink amide resin using standard solid phase Fmoc method. Coupling reactions were run on a 0.2-mmol scale. The coupling was carried out using a twofold excess of each amino acid (coupling for 1 hour), PyBOP/NMM as the coupling reagents, and 25% piperdine in NMP for Fmoc deprotection. 4-azidobutyric acid (1.2 equiv.) was coupled overnight using the HOAT/DIC (1.2 equiv.) coupling reagents.

Peptides 2 and 3 (P2 and P3, Table 1), synthesized on Wang resin were purchased from Synpeptide Co., Ltd. Shanghai, China.

Peptides 4 and 5 (P4 and P5, Table 1) were synthesized using an automated synthesizer (Advanced ChemTech, Apex 396) on Rink amide resin. The coupling was carried out using a sixfold excess of each amino acid (coupling for 2×45 min), HCTU/DIPEA as coupling reagents, and 25% piperdine in NMP for Fmoc deprotection. 4-azidobutyric acid (1.2 equiv.) was coupled overnight using HOAT/DIC (1.2 equiv.) coupling reagents. The peptides were cleaved from resin by TFA/H$_2$O/triisopropylsilane (95:2.5:2.5) for 2 h. The peptides were purified using preparative RP-HPLC on a C$_{18}$ column and characterized by electrospray mass spectrometry.

P1: ESI$^+$-MS (m/z): calcd. for [M+H]$^+$ 499.29. found 499.32. calcd. for [M+Na]$^+$ 521.28. found 521.26.

P2: ESI$^-$-MS (m/z): calcd. for [M−H]$^-$ 530.18. found 530.20.

P3: ESI$^-$-MS (m/z): calcd. for [M−H]$^-$ 446.16. found 446.13.

P4: ESI$^+$-MS (m/z): calcd. for [M+H]$^+$ 559.33. found 559.43 calcd. for [M+Na]$^+$ 581.31. found 581.36.

P5: ESI$^+$-MS (m/z): calcd. for [M+H]$^+$ 811.55. found 811.60.

Compounds 1-5

An aqueous solution of NiCl$_2$ (final concentration, 79.2 µM) was added to a solution of compounds 1-5 (12 µM) in PBS buffer (4.1 mM, pH=7.3) and incubated for either 30 minutes or overnight.

Example 2

Synthetic Routes for Preparing Various his-Tag Binders (Compound 10u) (FIGS. 6-10)

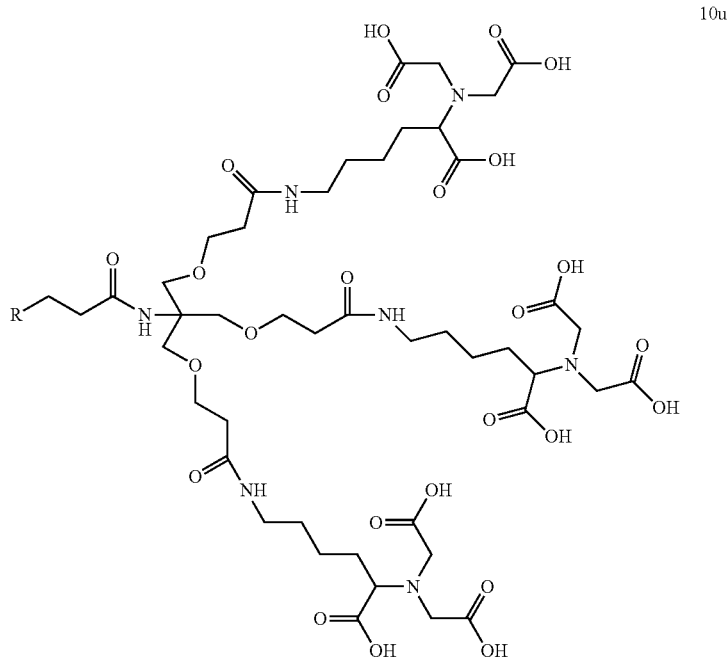

The synthesis of 10u begins with N-alkylation of N-benzyloxycarbonyl-L-lysine tert-butyl ester (1u) with tert-butyl bromoacetate (2u), followed by benzyl deprotection to obtain an amino-modified NTA (C2), according to a literature procedure. A tripodal precursor molecule (9u) was also synthesized according to a reported procedure by 1,4-addition of 2-amino-2-hydroxymethyl-propane-1,3-diol (5u) to tert-butyl acrylate (6u), followed by coupling to a modified carboxylic acid (8u) and TFA deprotection. The final product (10u), whose complex with Nickel (II) can tightly bind His-tags, was obtained by coupling 9u to C2 using EDC and deprotecting the t-butyl groups by TFA.

Figure 7:
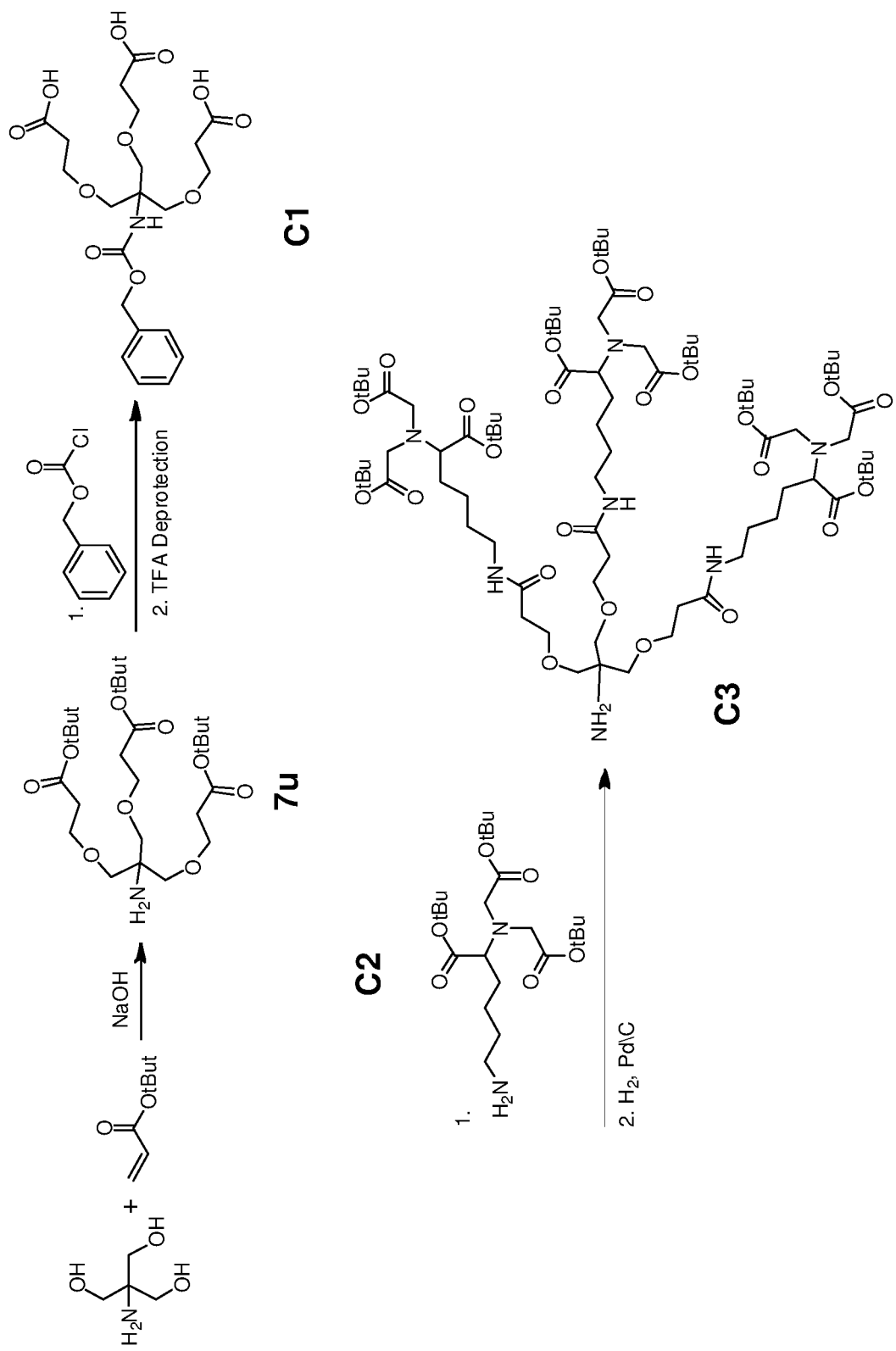
FIG. 7 depicts a synthetic scheme for preparing compound C3.

In order to afford an amine-modified and t-Bu-protected tri-NTA (C3), compound 7u can also be protected by Benzyl chloroformate followed by coupling to C2 and benzyl deprotection to afford compound C3 (FIG. 7).

Figure 8:
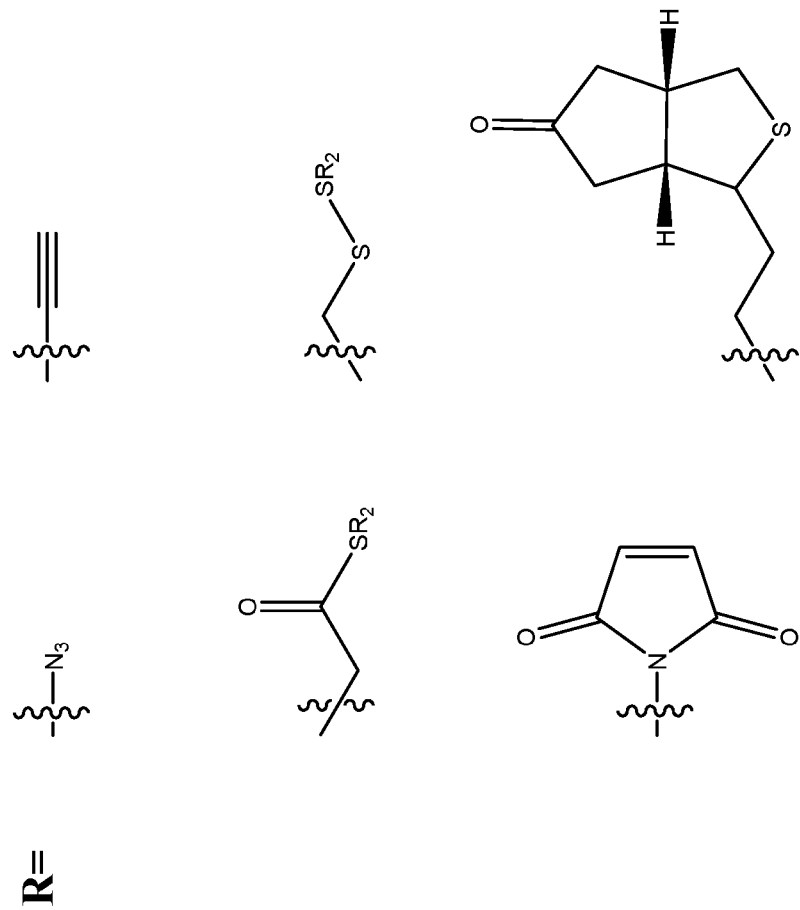
FIG. 8 depicts examples of various possible R groups for compound 8u [R($CH_2$)$_x$COOH].

The modified carboxylic acid of compound 8u (FIG. 6) can be any $R(CH_2)x$ COOH, where x represents the number of carbons and the R groups can consist of various functionalities, such as an azide, alkyne, thioester, disulfide, maleimide, and biotin (FIG. 8).

Figure 9:
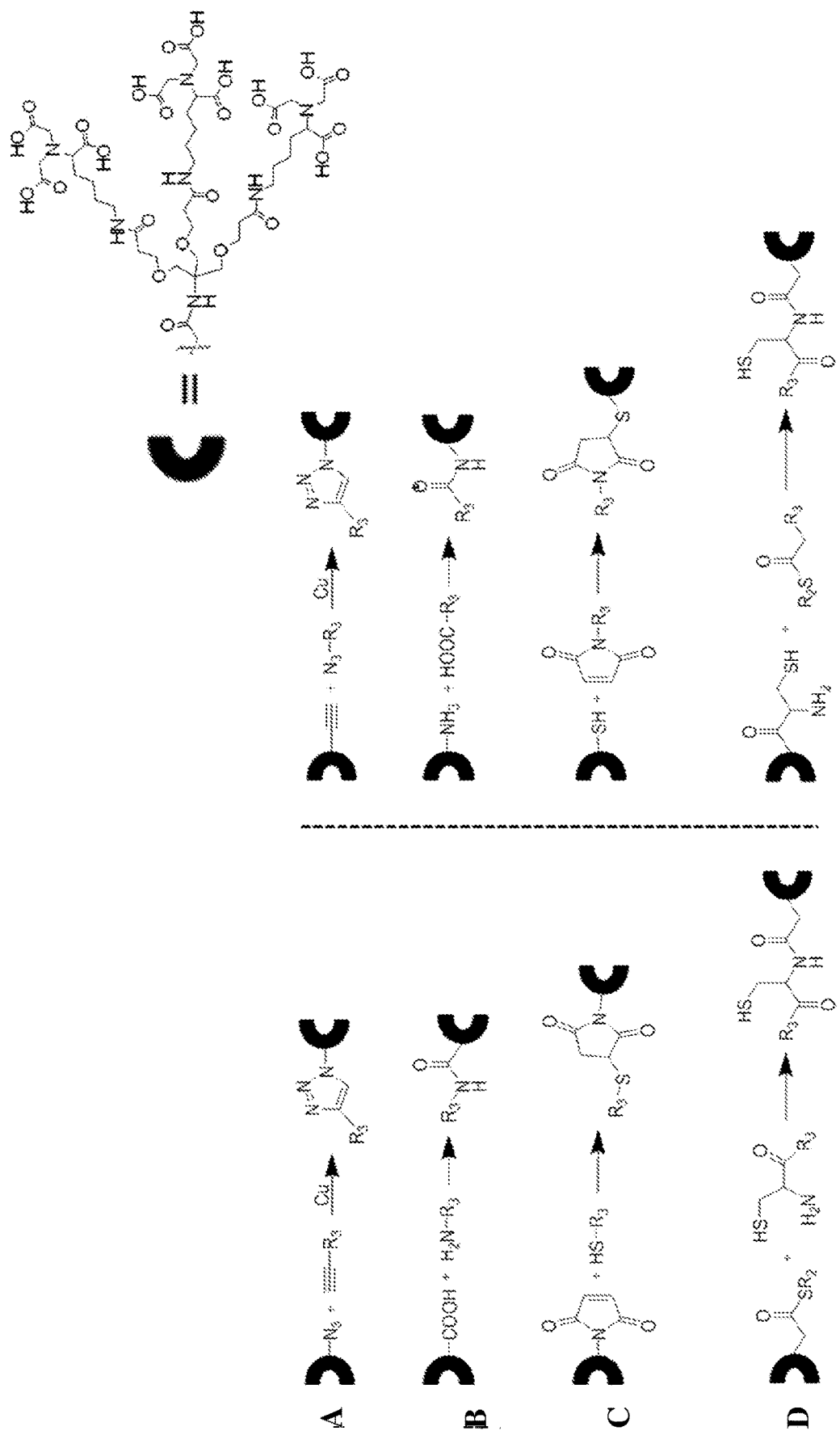
FIG. 9 depicts examples of different reactions that can be utilized to modify the His-tag binding compounds of the invention (the insert shows a specific His-tag binder) for a variety of linkers and compounds.

These functionalities, as well as various other functionalities, can be used to attach compound 10u (FIG. 6, and the insert in FIG. 9), as well as its t-Bu-protected precursor or compound C3 (FIG. 7) to a variety of compounds using the click reaction (FIG. 9A), carboxylic acid-amine coupling (FIG. 9B), thiol-malimide coupling (FIG. 9C), or native chemical ligation (FIG. 9D).

FIG. 10 shows specific examples of how modified tri-NTA compounds can be attached to DNA, small molecules, and peptides.

Example 3

Figure 12:
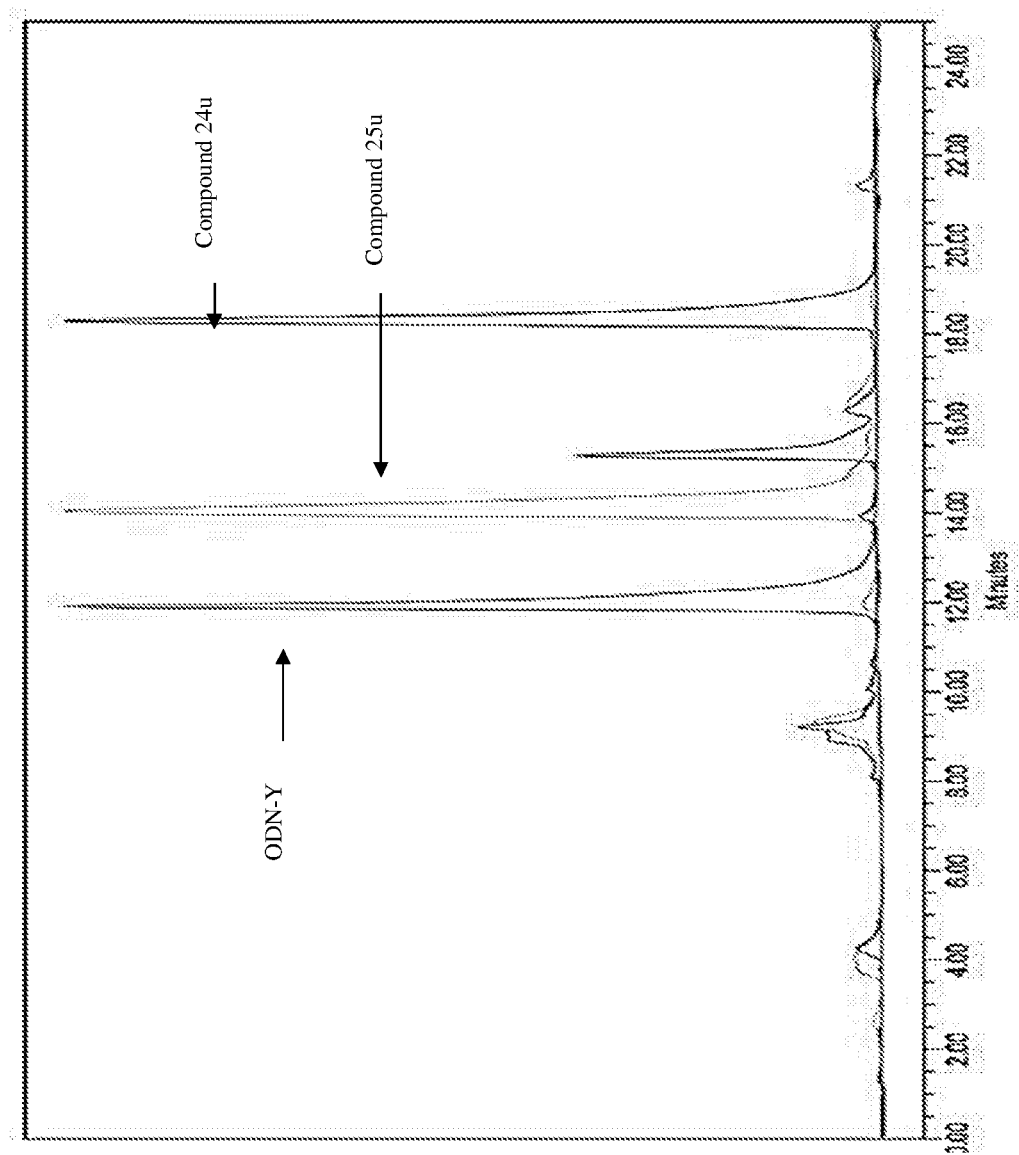
FIG. 12 depicts HPLC chromatogram of the reaction mixture (left) for preparing ODN-Y and of the pure product (ODN-Y, right).
Figure 12:
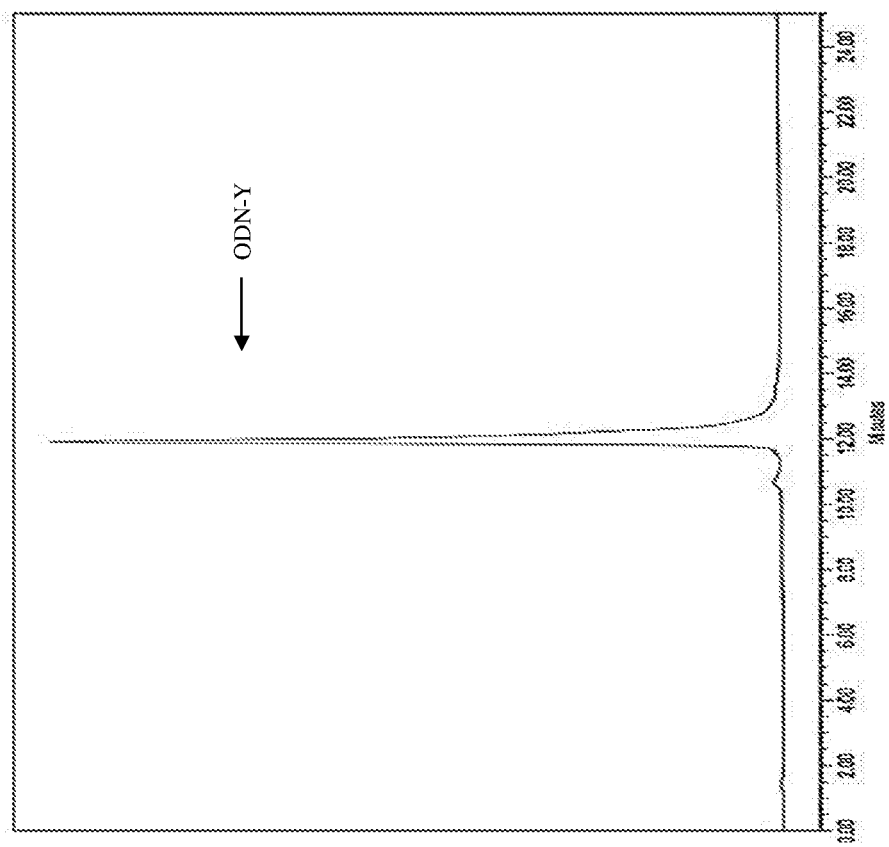

Synthesis Procedures, Characterization, and Binding Studies of a Specific his-Tag Binder An oligonucleotide (ODN) modified with a tri NTA group (FIG. 11, ODN-Y) was prepared by reducing a dithiol-modified ODN (24u) with DTT and reacting the resulting product (25u) with 10u via Michael addition. ODN-Y was purified using HPLC (FIG. 12) and characterized by MALDI-TOFF. Compound 10u was prepared according to the scheme presented in FIG. 6, where compound 8u is a Maleimidopropionic acid.

The synthesis procedures and the $^1$H-NMR and MS characterization of the various products are described below:

di-tert-butyl-2,2'-((6-(((benzyloxy)carbonyl)amino)-1-(tert-butoxy)-1-oxohexan-2-yl)azanediyl)diacetate (C1)

t-butyl bromo acetate (2.39 ml, 16 mmol) and DIPEA (3.5 ml, 20 mmol) were added to a solution of N-benzyloxycarbonyl-L-lysine tert-butyl ester (1.5 g, 4.02 mmol) in 25 ml DMF. The reaction was purged with argon and then heated to 55° C. and stirred overnight. The excess solvent was removed under high vacuum and 15 ml hexane:ethyl acetate 3:1 was added to the solidified mixture. The mixture was filtered over sinter glass and washed with the same solvent (3×10 ml). The filtrate was concentrated under reduced pressure and the residue was purified by column chromatography (80:20 hexane/EtOAc) to yield the purified product (2.2 g, 97% yield).

$^1$H NMR (CDCl$_3$, 300 MHz): δ 1.44 (s, 18H); 1.47 (s, 9H); 1.50 (m, 2H); 1.54 (m, 2H); 1.65 (m, 2H); 3.21 (m, 2H); 3.31 (t, J=6 Hz, 1H); 3.46 (dd, 4H); 5.09 (s, 2H); 7.33 (s, 5H).

ES-MS (m/z): Calcd: 564.34. Found: 587.32 (M+Na).

di-tert-butyl 2,2'-((6-amino-1-(tert-butoxy)-1-oxohexan-2-yl)azanediyl)diacetate (C2)

C1 (2.2 g, 3.92 mmol) was dissolved in 50 ml MeOH and purged with argon. 10% Pd/C (44 mg) was added and the reaction was stirred vigorously overnight under H$_2$. The mixture was filtered over colite and the solvents from the filtrate were removed under reduced pressure. Yield: 1.6 g, (3.8 mmol), 96%.

$^1$H NMR (CDCl$_3$, 300 MHz): δ 1.44 (s, 27H); 1.65 (m, 4H); 1.81 (m, 2H); 2.99 (t, J=9 Hz, 2H); 3.31 (t, J=6 Hz, 1H); 3.43 (dd, 4H).

ES-MS (m/z): Calcd: 430.3. Found: 431.35 (MH+), 453.42 (M+Na).

di-tert-butyl 3,3'-((2-amino-2-((3-(tert-butoxy)-3-oxopropoxy)methyl)propane-1,3-diyl)bis(oxy)) dipropanoate (7u)

2-Amino-2-hydroxy ethyl-propane-1,3-diol (1.21 g, 10.0 mmol) was dissolved in 2.0 mL of DMSO and cooled to 15° C. under argon. Then, 0.2 mL 5.0M NaOH was injected, followed by dropwise addition of tert-butyl acrylate (5.0 mL, 34 mmol). The reaction mixture was brought to room temperature and stirred overnight. The excess regents and solvents were removed under high vacuum and the residue was purified by column chromatography (70:30 EtOAc/hexane+0.05% v/v NH$_4$OH) to yield colorless oil (1.01 g, 20% yield).

$^1$H NMR (CDCl$_3$, 300 MHz): δ 1.44 (s, 27H); 2.46 (t, J=6.0 Hz, 6H); 3.39 (s, 6H); 3.66 (t, J=6 Hz, 6H).

ES-MS (m/z): Calcd: 505.33. Found: 506.36 (MH+), 528.36 (M+Na).

di-tert-butyl 3,3'-((2-((3-(tert-butoxy)-3-oxopropoxy)methyl)-2-(3-(2,5-dioxo-2,5-dihydro-1H-pyrrol-1-yl)propanamido)propane-1,3-diyl)bis(oxy)) dipropanoate (intermediate product, 9u wherein R is maleimide)

600 mg (1.18 mmol) of 7u was dissolved in 30 ml dry DCM under argon and cooled to 0° C. in an ice bath. Thereafter, EDC (339 mg, 1.7 mmol, 1.5 eq) and DIPEA (413.7 µL, 2.32 mmol, 2 eq) were added and the reaction mixture was stirred for 30 min. 3-Maleimidopropionic acid (240.1 mg, 1.4 mmol, 1.2 eq) was added, and the solution was stirred overnight. Then 40 mL DCM was added and the solution was washed with water (10 mL) and brine (10 mL). The organic layer was dried with Na$_2$SO$_4$, filtered, and concentrated at high vacuum. Finally, the crude product was purified by column chromatography (97:3 DCM/MeOH) to yield a yellow oil (501.6 mg, 64%).

$^1$H NMR (CDCl$_3$, 300 MHz): δ 1.44 (s, 27H); 2.44 (t, J=6 Hz, 6H); 2.51 (t, J=6 Hz, 2H); 3.63 (t, J=6 Hz, 6H); 3.67 (s, 6H); 3.80 (t, J=6 Hz, 6H); 6.69 (s, 2H). ES-MS (m/z): Calcd: 656.35. Found: 657.44 (MH+), 679.31 (M+Na).

3,3'-((2-((2-carboxyethoxy)methyl)-2-(3-(2,5-dioxo-2,5-dihydro-1H-pyrrol-1-yl)propanamido)propane-1,3-diyl)bis(oxy))dipropanoic acid (9u)

Deprotection of the tert-butyl group was done with 50% trifluoroacetic acid in DCM (v/v) for 2.5 h. The product was washed repeatedly with DCM and then dried under high vacuum.

$^1$H NMR (D$_2$O, 300 MHz): 2.47 (t, J=6 Hz, 2H); 2.59 (t, J=6 Hz, 6H); 3.61 (s, 6H); 3.67-3.75 (m, 8H); 6.83 (s, 2H).

ES-MS (m/z): Calcd: 488.16. Found: 489.18 (MH+), 511.12 (M+Na) 977.03 (2M+H) 999.15 (2M+Na).

Tert-Butyl Protected Tri-NTA (Intermediate Product).

A solution of compound 9u (160 mg, 304.8 µmol) in 10 ml dry DCM was cooled to 0° C. in an ice bath and DIPEA (212 µL, 1.2 mmol, 4 eq), EDC (191 mg, 1 mmol, 3.3 eq), and HOBt (41 mg, 304.8 µmol, leg) were added consecutively. After 15 min, compound C2 (433 mg, 1 mmol, 3.3 eq) was added and the reaction was stirred overnight. Then 40 mL DCM was added and the solution was washed with water (10 mL). The organic layer was dried with $Na_2SO_4$, filtered, and concentrated at high vacuum. Finally, the crude product was purified by column chromatography (96:4 DCM/MeOH) to yield a colorless oil (96.6 mg, 18.3%).

$^1$H NMR (MeOD, 300 MHz): δ 1.50 (s, 54H); 1.55 (s, 27H); 1.71 (m, 18H); 2.42 (t, 6H); 2.49 (m, 2H); 3.20 (t, 6H); 3.31 (m, 12H); 3.55-3.74 (m, 17H); 6.84 (s, 2H).

ES-MS (m/z): Calcd: 656.35. Found: 657.44 (MH+), 679.31 (M+Na).

Maleimide-Modified Tri-NTA (10u)

Deprotection of the tri-NTA t-butly groups was done with 50% trifluoroacetic acid in DCM (v/v) for 2.5 h. The product was washed repeatedly with DCM and then dried under high vacuum.

$^1$H NMR (MeOD, 300 MHz): δ 1.47 (m, 6H); 1.53 (m, 6H); 1.91 (m, 6H); 2.43 (m, 8H); 3.17 (m, 6H); 3.58-3.65 (m, 15H); 4.1 (m, 14H); 6.82 (s, 2H). ES-MS (m/z): Calcd: 1220.48. Found: 1221.53 (MH+), 1243.39 (M+Na).

Following the successful preparation of 10u, a His-tag binding strand (ODN-Y, FIG. 11) was also prepared by reducing a dithiol-modified ODN (24u) with DTT and reacting the resulting product (25u) with 10u via Michael addition. ODN-Y was purified using HPLC (FIG. 12) and characterized by MALDI-TOFF.

Example 4

Determination of the Dissociation Constant for the his-Tag-ODN-Y Interaction

Figure 13:
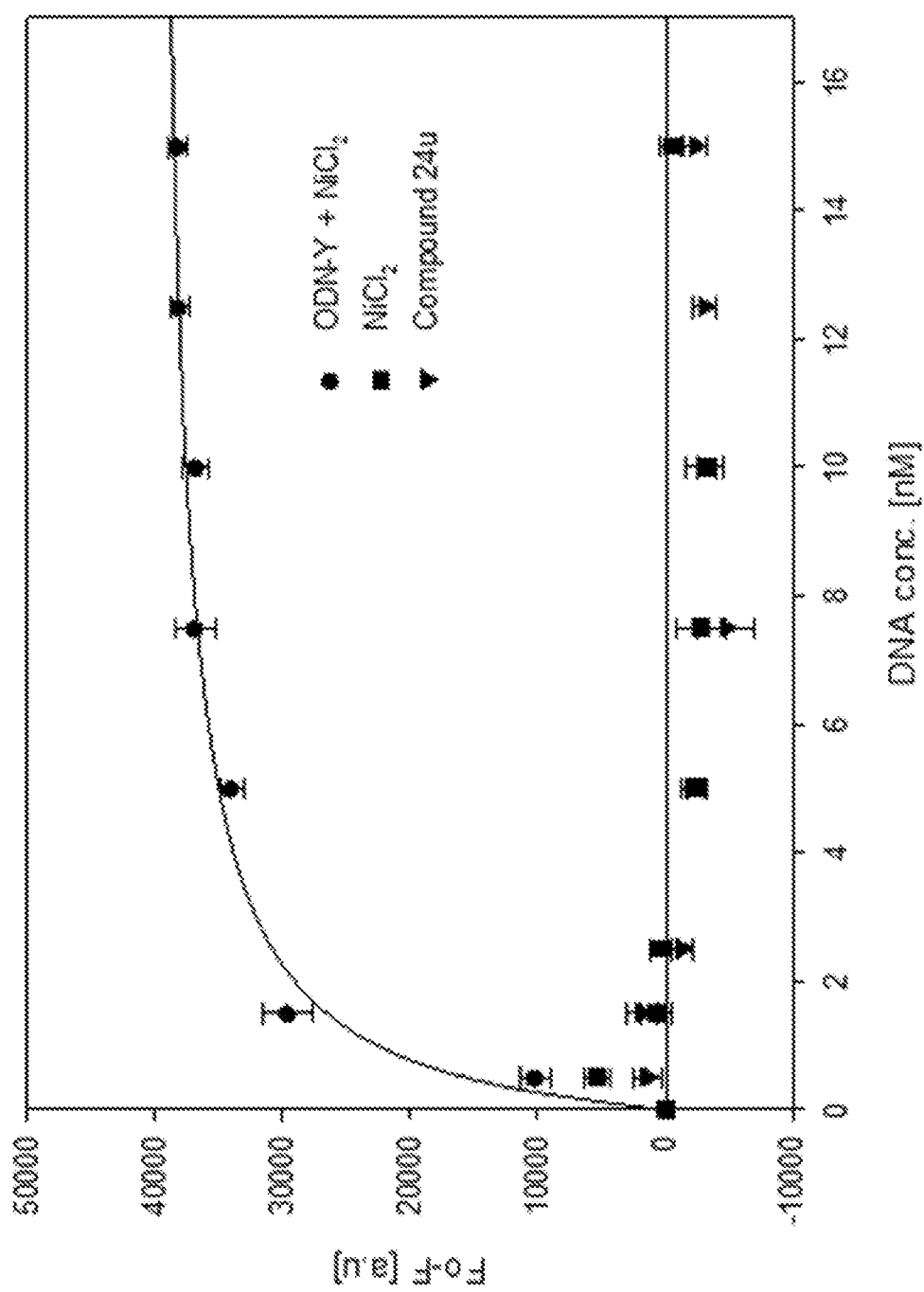
FIG. 13 depicts His-tag compound binding assay. Changes in the fluorescence of a fluorescein-labeled His-tag peptide (5 nM) upon the addition of increasing concentrations of ODN—Y—Ni(II) in PBS. Compound 24u (FIG. 11) and $NiCl_2$ were tested as negative controls.

ODN Y was incubated with nickel chloride and the binding of the resulting complex to His-tag was confirmed by following the decrease in the emission signal of a fluorescein-labeled His6 peptide upon incremental addition of ODN—Y—$Ni^{+2}$ (FIG. 13). The dissociation constant ($K_d$) was determined by subtracting the fluorescence signal of the complex from the signal of the His6 peptide alone. The binding curve fitting and $K_d$ calculation were done using SigmaPlot software. The Kd value was found to be 3.2±0.4 nM.

Example 5

Binding Measurements of Sensors of the Invention to his-Tagged Protein

His-tagged calmodulin (His-CaM) (FIG. 2, state a) was selected as the first protein of interest (POI) for testing this approach because, upon binding to $Ca^{+2}$ ions, this calcium-binding protein exposes a large hydrophobic cleft that can potentially accommodate a complementary synthetic receptor (FIG. 2, state b). In addition, this hydrophobic patch is involved in various binding interactions, which should enable testing the suitability of the technique for identifying binding partners (FIG. 2, state c).

Five compounds were prepared, which share the same His-tag binder and fluorophore, but differ in their appended receptors (FIG. 14). Compound 1, which possesses a hydrophobic receptor, was designed to interact with the hydrophobic surface of His-CaM($Ca^{+2}$) (FIG. 2, State b). In contrast, the other compounds, which possess negatively charged (2), polar (3), positively charged (4), as well as positively charged and hydrophobic (5) receptors were designed to serve as control compounds, which would not respond to changes in the surface of His-CaM.

In principle, compounds 2-5 could also be used to sense changes in the surfaces of other His-tag-labeled proteins. In all compounds (1-5), complexation of tri-nitrilotriacetic acid (tri-NTA) ligand (I) with nickel ions forms the His tag binder, which is connected via a tri-ethylene glycol spacer to a tripodal peptide (II) and a dansyl group (III), which serve as a protein surface receptor, and a solvatochromic probe, respectively.

Figure 15:
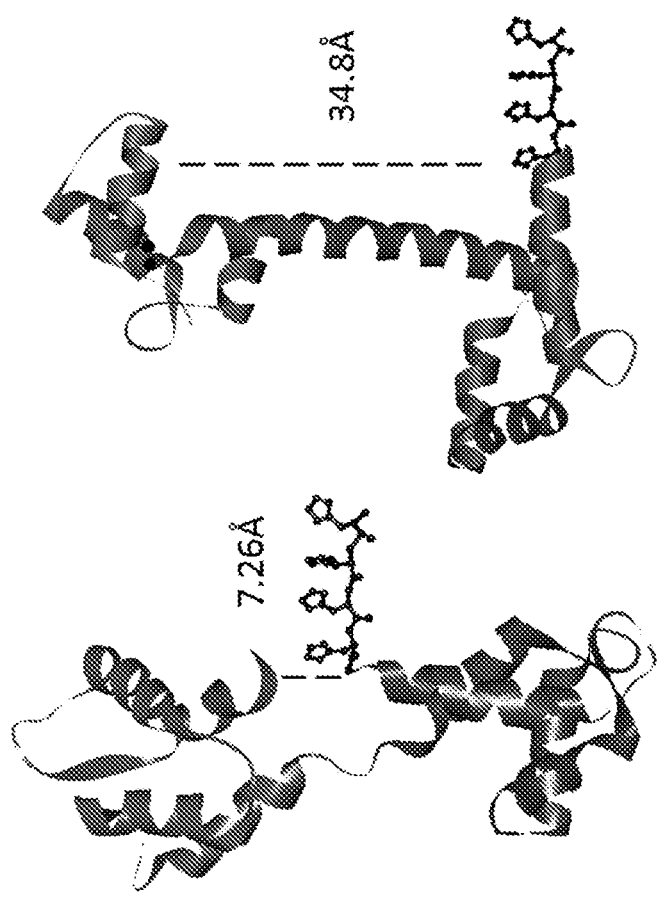
FIG. 15 depicts (a) Visualization of CaM in the calcium-free (left panel) and calcium-bound (right panel) conformations, showing the distance between the N' and C' termini. The proteins' images were generated with Discovery Studio Visualizer 2.5, which was also used to calculate the distance. (b) Approximate length of the sensor 1.
Figure 15:
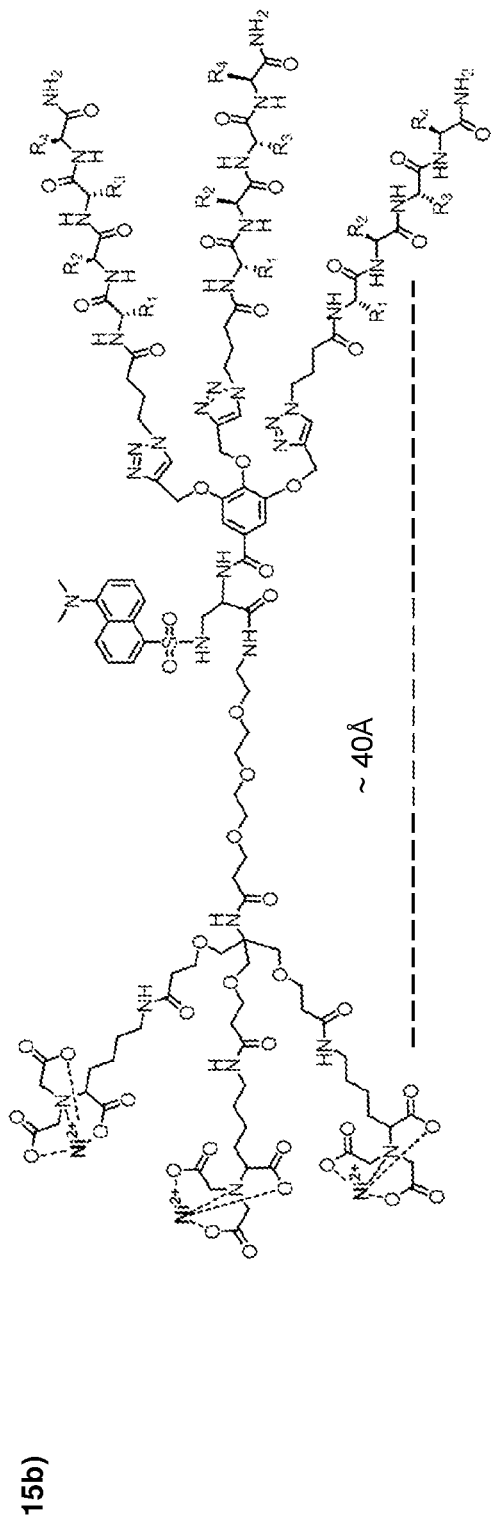

A modeling program showed that the length of the spacer is sufficient to bind various locations of CaM's surface and, in particular, to allow simultaneous binding of the sensor to both the His-tag and the hydrophobic patch on His-CaM ($Ca^{+2}$) (FIG. 15).

Prior to measuring the sensor's performance, it was confirmed that 1 can bind to His-CaM in each of its states, namely, before (FIG. 2a) and after the sunsequent binding to $Ca^{2+}$ (FIG. 2b) and binding partners (FIG. 2c). Fluorescence binding studies were performed first, to confirm that 1 can bind His-tag with nanomolar affinity ($K_d$ (approx)=157 nM±21, FIG. 17), akin to other multivalent NTA ligands.

Figure 16:
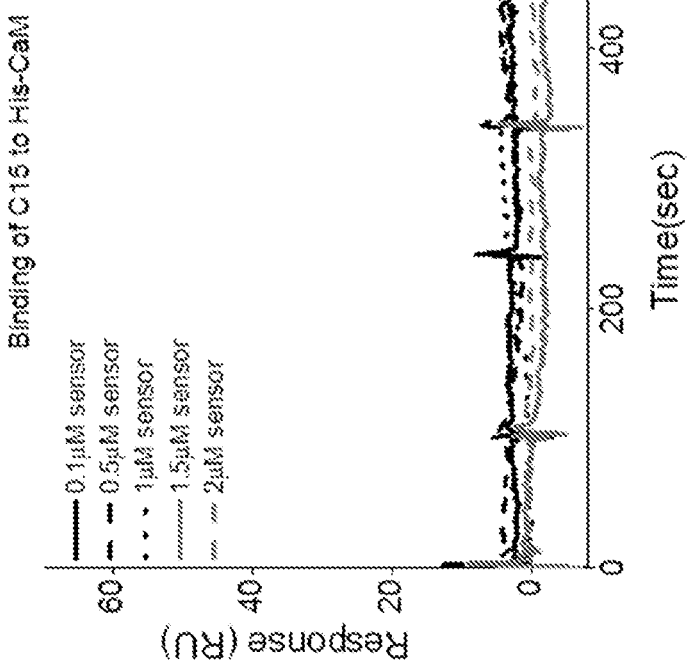
FIG. 16 depicts SPR sensorgrams recorded for the (a) 1-His-CaM and (b) C15-His-CaM interactions.
Figure 16:
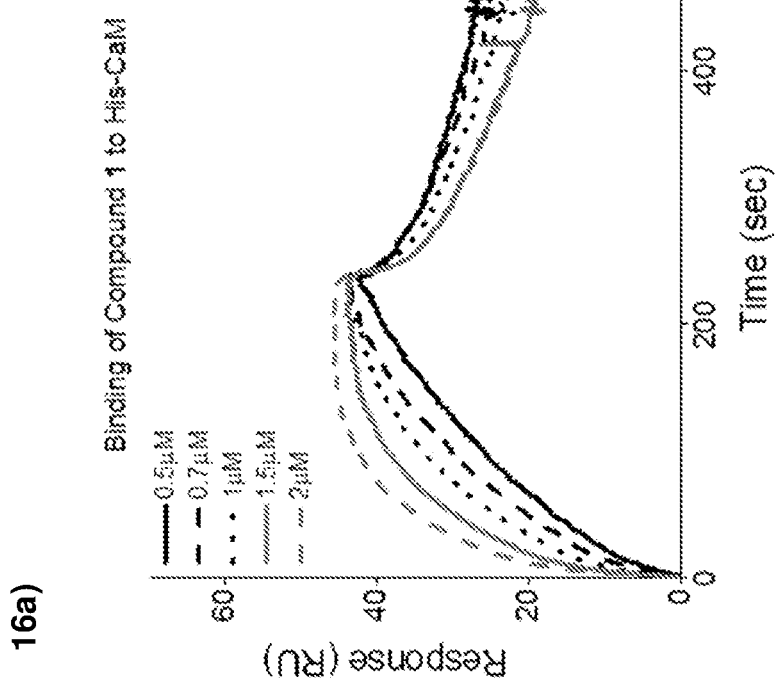
Figure 18:
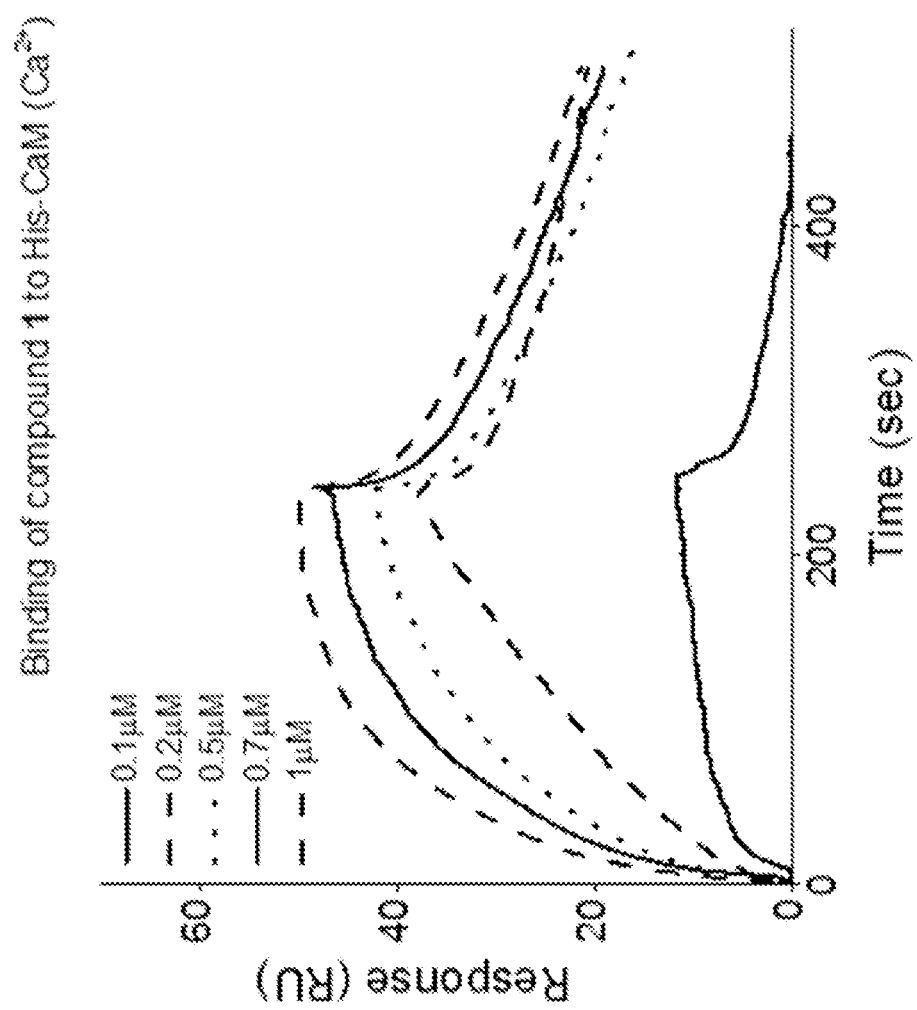
FIG. 18 depicts SPR sensorgrams recorded for the 1-His-CaM(Ca$^{2+}$) interaction.
Figure 19:
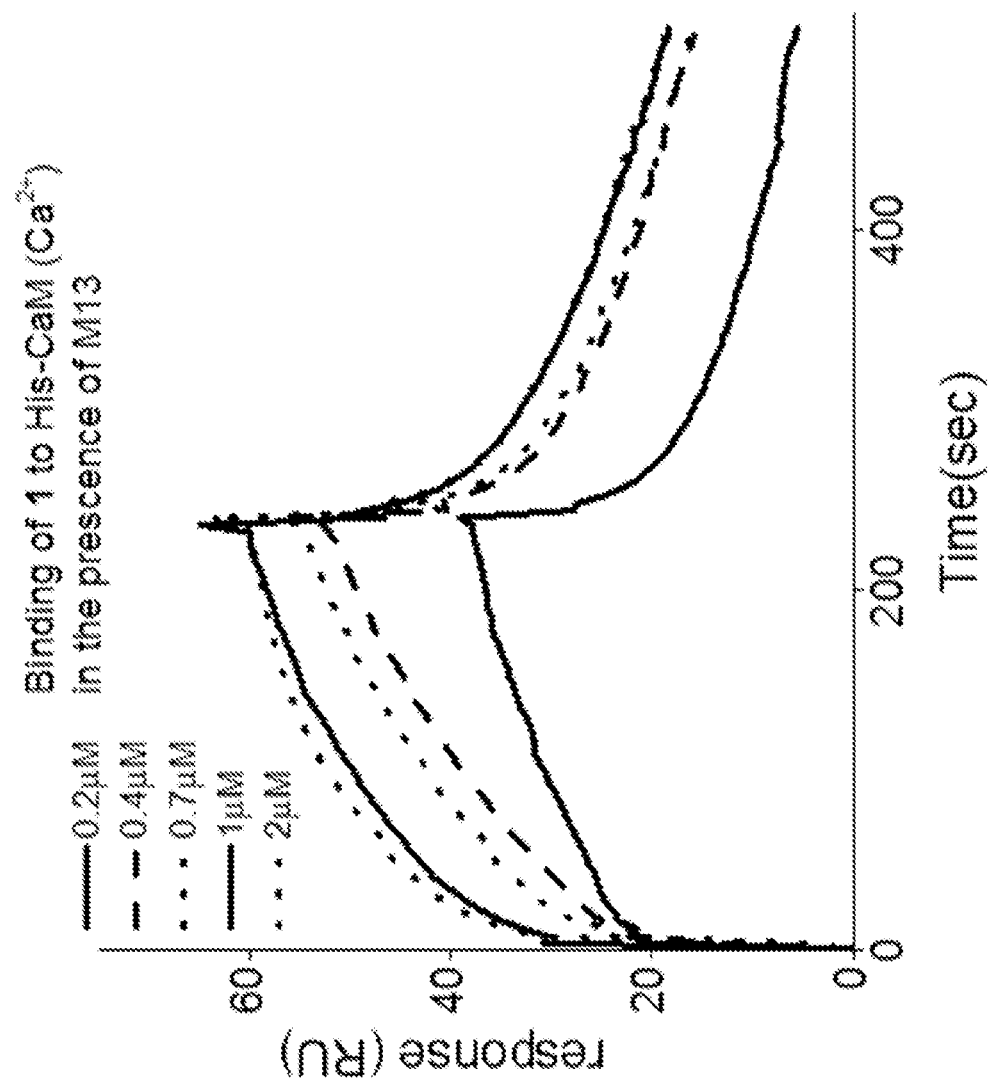
FIG. 19 depicts SPR sensorgrams recorded for the 1-His-CaM(Ca$^{2+}$) interaction in the presence of excess M13.

In the next step, surface plasmon resonance (SPR) measurements were performed (FIG. 16) to ensure that 1 also binds His-CaM ($K_d$ (approx)=176 nM, FIG. 16, left panel) and His-CaM($Ca^{2+}$) ($K_d$ (approx)=134 nM, FIG. 18) with similar affinities. SPR also showed 1 also binds His-CaM ($Ca^{2+}$) in the presence of excess of known binding partner M13 (FIG. 19), which bind to His-CaM($Ca^{2+}$) with low nanomolar affinty. Similar measurements performed in the absence of nickel ions confirmed that apo 1 does not interact with His-CaM (FIG. 16, left panel) indicating the weak affinity of the tripodal receptor toward the surface of His-CaM. Taken together (FIGS. 16 and 18, 19, and Table 2) the SPR studies show that possible interactions between tripodal receptor of 1 and the CaM's surface (FIG. 2, state b) could only be induced by the strong interctions between the tri-NTA-$Ni^{2+}$ complex and the His tag of CaM.

TABLE 2

Summary of dissociation constants that were obtained using SPR experiments.

| Entry | Analyte | Dissociation constant (µM) |
|---|---|---|
| 1 | 1-His CaM | 176 |
| 2 | 1-His CaM ($Ca^{2+}$) | 134 |
| 3 | 1-His CaM ($Ca^{2+}$)-M13 | 231 |
| 4 | 1-His CaM ($Ca^{2+}$)-Mastoparan | 244 |
| 5 | C15- His CaM | — |
| 6 | M13-His CaM ($Ca^{2+}$) | 0.0088 |
| 7 | Mastoparan- His CaM ($Ca^{2+}$) | 0.0012 |

Example 6

Fluorescence Measurements

Sensing Protein Surface Changes with Compounds 1-5

Next, the ability of sensor 1 (200 nM) to detect the $Ca^{+2}$-induced conformational change of His-CaM was tested (FIG. 20a), by following the change in the emission upon the sequential addition of 1) His-CaM (200 nM), 2) $CaCl_2$ (0.3 mM), and 3) EGTA (1.2 mM). As expected from the design, a strong enhancement in dansyl's emission was observed only when calcium ions were added to the solution and this fluorescence was immediately decreased upon the addition of EGTA. Similar fluorescence responses were observed with higher concentrations of sensor and protein, however, the concentrations, which were used in these measurements, were selected after screening for various different conditions (FIG. 21) and selecting the minimal concentrations (200 nM) that can provide strong and reproducible emission signals.

Figure 20:
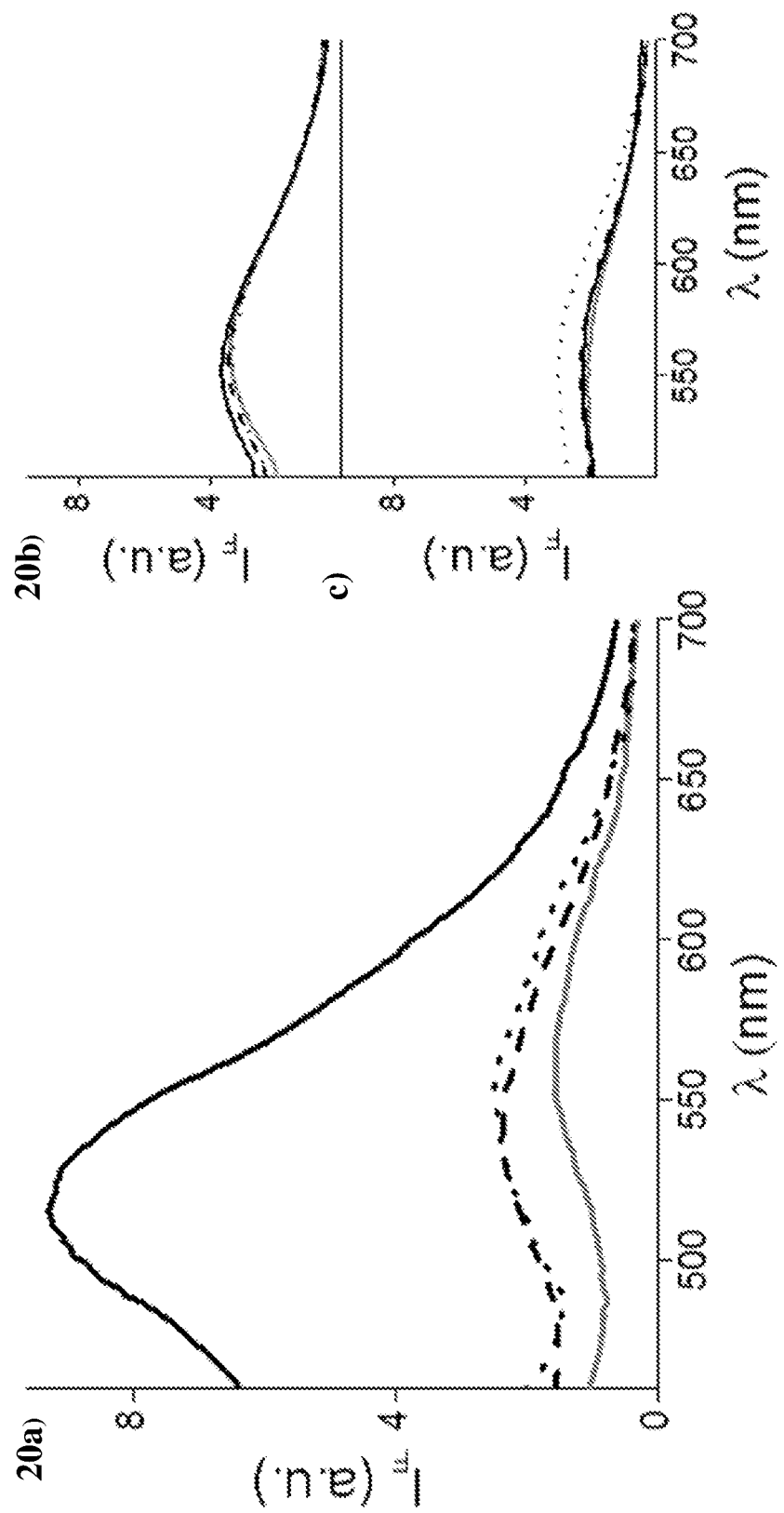
FIG. 20 depicts (a) Fluorescence spectra of 1 (200 nM) before (solid grey line) and after the sequential addition of 200 nM His-CaM (dashed line), 0.3 mM CaCl$_2$ (solid black line), and 1.2 mM EGTA (dotted line). (b) A similar experiment performed in the absence of Ni$^{+2}$ ions. (c) A similar experiment performed with CaM lacking a His-tag. Excitation: 330 nm.
Figure 22:
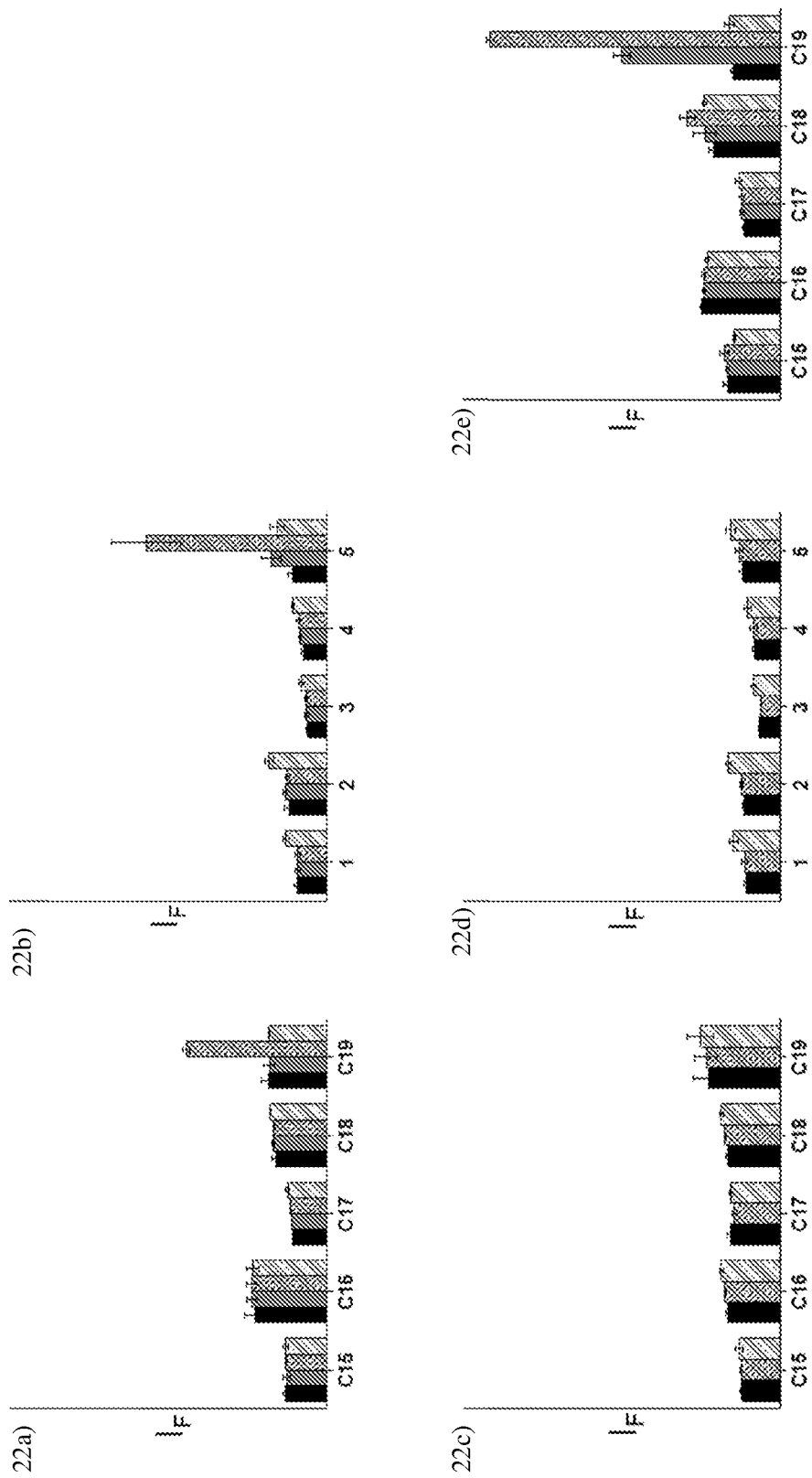
FIG. 22 depicts the fluorescence response of (a) (■) compounds C15-C19 (200 nM) and (b) (■) compounds 1-5 (200 nM) to the sequential addition of (※) CaM (200 nM), (▩) Ca$^{2+}$ (0.3 mM), and (▨) EGTA (1.2 mM). (c) Fluorescence response of (■) compounds C15-C19 (200 nM) and (d) (■) compounds 1-5 to the sequential addition of) (▩) Ca$^{2+}$ (0.3 mM) and (▨) EGTA (1.2 mM) (e) Fluorescence response of (■) compounds C15-C19 (200 nM) to the sequential addition of (※) His-CaM (200 nM), (▩) Ca$^{2+}$ (0.3 mM), and (▨) EGTA (1.2 mM).

To further confirm that the fluorescence enhancement did not result from non-specific interactions between His-CaM ($Ca^{+2}$) and the tripodal receptor, or from the presence of excess of calcium ions in the medium, several control experiments were performed (FIGS. 20 and 22). For example, no change in the emission signal was observed when the experiment was repeated in the absence of nickel ions (FIG. 20b), or with CaM that lacks the His-tag (FIG. 20c). Similarly, sensor 1 did not respond to the addition of $Ca^{+2}$ only (FIG. 22). Taken together with the SPR measurements (FIG. 16, right panel), these control experiments confirm the proposed sensing mechanism, in which the simultaneous binding of sensor 1 to both the His-tag and the hydrophobic surface of His-CaM($Ca^{+2}$) (FIG. 2, state b) is crucial for obtaining the observed effect.

Example 7

Figure 23:
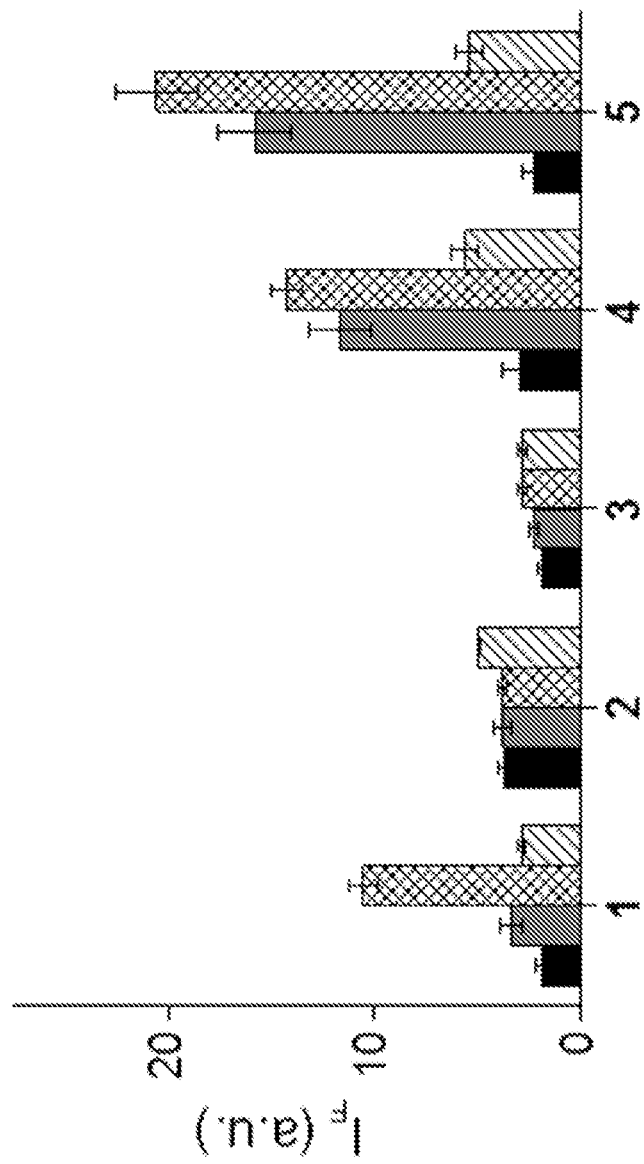
FIG. 23 depicts a Fluorescence response of compounds 1-5 (■) to the sequential addition of His-CaM (※), Ca$^{+2}$ (▩), and EGTA (▨).

The Effect of the Peptide Character on the Fluorescence Response of Sensors of the Invention As noted before, an important aspect of the proposed approach is the ability to "tune" the properties of the tripodal peptide, in such a way that would enable the receptor to interact primarily with a specific region (or a modification) on the protein's surface (FIG. 2, state b). This principle was validated by repeating the above experiments with the four additional control compounds (2-5, FIG. 23), which do not contain hydrophobic receptors. As shown in FIG. 23, a simple alteration in the sequence of the appended peptides had a dramatic effect on the fluorescence response. Specifically, the emission of compounds with negatively charged (2) or polar (3) receptors was not enhanced by the sequential addition of His-CaM and calcium ions, indicating that these sensors do not interact with the surface of His-CaM or His-CaM($Ca^{+2}$). In contrast, sensors with positively charged (4) or hydrophobic and positively charged (5) receptors generated high fluorescence signals both in the presence and absence of calcium ions, which most likely result from electrostatic interactions with negatively charged side chains on the surface of this acidic protein (pI=3.9-4.3). This experiment also indicates that structural activity relationship (SAR) studies could be used to further improve the efficiency of such systems.

Example 8

Figure 24:
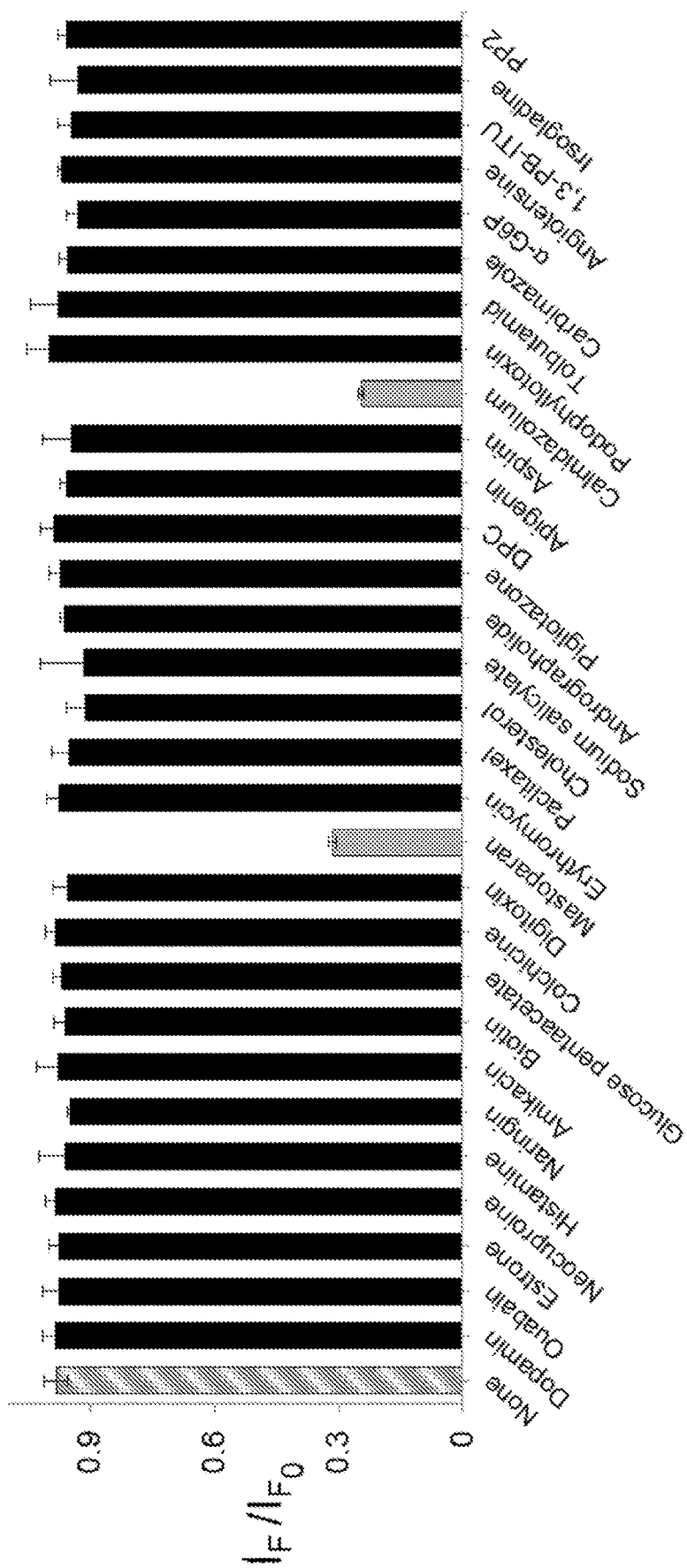
FIG. 24 depicts Fluorescence emission generated by the His-CaM(Ca$^{+2}$)-1-complex (200 nM) in the absence (▨) and presence of 1.6 µM of randomly selected drugs (■), and known CaM inhibitors calmidazolium and mastoparan (※).

The Fluorescence Response of Sensor of the Invention to the Addition of a Variety of Randomly Selected Drugs The ability to detect changes in protein surfaces opens up new possibilities for using such sensors to identify binding partners (FIG. 2, state c). Unlike enzyme inhibitors that can be readily detected by enzymatic assays, identifying molecules that interact with protein surfaces is generally complicated by the need to use antibodies and stepwise protocols, or special techniques such as fluorescence anisotropy or surface plasmon resonance (SPR) (FIG. 16). To determine whether synthetic molecules that bind to the CaM surface can be identified by our system, we followed the fluorescence response of the His-CaM($Ca^{+2}$)-1 complex (FIG. 2, state b) to the addition of a variety of randomly selected drugs, as well as the known CaM inhibitors calmidazolium and mastoparan (FIG. 24). A decrease in the fluorescence emission was observed only in the presence of the CaM inhibitors, which is expected from the release of the protein-bound receptor upon the formation of the His-CaM($Ca^{+2}$)-drug complex (FIG. 2, state c).

Example 9

The Fluorescence Response of Sensor of the Invention to the Addition of Natural Binding Partners The ability of sensor 1 to detect natural binding partners was tested. This is a more challenging goal to achieve because the sensor must be inert to the presence of large proteins that may also possess hydrophobic patches on their surfaces and/or proteins that tend to engage in non-specific interactions such as serum albumin (e.g., BSA and HSA). Accordingly, the His-CaM($Ca^{+2}$)-1 complex was incubated with 12 different proteins (FIG. 25), among which CaMKII and Drp1 are known to be CaM binding partners, whereas M13 is the binding fragment (26 aa peptide) of the skeletal muscle myosin light chain kinase (sk-MLCK). The response of the system to the known binding partners and, most importantly, the recovery of emission by the addition of a competing CaM (that lacks His-tag) provide evidence for the ability of the system to identify specific protein partners.

Example 10

Figure 26:
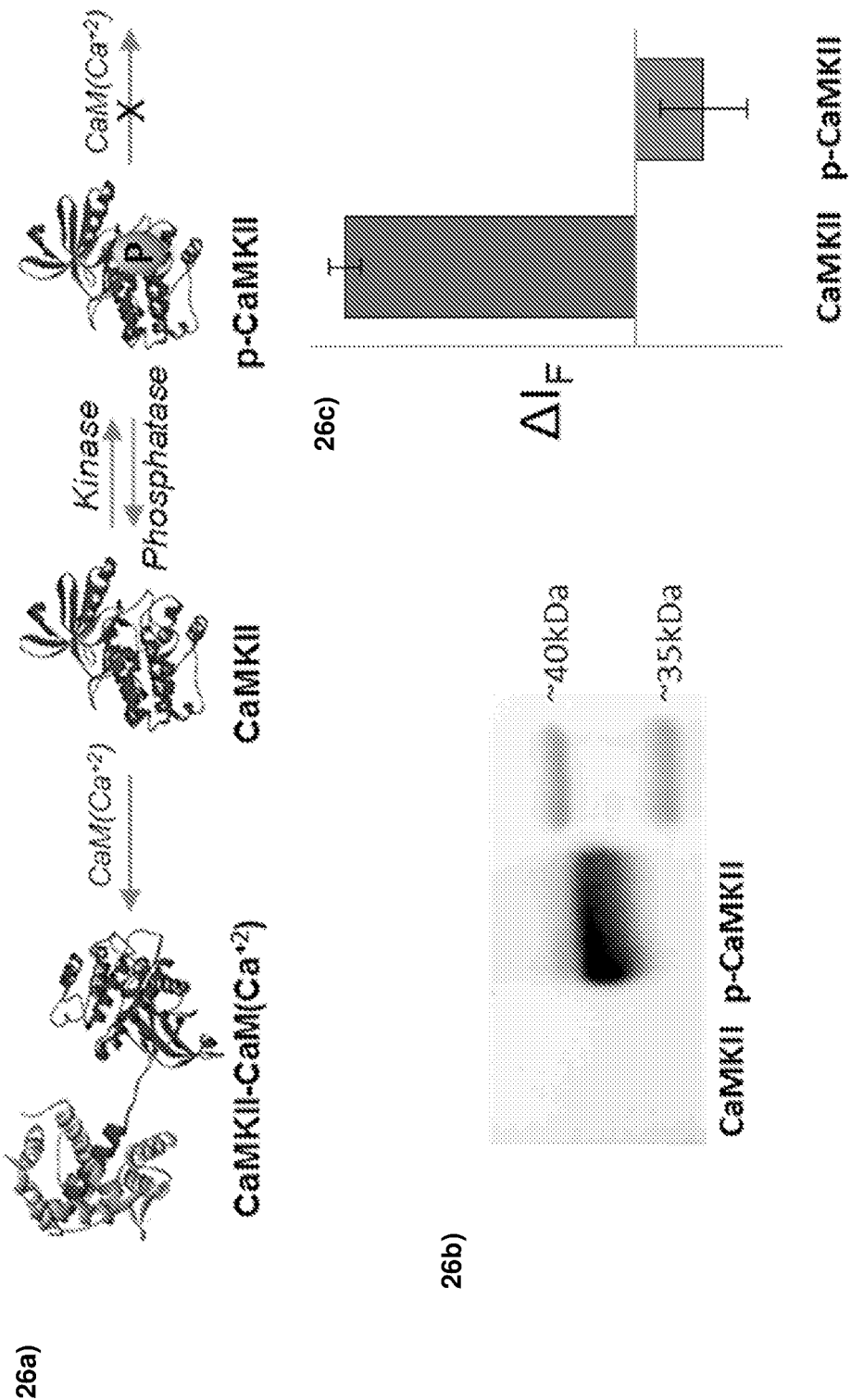
FIG. 26 depicts (a) Schematic illustration showing the preferential binding of CaM(Ca$^{+2}$) to a non-phosphorylated CaMKII. The phosphate group on p-CaMKII is denoted as Ⓟ (b) Determining the phosphorylation state of CaMKII by a conventional western blot technique. (c) Determining the phosphorylation state of CaMKII (800 nM) by recording the fluorescence response of His-CaM(Ca$^{+2}$)-1 (200 nM) to addition of CaMKII and p-CaMKII.

Detection of Surface Modifications in Unlabeled Proteins by Sensors of the Invention The system was also probed to detect surface modifications of unlabeled proteins. As a proof-of-principle, the phosphorylation state of calmodulin-dependent protein kinase II was determined (CaMKII, FIG. 26) using the His-CaM($Ca^{+2}$)-1 complex. CaM($Ca^{+2}$) is known to bind only the dephosphorylated state of this enzyme (FIG. 26a) and hence, it was expected that a decrease in the fluorescence signal will be observed only in response to a dephosphorylated CaMKII. Accordingly, p-CaMKII was treated with phosphatase to obtain CaMKII (see experimental details in Example 19 below) and the phosphorylation state of samples containing p-CaMKII or CaMKII was initially determined by conventional western blot analysis (FIG. 26b). Although this technique can be used to distinguish between the samples, it is a laborious process that normally takes 1-2 days, in which proteins are separated using SDS-PAGE and transferred to a membrane to allow the binding of primary and secondary antibodies. This approach also requires multiple incubation and washing steps, and a specific antibody for each modification. In contrast, this system could determine the phosphorylation state of each sample within seconds, simply by incubating the protein with a solution containing the His-CaM($Ca^{+2}$)-1 complex (FIG. 26c).

Example 11

Detection of Binding Interactions Between Bcl-2 and BAX by Sensors of the Invention The sensing of His-CaM's surface by the tripodal receptor of 1 supports previous studies, in which it was shown that bringing a non-specific synthetic receptor in the vicinity of a protein, is likely to promote interactions between this receptor and the surface of the protein target. It was therefore expected that even a small sensor library, consisting of only five different receptors (FIG. 23, compounds 1-5), would be sufficient for identifying sensors that can detect surface modifications of His-tag labelled proteins, which are not related to CaM. The ability of compounds 1-5 to detect the interactions between Bcl-2 and Bax was tested. These proteins belong to Bcl-2 family, which plays an important role in regulating apoptosis. The interaction between Bcl-2 and an amphipathic alpha helical peptide of Bax (Bax-BH3), in particular, prevents Bax from triggering apoptosis. As shown in FIG. 27a, of the different compounds tested, the emission of the amphipathic sensor 5, was most signicantly ennhanced upon binding to His-Bcl-2 and this emission was decreased when the Bax-BH3 peptide was added. Other proteins, as well as M13 and mastoparan that were previously detected by the His-CaM($Ca^{+2}$)-1-complex (FIG. 24), did not change the emission signal generated by the His-Bcl-2-5 complex. In addition, no change in the emission signal was observed in the absence of nickel ions (FIG. 28), which further demonstrate the selectivity and binding mechanism of such sensors.

Example 12

Fluorescence Response of Compounds 1-5 to CaM Surface Modifications

Experimental Details

Figure 21:
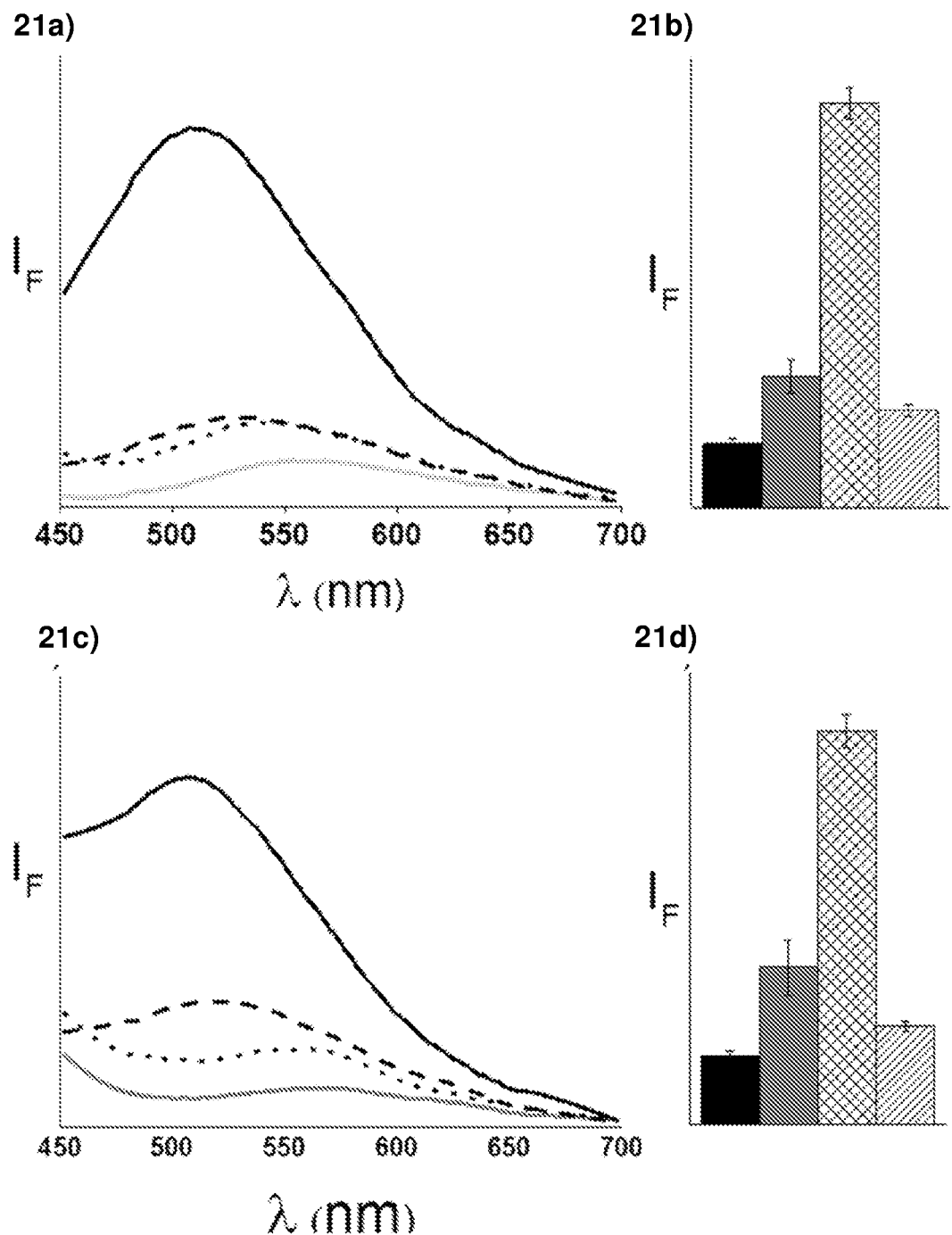
FIG. 21 depicts the fluorescence spectra of 1 (200 nM) before (solid grey line) and after the sequential addition of (a) 400 nM His-CaM (dashed line) or (c) 600 nM His-CaM (dashed line), 0.3 mM CaCl$_2$ (solid black line), and 1.2 mM EGTA (dotted line). The fluorescence response of (■) compound 1 (200 nM) to the sequential addition of (b) (※) His-CaM (400 nM) or (d) (※) His-CaM (600 nM), (▩) Ca$^{2+}$ (0.3 mM), and (▨) EGTA (1.2 mM).

Compounds 1-5 (50 µL, 12 µM) in phosphate buffer (4.1 mM, pH=7.3) were dispensed into a 384-well plate and fluorescence intensities were recorded with an excitation wavelength of 330 nm. His-CaM (final concentration, 200 nM), $CaCl_2$ (final concentration, 0.3 mM), and EGTA (final concentration, 1.2 mM) were subsequently added to each well and the fluorescence intensity values were recorded again (FIGS. 22 and 20). The emission values correspond to the maximal intensities recorded either at $\lambda_{em}$=510 nm or at $\lambda_{em}$=560 nm. Fluorescence was measured in triplicate. Data shown in FIGS. 20 and 22 are the average of the triplicates and error bars represent standard deviation. Control experiments were performed in a similar manner (FIGS. 22a-e) and with higher His-CaM concentrations (FIG. 21).

Example 13

Fluorescence Response of Compounds 1-5 to Protein G Surface Modifications

Experimental Details

Compounds 1-5 (50 µL, 10 µM) in phosphate buffer (4.1 mM, pH=7.3) are dispensed into a 384-well plate and fluorescence intensities are recorded with an excitation wavelength of 330 nm. His-Protein G (final concentration, 200 nM) and IgG (final concentration, 800 nM) are subsequently added to each well and the fluorescence intensity values are recorded again. The emission values obtained, correspond to the maximal intensities recorded either at $\lambda_{em}$=530 nm or at $\lambda_{em}$=560 nm. Fluorescence is measured in triplicate. Control experiments are performed in a similar manner.

Example 14

Fluorescence Response of Compounds 1-5 to Bcl-2 Surface Modifications

Experimental Details

Figure 27:
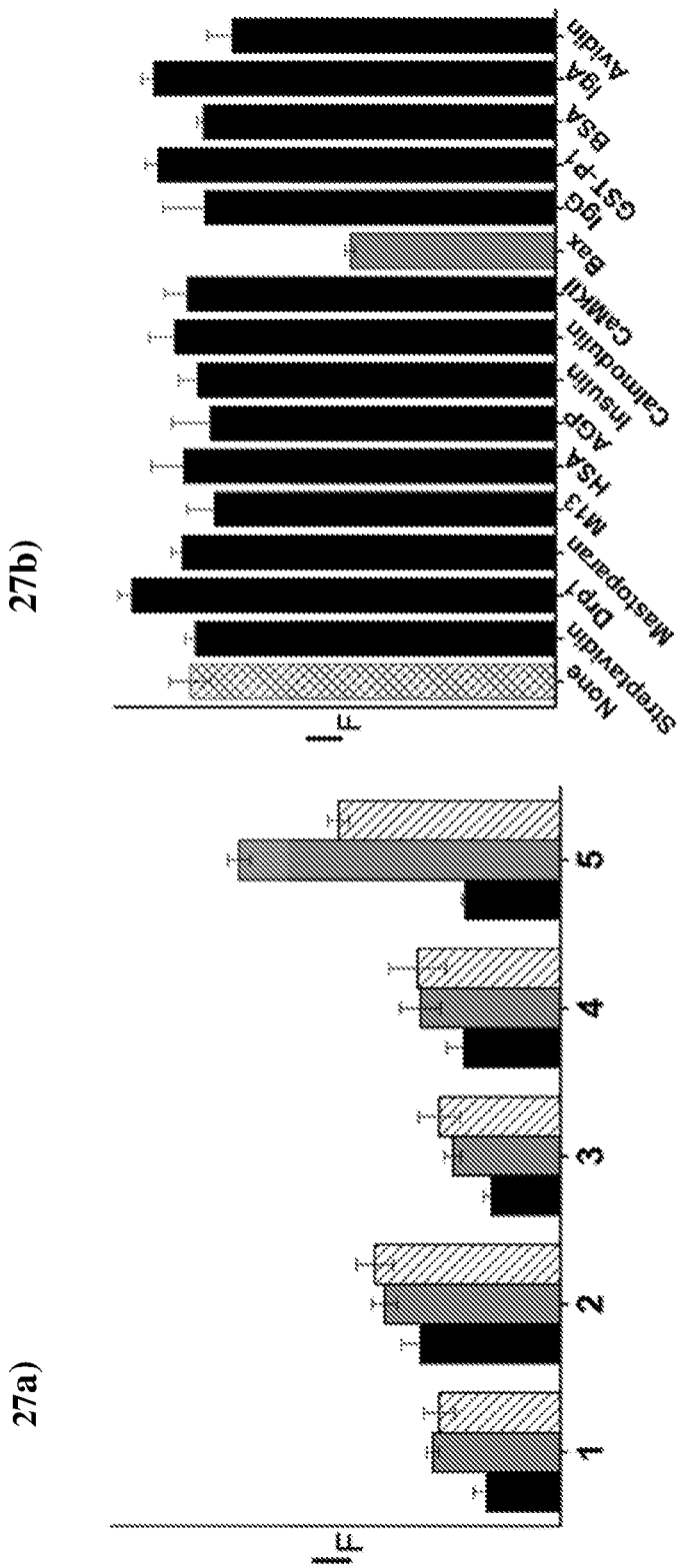
FIG. 27 depicts fluorescence response of a) (■) compounds 1-5 (200 nM) to the sequential addition of (※) His-Bcl-2 (200 nM) (▨) Bax-BH3 (1.6 mM). b) Fluorescence of the His-Bcl-2-5 complex (200 nM) before (▩) and after the addition of 800 nM of randomly selected proteins (■), as well as the known Bcl-2 binding partner: Bax BH3 (※).
Figure 28:
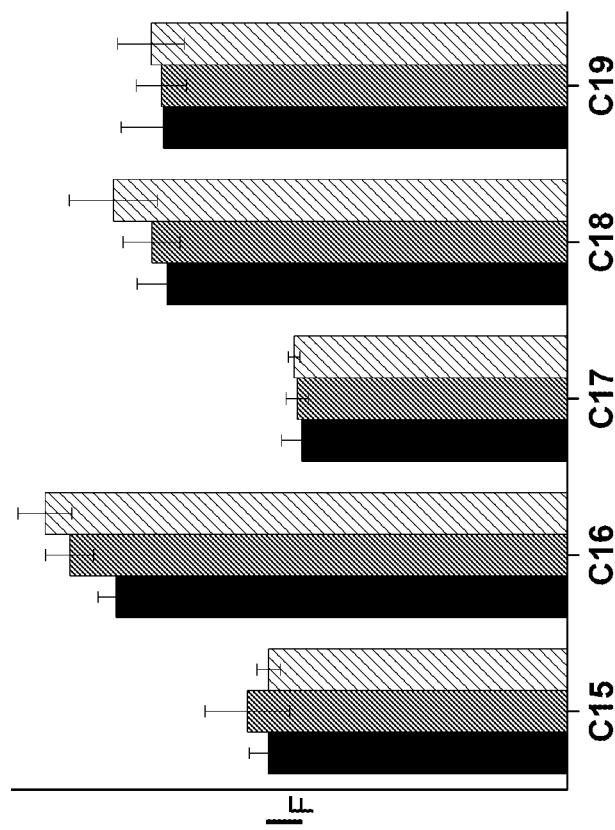
FIG. 28 depicts fluorescence response of (■) compounds C15-19 (200 nM) to the sequential addition of (※) His-Bcl-2 (200 nM) (▩) Bax BH3 (1.6 mM).

Compounds 1-5 (50 µL, 10 µM) in phosphate buffer (4.1 mM, pH=7.3) were dispensed into a 384-well plate and fluorescence intensities were recorded with an excitation wavelength of 330 nm. His-Bcl-2 (final concentration, 200 nM) and Bax BH3 (final concentration, 1.6 µM) were subsequently added to each well and the fluorescence intensity values were recorded again. The emission values correspond to the maximal intensities recorded either at $\lambda_{em}$=530 nm or at $\lambda_{em}$=560 nm. Fluorescence was measured in triplicate. Data shown in FIG. 27 is the average of the triplicates and error bars represent standard deviation. Control experiments were performed in a similar manner (FIG. 28).

Example 15

Screening Assay with Different Small Molecules and Peptide Inhibitors

Experimental Details

A mixture of compound 1 (200 nM), His-CaM (400 nM), and $CaCl_2$ (0.3 mM) in PBS buffer (4.1 mM, pH=7.3) was dispensed into a 384-well microplate, and fluorescence emission spectra were recorded. Then various drugs (1.6 µM) and peptides (1.6 M) were added and the fluorescence emission was again recorded. Fluorescence measurements were performed in triplicate and the emission intensities before the addition of each drug were normalized to 100% (FIG. 24).

Example 16

Screening Assay for Protein Protein Interactions Using Surface Sensors

Experimental Details

Probing Protein Protein Interactions for Calmodulin

Figure 25:
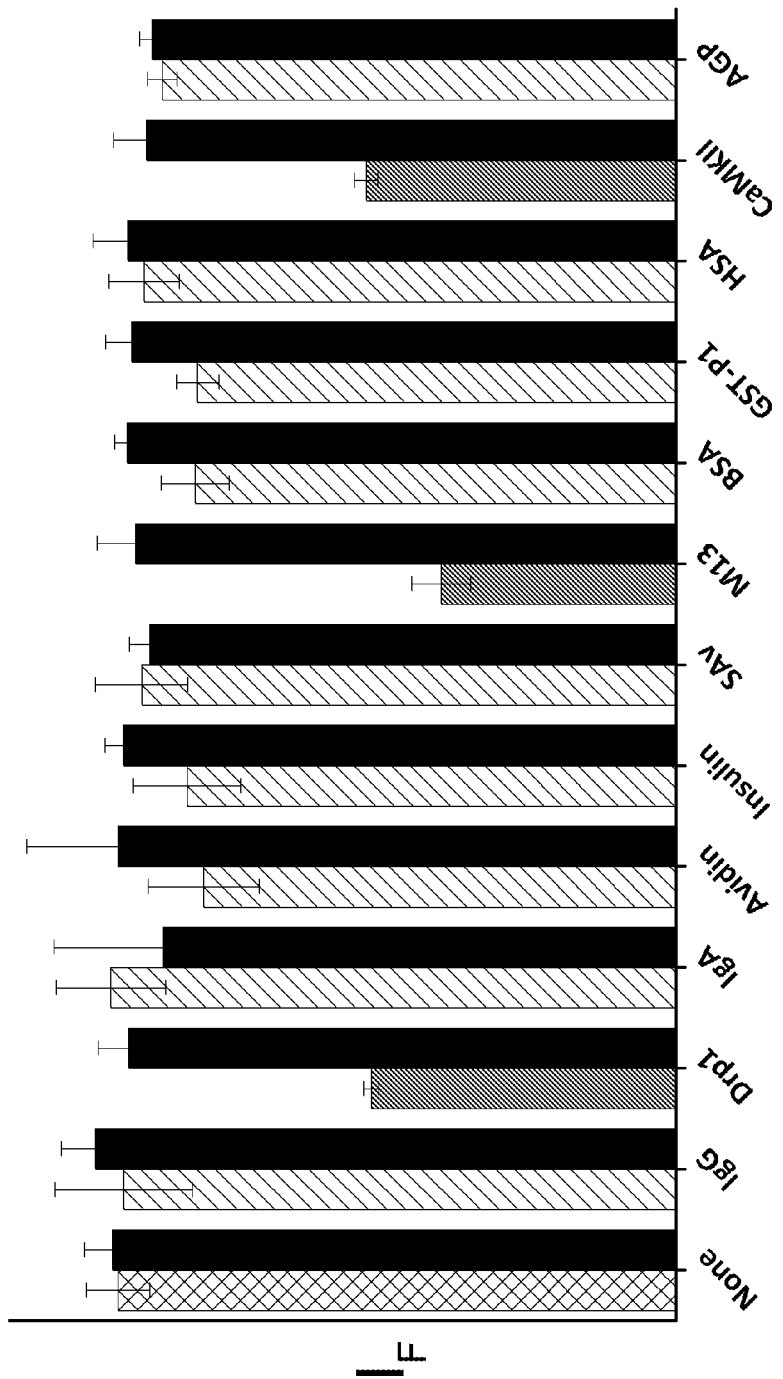
FIG. 25 presents the fluorescence of the His-CaM(Ca$^{+2}$)-1-complex (200 nM) before (▩) and after the addition of 800 nM of randomly selected proteins (▨), as well as known CaM binding partners: CaMK-II, M13, and Drp1 (※). The black bars correspond to emissions recorded in the presence of a competing CaM, which lacks a His-tag (1.6 µM).

A mixture of compound 1 (200 nM), His-CaM (200 nM), and $CaCl_2$ (0.3 mM) in PBS buffer (4.1 mM, pH=7.3) was dispensed into a 384-well microplate, and the fluorescence emission spectra were recorded. Various proteins (0.8 µM) and M13 peptide (0.8 µM) were added and the fluorescence emission was again recorded. As a competing binding partner CaM (1.6 µM) was added. Fluorescence measurements were performed in triplicate. The emission intensities before the addition of each protein were normalized to 100% (FIG. 25).

Probing Protein Protein Interactions for Protein G

A mixture of compound 5 (200 nM) and His-protein G (200 nM) in PBS buffer (4.1 mM, pH=7.3) is dispensed into a 384-well microplate, and the fluorescence emission spectra are recorded. Various proteins (0.8 µM) and IgG (0.8 µM) are added and the fluorescence emission is again recorded. Fluorescence measurements are performed in triplicate. The emission intensities before the addition of each protein are normalized to 100%.

Probing Protein Protein Interactions for Bcl-2

A mixture of compound 5 (200 nM) and His-Bcl-2 (200 nM) in PBS buffer (4.1 mM, pH=7.3) was dispensed into a 384-well microplate, and the fluorescence emission spectra were recorded. Various proteins (0.8 µM) and Bax BH3 peptide (0.8 µM) were added and the fluorescence emission was again recorded. Fluorescence measurements were performed in triplicate. The emission intensities before the addition of each protein were normalized to 100% (FIG. 27b).

Example 17

Dissociation Constant

Experimental Details

The approximate dissociation constant for the sensor 1-His tag interaction was determined using a carboxyfluorescein-labeled hexa-histidine peptide. Carboxyfluorescein-labeled hexa-histidine peptide (60 µL, 10 nM) in PBS buffer (4.1 mM, pH=7.3) was dispensed into a 384-well microplate and the fluorescence data were recorded using excitation and emission filters of 485/20 and 580/20, respectively, and a 510 nm cut-off mirror. Then, various concentrations of 1 (final concentrations ranging from 0-650 nM) were added to the wells and the fluorescent intensities were recorded again. The complexation of the labeled peptide with compound 1 leads to strong fluorescence quenching, by the chelated transition $Ni^{+2}$ ions. Fluorescence data were collected in triplicate. The data was normalized to 100% for labeled peptide before the addition of sensor 1 and the relative quenching percentages were plotted against the sensor's concentration. The data was then analyzed by fitting to a non-linear regression for single-site saturation ligand binding $$y = \frac{B_{max}x}{K_d + x},$$

Figure 17:
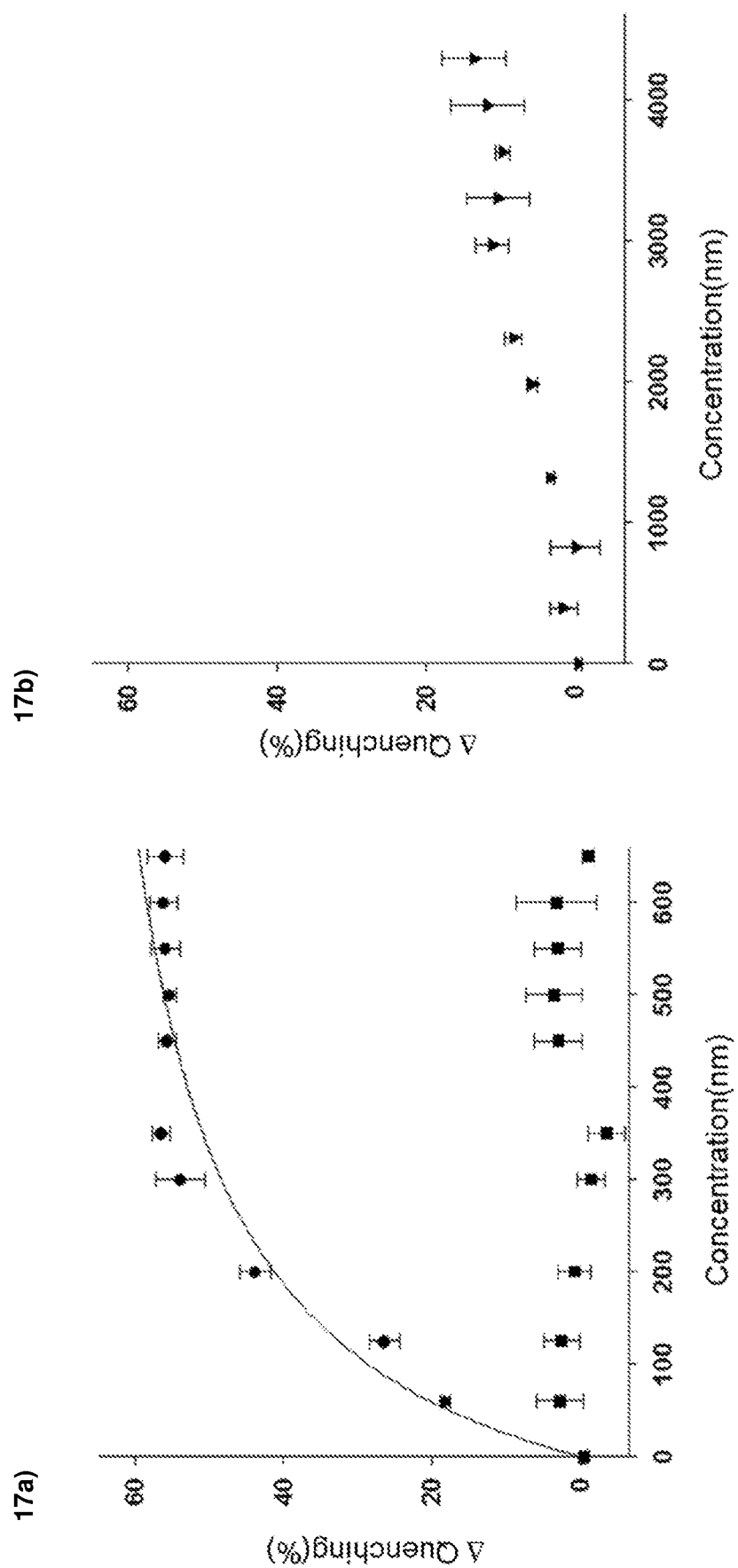
FIG. 17 depicts (a) Binding curves obtained for compound 1 (●) by the addition of increasing amounts of compound 1 to a carboxyfluorescein-labeled hexa-histidine peptide ($K_d$=157±21 nM, $R^2$=0.96). Control experiments (a,b) were performed with C15 (■) and $NiCl_2$(▼).

$B_{max}$=maximum specific binding is 73.82±3) using SigmaPlot 9.0, which resulted in a $K_d$ value of 157±21 nM. The control experiments were performed with C15 and only $NiCl_2$ (FIG. 17).

Example 18

Surface Plasmon Resonance Experiments

Experimental Details

SPR experiments were performed to assess the dissociation constant between His-CaM and the compound 1 in the presence/absence of $Ca^{2+}$ ions and other ligands. His-CaM was diluted in 180 µL PBS buffer (4.1 mM, pH=7.3) and 20 µL sodium acetate (1M, pH=3) to reach a final concentration of 20 µg/mL and then immobilized on a Biacore sensor chip CM5 through EDC/NHS chemistry. Flow cells were activated for 5 min by injecting 50 µL mixture of 50 mM NHS:200 mM EDC. Then 50 µL of His-CaM (20 µg/mL) was injected at a rate of 10 µL/min followed by injection of ethanolamine (1 M) to block the remaining surface-activated groups. Various analytes (Table 1) were injected in different concentrations, ranging from 0.1-2 µM for (20 µL/min, 80 µL injection with a delay of 180 s wash) (Table 1). Between consecutive analyte injections, the surface was regenerated with 2 mM NaOH (20 µL at 10 µL/min) followed by PBS buffer (60 µL at 10 µL/min). Non-derivatized dextran matrix flow cells served as reference cells. For determination of dissociation constants in the presence of M13 or Mastoparan (entries 3 and 4), first 80 µL M13 or Mastoparan (3 µM, 20 µL/min) were injected and after dissociation began 80 µL compound 1 (concentration range of 0.2-2 µM, 20 µL/min) was injected. $CaCl_2$ (0.3 mM) was pre-incubated with the analyte before injections. For the control compound C15 (entry 5), prior to each injection, the chip was washed with 20 µL EDTA (50 mM, 20 µL/min) followed by PBS buffer (20 µL at 20 µL/min) to remove any traces of $Ni^{2+}$. The data were globally fitted using BiaEvaluation software 3.2.

Example 19

CaMKII Assays

Experimental Details

CaMKII Dephosphorylation

CaMKII was dephosphorylated according to a previously published procedure. 0.787 nmol p-CaMKII was incubated with λ-phosphatase (600 U) and $MnCl_2$ (50 mM) at 4° C. overnight. Then the mixture was buffer exchanged into HEPES buffer (20 mM, 0.3 M NaCl, 1 mM $CaCl_2$, pH=7.5) using a 3 kDa cutoff centrifugal filter (Amicon Ultra, Millipore) at 4° C.

CaMKII Western Blot Analysis

Figure 29:
FIG. 29 depicts (a) Fluorescence of the His-CaM (Ca$^{+2}$)-1 complex (200 nM) before (none) and after the addition of 0.8 µM CaMKII and p-CaMKII. (b) Western blot detection of CaMKII and p-CaMKII with anti-flag-tag antibody. Both CaMKII and p-CaMKII are detected by an anti-flag tag antibody whereas only p-CaMKII is detected by phospho-specific antibody, as shown in (b).
Figure 30:
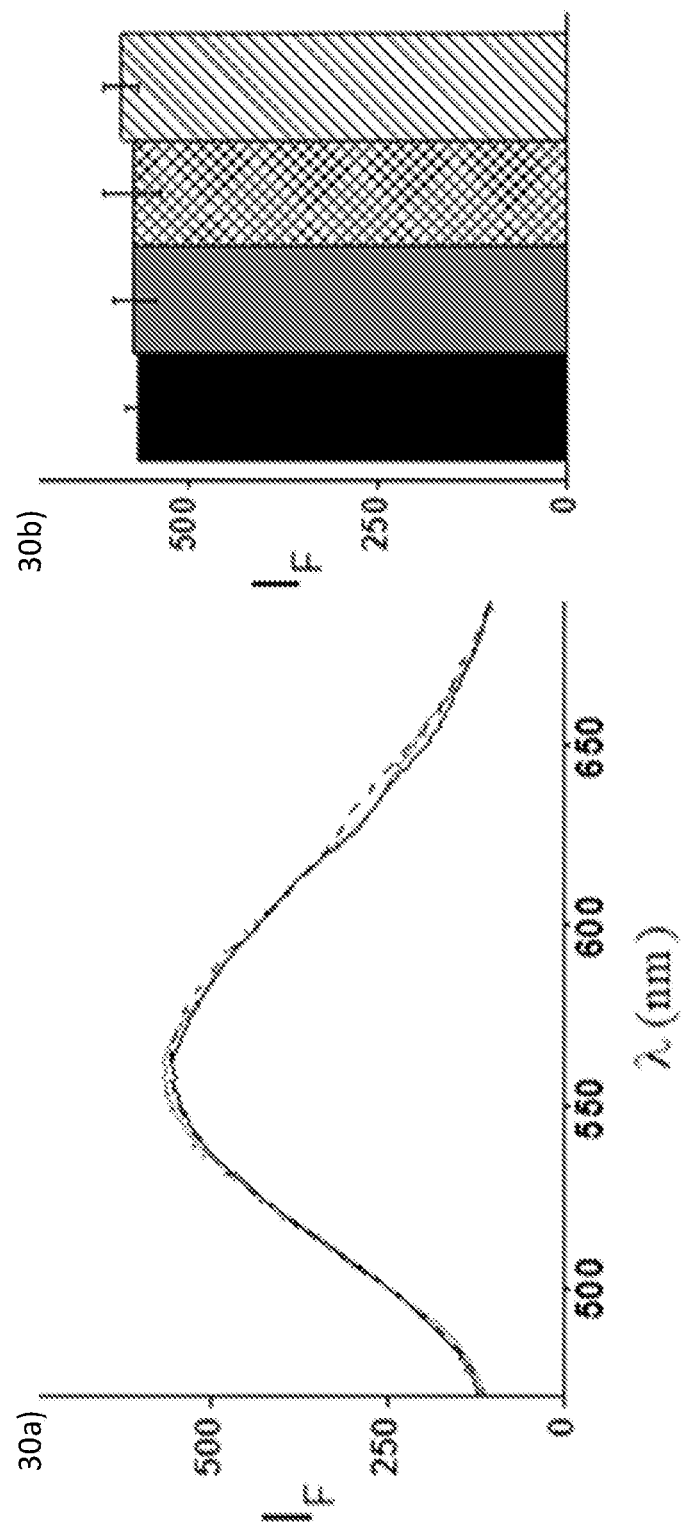
FIG. 30 depicts a-b) Fluorescence response of (■) compounds C15 (2 µM) to the sequential addition of (※) His-CaM (200 nM), (▩) Ca$^{2+}$ (0.3 mM), and (▨) EGTA (1.2 mM).
Figure 31:
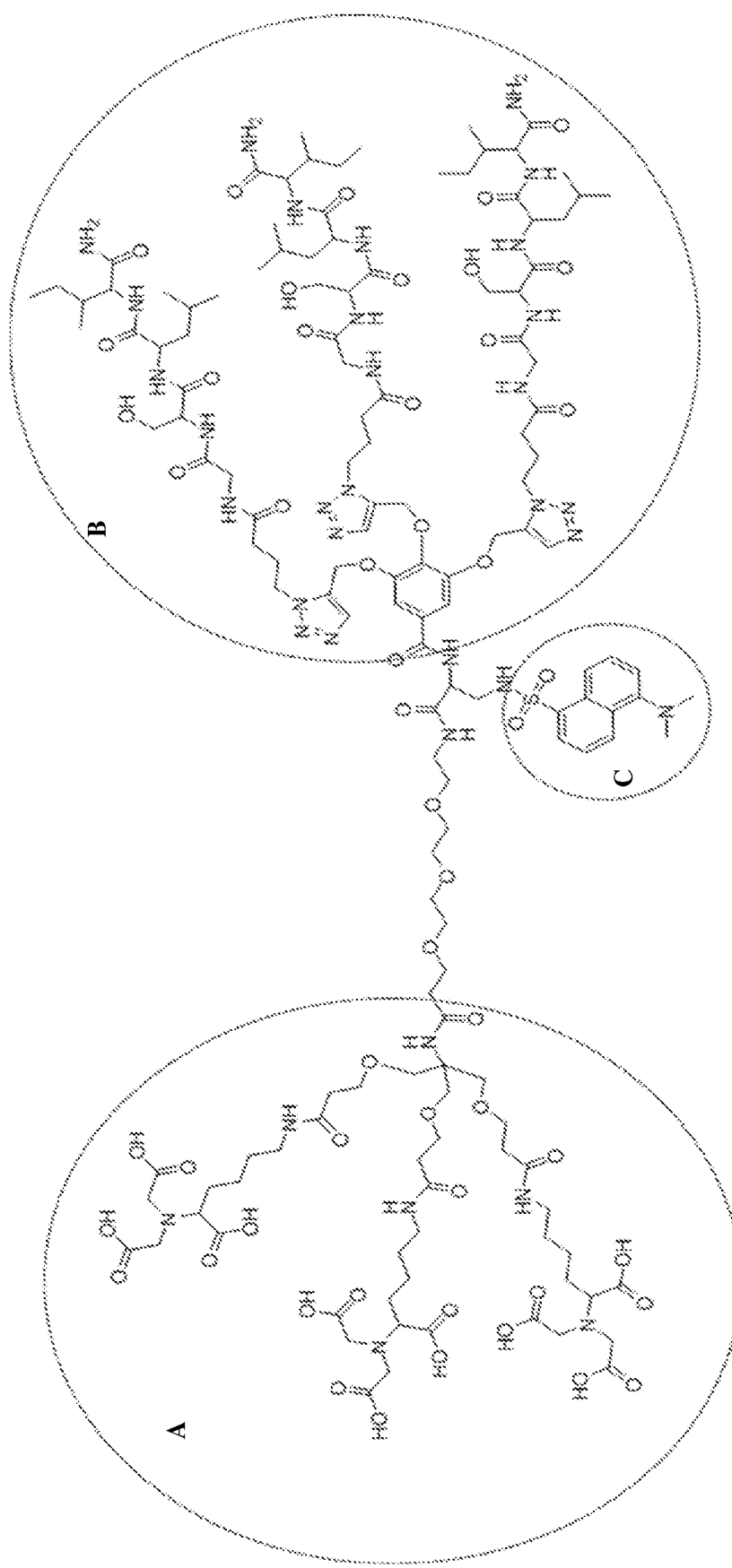
FIG. 31 depicts the protein surface sensor consists of three components. A: A bis-NTA unit for specific His-tag binding. B: A tripodal hydrophobic peptide that serves as a non-selective protein surface receptor. C: A Dansyl group as the solvatochromic fluorophore.

Approximately 2 µg of p-CaMKII and 1 µg of CaMKII were loaded in each western blot run. Proteins were resolved on a 10% SDS-PAGE gel and transferred to a membrane, blocked with 5% BSA in PBST buffer (0.1% Tween), and probed with either antibody specific for p-CaMKII (at a dilution of 1:1000) or anti-flag tag (at a dilution of 1:1000 dilution) as primary antibodies. Intermediate washing between steps was done with PBST buffer. HRP-conjugated goat anti-rabbit was used as secondary antibody (at a dilution of 1:10000). CaMKII is expressed with anti-flag tag, which permits performing loading control analysis. Using the primary antibody that is specific for flag tag, a signal for both p-CaMKII and CaMKII (phosphatase treated) was obtained using BIORAD ChemiDoc™ XRD+ (FIGS. 26 and 29).

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A monomolecular compound that can track changes that occur on the surface of tag-labeled proteins, said compound comprises:
   a. a His-Tag binder;
   b. a non-selective binder;
   c. a fluorophore; and
   a linker, which covalently links between the His-Tag-binder and the non-selective binder;
   wherein the linker is a combination of linear or branched alkyl ether chain of 2-50 carbon atoms and substituted linear or branched alkyl diamide chain of 2-50 carbon atoms;
   wherein the fluorophore is covalently attached to a side chain of the linker in the vicinity to the non-selective binder;
   wherein the non-selective binder comprises at least one peptide; and
   wherein the His-tag binder is represented by the structure of formula D:

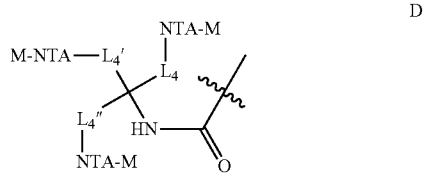

wherein
   each of $L_4$, $L_4'$, and $L_4''$ is independently —$(CH_2)_n$—NHCO—$(CH_2)_m$—O—$(CH_2)_l$—;
   n, m and l are each independently an integer between 1 and 6;

M-NTA is a metal complex of nitrilotriacetic acid; and wherein the wavy line marks the position from which the fragment connects to the linker.

2. The compound of claim 1, wherein the non-selective binder is represented by the structure of formula (A):

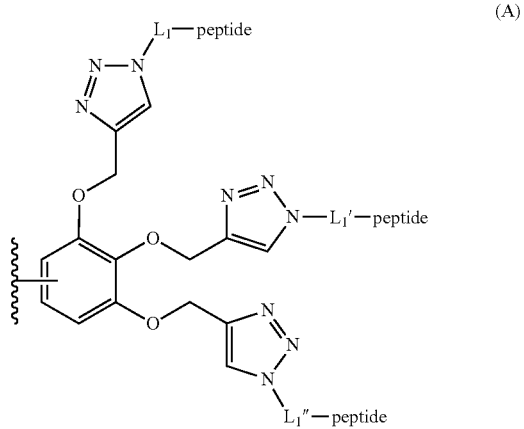

wherein
  each of $L_1$, $L_1'$ and $L_1''$ is independently a substituted or unsubstituted linear or branched alkyl chain of 1-50 carbon atoms, substituted or unsubstituted linear or branched alkyl ether chain of 1-50 carbon atoms, substituted or unsubstituted linear or branched alkyl phosphate chain of 1-50 carbon atoms, substituted or unsubstituted linear or branched alkyl amide chain of 1-50 carbon atoms, substituted or unsubstituted linear or branched alkyl diamide chain of 1-50 carbon atoms, substituted or unsubstituted linear or branched alkyl amine chain of 1-50 carbon atoms or any combination thereof; and wherein a peptide comprises a 2-20 amino acid peptide.

3. The compound of claim 1, wherein M is nickel ion or cobalt ion.

4. The compound of claim 1, wherein said fluorophore is dansyl, fluorescein (6-FAM), FAM, cyanine dyes (e.g. Cy3, Cy5), sulfoindocyanine, nile red, rhodamine, perylene, fluorenyl, coumarin, 7-methoxycoumarin (Mca), dabcyl, NBD, Nile blue, Tamra, BODIPY or derivative thereof.

5. The compound of claim 1, wherein said compound is represented by the structure of formula I:

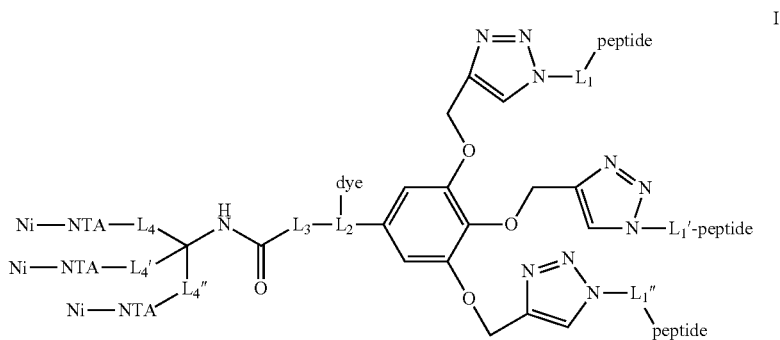

wherein
  each of $L_1$, $L_1'$ and $L_1''$ is independently a first linker, wherein each of said first linkers is a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof;

$L_2$ is a second linker, wherein said second linker is a substituted or unsubstituted linear or branched alkyl diamide chain of 2-50 carbon atoms;

$L_3$ is a third linker, wherein said third linker is a substituted or unsubstituted linear or branched alkyl ether chain of 2-50 carbon atoms; and wherein said dye comprises dansyl, fluorescein (6-FAM), FAM, cyanine dyes (e.g. Cy3, Cy5), sulfoindocyanine, nile red, rhodamine, perylene, fluorenyl, coumarin, 7-methoxycoumarin (Mca), dabcyl or derivative thereof.

6. The compound of claim 5, represented by the structure of formula II:

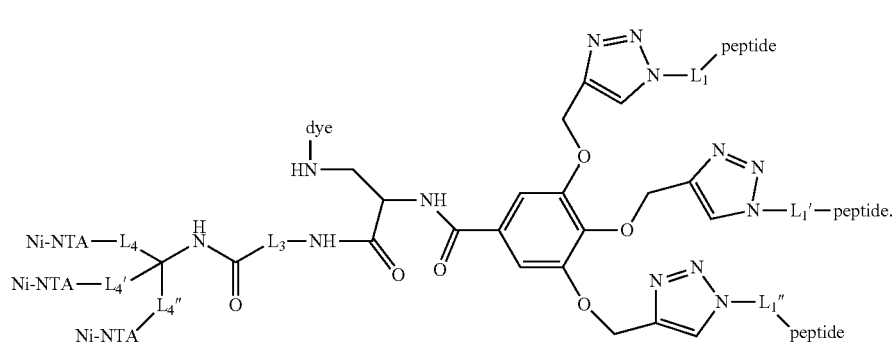

7. A compound represented by the structure of formula III:

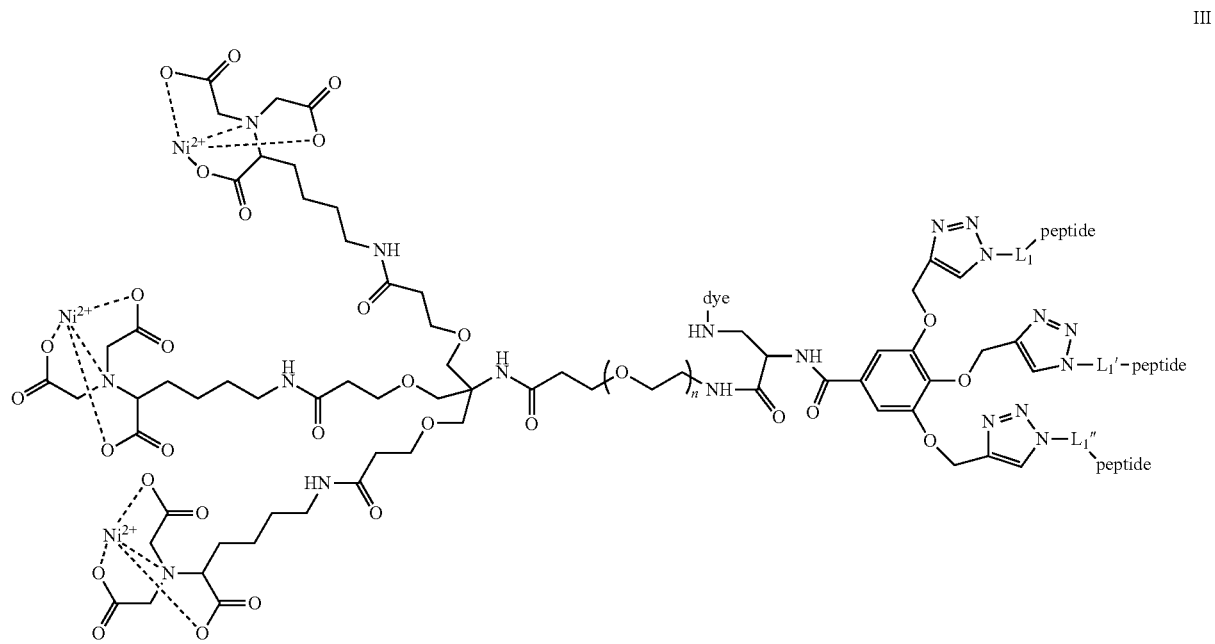

wherein
each of $L_1$, $L_1'$ and $L_1''$ is independently a first linker, wherein each of said first linkers is a substituted or unsubstituted linear or branched alkyl chain of 2-50 carbon atoms, substituted or unsubstituted linear or branched alkyl ether chain of 2-50 carbon atoms, substituted or unsubstituted linear or branched alkyl phosphate chain of 2-50 carbon atoms, substituted or unsubstituted linear or branched alkyl amide chain of 2-50 carbon atoms, substituted or unsubstituted linear or branched alkyl diamide chain of 2-50 carbon atoms, substituted or unsubstituted linear or branched alkyl amine chain of 2-50 carbon atoms or any combination thereof; and n is an integer number between 1 and 20.

8. A compound represented by the structure of formula IV:

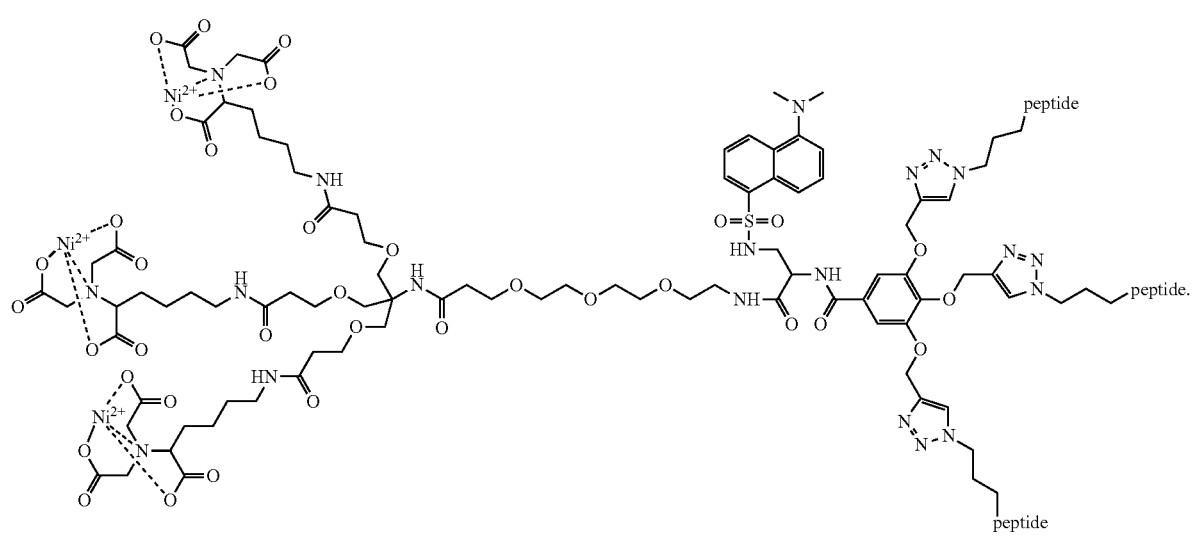

IV

9. A method of identifying a binding partner of protein of interest (POI), said method comprises:
   a. incubating a monomolecular compound according to claim 1, with a His-tagged-POI in solution;
   b. measuring the fluorescence intensity of said solution;
   c. adding a test compound to said solution;
   d. remeasuring the fluorescence intensity of said solution; and
   e. determining binding of said test compound to said His-tagged-POI based on a change in fluorescence intensity, wherein decreased fluorescent intensity indicates binding of said test compound;
   thereby identifying said binding partner for said POI.

10. The method of claim 9, wherein said POI is calmodulin (CaM), calmodulin-$Ca^{2+}$ ($CaM(Ca^{2+})$), G-protein or B-cell lymphoma 2 protein (Bcl-2); wherein said solution further comprises IgG, IgA, Avidine, Insulin, SAv, BSA, GST-P1, HSA, AGP or any combination thereof; or wherein said binding partner is a protein, a peptide, a synthetic molecule, a small molecule, a drug or any combination thereof.

11. A method of localizing a His-tagged polypeptide of interest within a cell, said method comprises the steps of:
   a. expressing said His-tagged polypeptide in a recombinant cell;
   b. incubating said recombinant cell with a monomolecular compound according to claim 1; and
   c. visualizing the fluorescence emission of said monomolecular compound.

12. A method of measuring gene expression of a His-tagged polypeptide of interest in a cell, said method comprises the steps of:
   a. expressing a His-tagged polypeptide in a cell;
   b. incubating said cell with a monomolecular compound according to claim 1; and
   c. measuring the fluorescence of said cell;
   wherein detection of a fluorescent signal is dependent on the formation of a His-tagged polypeptide:monomolecular compound complex.

* * * * *